United States Patent
Rotem-Yehudar et al.

(10) Patent No.: US 9,309,308 B2
(45) Date of Patent: *Apr. 12, 2016

(54) MONOCLONAL ANTIBODIES FOR TUMOR TREATMENT

(71) Applicant: CURETECH LTD., Yavne (IL)

(72) Inventors: Rinat Rotem-Yehudar, Tel Aviv (IL); Galina Rodionov, Yavne (IL)

(73) Assignee: CureTech Ltd., Yavne (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/264,338

(22) Filed: Apr. 29, 2014

(65) Prior Publication Data

US 2014/0302032 A1 Oct. 9, 2014

Related U.S. Application Data

(62) Division of application No. 12/867,208, filed as application No. PCT/IL2009/000153 on Feb. 11, 2009, now Pat. No. 8,747,847.

(60) Provisional application No. 61/027,501, filed on Feb. 11, 2008, provisional application No. 61/037,340, filed on Mar. 18, 2008, provisional application No. 61/116,319, filed on Nov. 20, 2008.

(51) Int. Cl.
| | |
|---|---|
| *A61K 39/395* | (2006.01) |
| *C07K 16/18* | (2006.01) |
| *C07K 16/30* | (2006.01) |
| *A61K 31/282* | (2006.01) |
| *A61K 31/337* | (2006.01) |
| *A61K 31/513* | (2006.01) |
| *A61K 31/7068* | (2006.01) |
| *A61N 5/00* | (2006.01) |

(52) U.S. Cl.
CPC .............. *C07K 16/18* (2013.01); *A61K 31/282* (2013.01); *A61K 31/337* (2013.01); *A61K 31/513* (2013.01); *A61K 31/7068* (2013.01); *A61K 39/39558* (2013.01); *A61N 5/00* (2013.01); *C07K 16/3061* (2013.01)

(58) Field of Classification Search
None
See application file for complete search history.

(56) References Cited

U.S. PATENT DOCUMENTS

| | | |
|---|---|---|
| 5,225,539 A | 7/1993 | Winter |
| 5,897,862 A | 4/1999 | Hardy et al. |
| 6,217,866 B1 | 4/2001 | Schlessinger et al. |
| 6,811,779 B2 | 11/2004 | Rockwell et al. |
| 7,595,048 B2 | 9/2009 | Honjo et al. |
| 8,728,474 B2 | 5/2014 | Honjo et al. |
| 2003/0026800 A1 | 2/2003 | Hardy et al. |
| 2005/0180969 A1 | 8/2005 | Hardy et al. |
| 2006/0099209 A1 | 5/2006 | Hardy et al. |
| 2008/0025980 A1 | 1/2008 | Hardy et al. |

FOREIGN PATENT DOCUMENTS

| | | |
|---|---|---|
| WO | 00/58363 A1 | 10/2000 |
| WO | 03/012105 A2 | 2/2003 |
| WO | 03/099196 A2 | 12/2003 |
| WO | WO/03/099196 | * 12/2003 |
| WO | 2006/021955 A2 | 3/2006 |
| WO | WO/2006/021955 | * 3/2006 |
| WO | 2007/113648 A2 | 10/2007 |

OTHER PUBLICATIONS

Ferrante et al. (Cancer Chemother. Pharmacol., vol. 43(Suppl), p. S61-S68, 1999).*
Berger et al., "Phase I Safety and Pharmacokinetic Study of CT-011, a Humanized Antibody Interacting with PD-1, in Patients with Advanced Hematologic Malignancies," Clin Cancer Res 14(10):3044-3051 (May 2008).
Chothia et al., "Domain Association in Immunoglobulin Molecules. The Packing of Variable Domains," J. Mol. Biol. 186(3):651-663 (1985).
Fang et al., "Human Rheumatoid Factors with Restrictive Specificity for Rabbit Immunoglobulin G: Auto- and Multi-reactivity, Diverse VH Gene Segment Usage and Preferential Usage of VλIIIb," The Journal of Experimental Medicine 179:1445-1456 (May 1994).
Feinmesser et al., "Prevention of melanoma metastases in lungs of BAT treated and peptide immunized mice," International Journal of Oncology 29:911-917 (2006).
Ferrante et al., "Promising new developments in cancer chemotherapy," Cancer Chemother Pharmacol 43(Suppl):S61-S68 (1999).
Hardy et al., "A Monoclonal Antibody against a Human B Lymphoblastoid Cell Line Induces Tumor Regression in Mice," Cancer Research 54(22):5793-5796 (Nov. 1994).
Hardy et al., "Immune stimulatory and anti-tumor properties of anti-CD3 and BAT monoclonal antibodies: A comparative study," Human Antibodies 8(2):95-98 (1997).

(Continued)

*Primary Examiner* — Laura B Goddard
*Assistant Examiner* — Meera Natarajan
(74) *Attorney, Agent, or Firm* — Winston & Strawn LLP

(57) ABSTRACT

A method of treating a tumor or enhancing survival of a subject having a tumor. The method includes (i) administering to a subject in need thereof an effective amount of a humanized monoclonal antibody or a fragment thereof, wherein the antibody or the fragment thereof has all complementarity determining regions of murine monoclonal antibody BAT (mBAT-1) and a framework region (FR) from an acceptor human immunoglobulin, or modified therefrom; and (ii) administering to the subject an effective amount of at least one chemotherapeutic agent selected from the group consisting of: 5-fluorouracil, cytarabine, oxaliplatin, paclitaxel and combinations thereof. The humanized antibody is administered between 1 and 30 days after commencing chemotherapy or substantially simultaneously or concurrently or according to an overlapping schedule with the at least one chemotherapeutic agent to thereby treat the tumor or enhance the survival of the subject having the tumor.

20 Claims, 20 Drawing Sheets

(56) References Cited

OTHER PUBLICATIONS

Hardy et al., "A lymphocyte-activating monoclonal antibody induces regression of human tumors in severe combined immunodeficient mice," Proc. Natl. Acad. Sci. USA 94(11):5756-5760 (May 1997).

Hardy et al., "Treatment with BAT monoclonal antibody decreases tumor burden in a murine model of leukemia/lymphoma," International Journal of Oncology 19(5):897-902 (2001).

Hardy et al., "BAT monoclonal antibody immunotherapy of human metastatic colorectal carcinoma in mice," Cancer Letters 229(2):217-222 (2005).

Hardy et al., "BAT mAb induces lymphopoiesis in nude mice," International Immunology 17(5):615-619 (2005).

Marks et al., "By-passing Immunization. Human Antibodies from V-gene Libraries Displayed on Phage," J. Mol. Biol. 222(3):581-597 (1991).

Novotny, "Structural invariants of antigen binding: Comparison of immunoglobulin VL-VH and VL-VL domain dimers," Proc. Natl. Acad. Sci. USA 82(14):4592-4596 (Jul. 1985).

Quaglino et al., "The adjuvant activity of BAT antibody enables DNA vaccination to inhibit the progression of established autochthonous Her-2/neu carcinomas in BALB/c mice," Vaccine 23(25):3280-3287 (2005).

Raiter et al., "CD4+ T lymphocytes as a primary cellular target for BAT mAb stimulation," International Immunology 12(11):1623-1628 (2000).

Wada et al., "Combination therapy of interferon-α and 5-fluorouracil inhibits tumor angiogenesis in human hepatocellular carcinoma cells by regulating vascular endothelial growth factor and angiopoietins," Oncology Reports 18:801-809 (2007).

International Search Report and Written Opinion, Appl. No. PCT/IL2009/000153, Jun. 8, 2009.

\* cited by examiner

```
CDRs Kabat NO                                          ===L1====                              ==L2===
         SEQ ID NO.
                                    1         2         3         4         5         6         7
                          1234567890123456789012345678901234567890123456789012345678901234567890

Mouse BATVk    129        QIVLTQSPAIMSASPGEKVTITCSARSSVSYMHWFQQKPGTSPKLWIYRTSNLASGVPARFSGSGSGTSY
Human TEL9Vk   130        E.......SSL...V.DR.....R.SQSISN.LN.Y.....KA...L..AA.T.Q.....S......D
Variants
BATRk_A        15         EIVLTQSPSSLSASVGDRVTITCSARS-SVSYMHWYQQKPGKAPKLLIYRTSNLASGVPSRFSGSGSGTD
BATRk_B        16         EIVLTQSPSSLSASVGDRVTITCSARS-SVSYMHWFQQKPGKAPKLWIYRTSNLASGVPSRFSGSGSGTD
BATRk_C        17         EIVLTQSPSSLSASVGDRVTITCSARS-SVSYMHWFQQKPGKAPKLWIYRTSNLASGVPSRFSGSGSGTD
BATRk_D        18         EIVLTQSPSSLSASVGDRVTITCSARS-SVSYMHWFQQKPGKAPKLWIYRTSNLASGVPSRFSGSGSGTS CDRs Kabat NO                              ===L3====
         SEQ ID NO                 8         9         10
                          12345678901234567890123456789012334567

Mouse BATVk    129        CLTISRMEAEDAATYYCQQRSSFPLTFGSGTKLEIK
Human TEL9V    130        FT...NSLQP..F......TN.......G........
Variants
BATRk_A        15         FTLTINSLQPEDFATYYCQQRSSFPLTFGGGTKLEIK
BATRk_B        16         YTLTINSLQPEDFATYYCQQRSSFPLTFGGGTKLEIK
BATRk_C        17         YCLTINSLQPEDFATYYCQQRSSFPLTFGGGTKLEIK
BATRk_D        18         YCLTINSLQPEDFATYYCQQRSSFPLTFGGGTKLEIK
```

```
CDRs Kabat Numbers
                              -----=B1=                                 ==========H2==========
            1234567890123456789012345678901234567890123A4567890123456789012345678901234567890123456
                      1         2         3         4         5         6         7
Mouse  BATVH    QIQLVQSGPELKKPGETVKISCKASGYTFTNYGMNWVKQAPGKGLKWMGWINTDSGESTYAEFFKGRFAFSLETSAN
(SEQ ID NO: 145)
hsighv 1295 VH  .V.........AS........S.SSHAI....R....Q..Q........NT.SP...QG.T...V...D..VS
(SEQ ID NO: 146)
Variant SEQ ID NO.
BATRHA    20    QVQLVQSGSELKKPGASVKISCKASGYSFSNYGMNWVRQAPGQGLQWMGWINTDSGESTYAEEFKGRFVFSLDTSVS
BATRHB    21    QVQLVQSGSELKKPGASVKISCKASGYTFTNYGMNWVRQAPGQGLQWMGWINTDSGESTYAEEFKGRFVFSLDTSVS
BATRHC    22    QVQLVQSGSELKKPGASVKISCKASGYTFTNYGMNWVRQAPGQGLQWMGWINTDSGESTYAEEFKGRFVFSLDTSVN
BATRHD    23    QIQLVQSGSELKKPGASVKISCKASGYTFTNYGMNWVRQAPGQGLQWMGWINTDSGESTYAEEFKGRFVFSLDTSVN
BATRHE    24    QIQLVQSGSELKKPGASVKISCKASGYTFTNYGMNWVKQAPGQGLKWMGWINTDSGESTYAEEFKGRFAFSLDTSVN CDRs Kabat Numbers                    ======H3======
            789012ABC34567890123456789 0ABC1234567890123
                  8         9        10        11
Mouse  BATVH    TAYLQINNLNNEDTATYFCVRVGYDAL---DYWGQGTSVTVSS
(SEQ ID NO: 145)
hsighv 1295 VH  ......TS.TA...GM...AKESHSSA LDL........L........
(SEQ ID NO: 146)
Variant SEQ ID NO.
BATRHA    20    TAYLQITSLTAEDTGMYFCAKVGYDAL---DYWGQGTLVTVSS
BATRHB    21    TAYLQITSLTAEDTGMYFCAKVGYDAL---DYWGQGTLVTVSS
BATRHC    22    TAYLQITSLTAEDTGMYFCVRVGYDAL---DYWGQGTLVTVSS
BATRHD    23    TAYLQITSLTAEDTGMYFCVRVGYDAL---DYWGQGTLVTVSS
BATRHE    24    TAYLQITSLNAEDTGMYFCVRVGYDAL---DYWGQGTLVTVSS
```

MONOCLONAL ANTIBODIES FOR TUMOR TREATMENT

CROSS-REFERENCE TO RELATED APPLICATIONS

This application is a continuation of U.S. application Ser. No. 12/867,208 filed Sep. 8, 2010, which is the National Phase of PCT/IL2009/000153 filed Feb. 11, 2009, and which claims the benefit of U.S. provisional applications nos. 61/027,501 filed Feb. 11, 2008, 61/037,340 filed Mar. 18, 2008 and 61/116,319 filed Nov. 20, 2008, the entire content of each of which is expressly incorporated herein by reference thereto.

FIELD OF THE INVENTION

The present invention relates to methods for inhibiting tumor growth, increasing survival of a subject having a tumor and inducing protection against tumor recurrence in a mammal. The methods comprise administering a humanized monoclonal antibody comprising CDR regions derived from the murine monoclonal antibody designated mBAT-1, in combination with at least one chemotherapeutic agent.

BACKGROUND OF THE INVENTION

The rapid increase of knowledge in recent years about the molecular and cellular bases of immune regulation, particularly at the level of T cell responses, provides a new arsenal of immunotherapeutic approaches including the development of tumor vaccines. Certain monoclonal antibodies were shown to have immunomodulatory activity including the ability to bind determinants on the surface of T cells and to induce proliferation, activation, maturation or differentiation of these cells.

BAT (also referred to as mBAT-1 or BAT-1) is a murine monoclonal antibody generated against a membrane preparation of a Burkitt lymphoma cell line (Daudi) that was shown to exhibit antitumor and immunostimulatory effects towards various types of tumors (Hardy et al., 2001, Int. J. Oncol. 19:897). This monoclonal antibody was initially disclosed in U.S. Pat. No. 5,897,862 to Hardy et al. BAT-1 is secreted by the hybridoma cell line having CNCM Accession No. 1-1397.

The polynucleotide and amino-acid sequences of murine BAT are disclosed in WO 00/58363, to Hardy et al., and U.S. Patent Publication No. 2003/0026800. A number of humanized monoclonal antibodies based on murine BAT are disclosed in U.S. Patent Application Publication No. 2008/0025980. According to the disclosure, the humanized monoclonal BAT antibody appears to induce a greater antitumor effect than those induced by the parent murine BAT antibody. Among various model systems tested, the BAT antitumor activity was studied in SCID (severe combined immunodeficiency disease) mice, beige mice that are deficient in NK cells and nude mice that are deficient in T cells (Hardy, B., 1997, Proc. Natl. Acad. Sci. USA 94:5756). All mice were injected intravenously with murine B16 melanoma that subsequently develops tumors in the lungs. BAT exerted an antitumor effect only in SCID mice that were engrafted with either murine or human lymphocytes. In the athymic nude mice and the beige mice BAT exerted an antitumor activity, though this activity was less effective as compared to the antitumor activity of BAT in the wild-type mice.

The immunomodulatory effect of murine BAT was studied also in vitro. Murine BAT activates CD4+ T cells and induces the secretion of IFN-γ from these cells (Hardy et al., 2000, Int. Immunol. 12:1623 and Quaglino E. et al., 2005, Vaccine 9:23(25):3280-7, respectively). In addition, it was found that BAT triggers the proliferation of T cells and increases their cytolytic activity (Hardy, B. et al., 1997, Hum. Antibodies, 8:95).

Berger et al. (2008) discloses administration of the humanized monoclonal antibody CT-011, which is based on mBAT-1, to patients with advanced hematologic malignancies, and associated pharmacokinetics (Berger et al. Clin. Cancer Res. 2008; 14 (10) May 15, 2008).

It should be borne in mind that BAT antibodies are not expected to target the tumor cells themselves but rather the immune-functioning cells of the subject or patient, in order to modulate the immune response in a beneficial way.

One of the most widely used therapeutic treatments of cancer is chemotherapy. Chemotherapy drugs are divided into several groups based on their effect on specific chemical substances within cancer cells, the cellular activities or processes the drug interferes with, or the specific phases of the cell cycle the drug affects. Chemotherapy groups include: alkylating agents, nitrosoureas, antimetabolites, anthracyclines, topoisomerase I and II inhibitors, mitotic inhibitors and steroid inhibitors.

A chemotherapeutic drug may be provided as a sole therapy but is often used in combination with one or more other active agents. In some instances, specific combinations have been adapted to provide significantly better clinical results. For example, the antimetabolite fluorouracil (5FU) and the alkylating agent oxaliplatin, are used together in a combination regimen for the treatment of colorectal cancer. The combination therapy of fluorouracil, leucovorin (folinic acid) and oxaliplatin, also indicated for colorectal cancer, has been abbreviated as FOLFOX. The combination therapy of cyclophosphamide, doxorubicin, vincristine and predinisone (abbreviated as CHOP) is used for the treatment of non-Hodgkin lymphoma, and the combination of CHOP and the chimeric monolclonal antibody rituximab (abbreviated as R-CHOP) is used for the treatment of diffuse large B cell lymphoma and other aggressive B-cell non-Hodgkin lymphomas.

A combination therapy of uracil, 5FU or uracil mustard with radiation and with a monoclonal antibody, which specifically binds to an extracellular domain of a VEGF receptor, is disclosed in U.S. Pat. No. 6,811,779. This combined therapy is directed to inhibit angiogenesis. U.S. Pat. No. 6,217,866 discloses a method for inhibiting the growth of human tumor cells that express human EGF receptors comprising administering an effective amount of an anti-neoplastic agent and an effective amount of a monoclonal antibody to a human cancer patient having said tumor cells; (i) wherein said antibody binds to the extra-cellular domain of the human EGF receptor of said tumor cell; (ii) wherein the antibody is not conjugated to the anti-neoplastic agent; and (iii) wherein the antibody inhibits the binding of EGF to the EGF receptor.

Nowhere in the background art is it taught or suggested that use of a humanized mBAT-1 monoclonal antibody in combination with chemotherapy will be advantageous. In fact, since BAT and antibodies based thereon are known to have immunomostimulatory properties, it is highly surprising and unexpected that such antibodies in combination with cytotoxic or other chemotherapeutic drugs that act by killing proliferating cell populations can be used to achieve greater clinical efficacy than each type of agent on its own.

SUMMARY OF THE INVENTION

The present invention provides methods for inhibiting tumor growth, reducing tumor volume, increasing survival of a subject and inducing protection against tumor recurrence in subjects bearing solid and non-solid tumors. The methods comprise use of a humanized monoclonal antibody having at least one complementarity determining region (CDR) of murine monoclonal antibody BAT-1 (mBAT-1) and a framework region (FR) derived from an acceptor human immunoglobulin. An example of such an antibody is hBAT-1 (also referred to herein as CT-011). Some of the methods disclosed herein preferably comprise use of the humanized monoclonal antibody in a combination regimen with at least one chemotherapeutic agent, whereas other methods disclosed herein relate to use of the humanized monoclonal antibody on its own, but which can optionally be employed in combination with one or more chemotherapeutic agents.

The principles of the invention are demonstrated herein using both mBAT-1 and CT-011 in lymphocyte cultures and in animal tumor models, and CT-011 in human patients having various types of hematologic tumors.

The invention is based, in part, on the unexpected discovery that the incorporation of CT-011 to a treatment regimen with various chemotherapeutic agents results in several beneficial antitumor and anticancer effects, including for example, reduction in the rate of tumor growth, inhibition of tumor growth, and increased survival time, as compared to monotherapies with either of the treatments alone. It has also been found that incorporation of a humanized antibody such as CT-011 into a chemotherapy regimen can provide the additional benefit of increased tolerability to dose-limiting toxicity (DLT) levels of a chemotherapeutic agent.

The invention is also based, in part, on the observation that treatment of induced tumors in animal models with the subject antibodies, either alone or in combination with a chemotherapeutic agent, results in both a "cure", as well as a memory effect for long-term protection against tumor recurrence upon subsequent challenge with the same tumor cells. Animals cured by treatment with the humanized antibody CT-011 were thus rendered resistant to recurrence or re-exposure to the tumor. Furthermore, it is now disclosed that in certain instances human subjects undergoing early stage clinical trials with CT-011 also demonstrate long-term tumor control and protection effects after the administration of a single dose of this antibody and its elimination from the blood.

Without wishing to be bound by any theory or mechanism of action, the activity of humanized BAT monoclonal antibody in protecting against tumor recurrence or resurgence may be associated with the activity of such an antibody in protecting effector/memory T cells from apoptosis, as disclosed herein and exemplified with antibody CT-011.

Thus, in various aspects, the present invention provides combinations of antitumor agents that are not hitherto known to exert a cumulative or even an additive effect. According to certain principles of the invention, the combinations comprise one treatment which is administration of at least one chemotherapeutic agent, and another different treatment which is administration of an immunostimulatory humanized monoclonal antibody based on mBAT-1. Unexpectedly, the two treatments achieve a greater beneficial antitumor effect when used in combination, than when used separately or each on its own. Combination therapy as used herein and in the claims may refer to any of a number of different combination treatments, including for example, substantially overlapping periods of administration of two or more treatments; simultaneous, sequential or successive administration of two or more treatments, or scheduled administration of two or more treatments during alternating time periods.

According to a first aspect, the present invention provides a method of treating a tumor, the method comprising (i) administering to a subject in need thereof an effective amount of a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom; and (ii) administering to the subject an effective amount of at least one chemotherapeutic agent; thereby treating the tumor.

According to another aspect, the invention further provides a method of improving tolerability to at least one chemotherapeutic agent, the method comprising administering to a subject in need thereof an effective amount of a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom; wherein the subject is undergoing chemotherapy with at least one chemotherapeutic agent; thereby improving tolerability to said chemotherapeutic agent.

According to yet another aspect of the invention, there is provided a method of enhancing survival or inhibiting disease progression in a subject having a tumor, wherein the subject is treated with at least one chemotherapeutic agent, the method comprising administering an effective amount of a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom; thereby enhancing survival of the subject.

According to yet another aspect, the invention provides a method of reducing or preventing tumor recurrence, the method comprising administering to a subject in need thereof an effective amount of a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom; thereby reducing or preventing tumor recurrence.

According to one embodiment, the method of reducing or preventing tumor recurrence further comprises administering to the subject at least one chemotherapeutic agent.

According to particular embodiments, the subject is undergoing or has completed a course of chemotherapy with at least one chemotherapeutic agent.

According to various embodiments, the light chain variable region of the humanized monoclonal antibody is characterized by the formula:

$FR_{L1}\text{-}CDR_{L1}\text{-}FR_{L2}\text{-}CDR_{L2}\text{-}FR_{L3}\text{-}CDR_{L3}\text{-}FR_{L4}$ wherein each FR is independently a framework region of a human antibody and each CDR is independently a complementarity determining region of the monoclonal mBAT-1 antibody.

According to various embodiments, the heavy chain variable region of the humanized monoclonal antibody is characterized by the formula:

$FR_{H1}\text{-}CDR_{H1}\text{-}FR_{H2}\text{-}CDR_{H2}\text{-}FR_{H3}\text{-}CDR_{H3}\text{-}FR_{H4}$ wherein each FR is independently a framework region of a human antibody and each CDR is independently a complementarity determining region of the monoclonal mBAT-1 antibody.

According to various embodiments, the FRs are derived from the light chain variable region of the human TEL9 antibody (SEQ ID NO: 130), or modified therefrom.

According to various embodiments, the FR amino acid sequences derived or modified from the light chain variable region of the human TEL9 antibody are selected from the group consisting of: $FR_{L1}$, [EIVLT QSPSS LSASV GDRVT ITC; SEQ ID NO: 1]; $FR_{L2}$, [W (F or Y) QQKPG KAPKL (W or L) IY; SEQ ID NO: 2]; $FR_{L3}$, [GVPSR FSGSG SGT (D or S) (Y or F) (C or T) LTINS LQPED FATYY C; SEQ ID NO: 3]; and $FR_{L4}$, [FGGGT KLEIK; SEQ ID NO: 4].

According to various embodiments, the FRs are derived from the heavy chain variable region of the human hsighv1295 antibody (SEQ ID NO: 146), or modified therefrom.

According to various embodiments, the FR amino acid sequences derived or modified from the heavy chain variable region of the human hsighv1295 antibody are selected from the group consisting of: $FR_{H1}$, [Q (I or V) QLV QSGSE LKKPG ASVKI SCKAS GY (T or S) F (T or S); SEQ ID NO: 5]; $FR_{H2}$, [WV (R OR K) QAPGQ GL (Q or K) WMG; SEQ ID NO: 6]; $FR_{H3}$, [RF (V or A) FSLDT SV (N or S) TAYLQ ITSL (T or N) AEDTG MYFC (V or A) (R or K); SEQ ID NO: 7]; and $FR_{H4}$, [WGQGT LVTVS S; SEQ ID NO: 8].

According to various embodiments, the light chain variable region comprises at least one amino acid sequence selected from the group consisting of: $CDR_{L1}$ [SARSS VSYMH; SEQ ID NO: 9]; $CDR_{L2}$ [RTSNL AS; SEQ ID NO: 10]; $CDR_{L3}$ [QQRSS FPLT; and SEQ ID NO: 11], wherein the CDRs are derived from the murine BAT-1 antibody and the subscripts "L" and "H" refer to light and heavy chain regions, respectively.

According to various embodiments, the heavy chain variable region comprises at least one amino acid sequence selected from the group consisting of: $CDR_{H1}$ [NYGMN; SEQ ID NO: 12]; $CDR_{H2}$ [WINTD SGEST YAEEF KG; SEQ ID NO: 13]; and $CDR_{H3}$ [VGYDA LDY; SEQ ID NO: 14].

According to various embodiments, the humanized antibody comprises: a light chain variable region selected from the group consisting of: $BATR\kappa_A$ (SEQ ID NO: 15), $BATR\kappa_B$ (SEQ ID NO: 16), $BATR\kappa_C$ (SEQ ID NO: 17), and $BATR\kappa_D$ (SEQ ID NO: 18); and a heavy chain variable region selected from the group consisting of: A (SEQ ID NO: 20), $BATRH_B$ (SEQ ID NO: 21), $BATRH_C$ (SEQ ID NO: 22), $BATRH_D$ (SEQ ID NO: 23) and $BATRH_E$ (SEQ ID NO: 24).

According to yet other embodiments, the humanized antibody comprises variable regions selected from the group consisting of: $BATRH_A/BATR\kappa_A$ (SEQ ID NO: 20/SEQ ID NO: 15), $BATRH_B/BATR\kappa_A$ (SEQ ID NO: 21/SEQ ID NO: 15), $BATRH_B/BATR\kappa_B$ (SEQ ID NO: 21/SEQ ID NO: 16), $BATRH_C/BATR\kappa_B$ (SEQ ID NO: 22/SEQ ID NO: 16), $BATRH_B/BATR\kappa_D$ (SEQ ID NO: 21/SEQ ID NO: 18), and $BATRH_C/BATR\kappa_D$ (SEQ ID NO: 22/SEQ ID NO: 18).

According to various preferred embodiments, the humanized monoclonal antibody has variable regions corresponding to $BATRH_C/BATR\kappa_D$ (SEQ ID NO: 22/SEQ ID NO: 18).

According to various embodiments, the antitumor activity of the humanized antibody or a fragment thereof is similar or greater than mBAT-1.

According to various embodiments, the fragment of the humanized antibody is selected from the group consisting of: Fv, F (ab'), F (ab') 2, and a single chain antibody.

The humanized monoclonal antibody of the invention is preferably generated by recombinant DNA technology, utilizing CDR grafting. Accordingly, the humanized antibody is produced by expression of polynucleotides, wherein the polynucleotides may encode the whole humanized antibody or the light chain variable region or the heavy chain variable region or the variable region of both chains of the humanized antibody. Further, the humanized antibody may be expressed in a host cell following co-transfection of distinct vectors each comprising polynucleotides encoding the heavy or the light chain, or by transfection of a single vector comprising both light and heavy chain polynucleotide sequences.

According to various embodiments, the light chain of the humanized antibody is encoded by a polynucleotide sequence selected from the group consisting of: SEQ ID NO: 87, SEQ ID NO: 88, and SEQ ID NO: 89.

According to various embodiments, the heavy chain of the humanized antibody is encoded by a polynucleotide sequence selected from the group consisting of: SEQ ID NO: 90, SEQ ID NO: 91, and SEQ ID NO: 92.

According to various embodiments, the at least one chemotherapeutic agent is selected from the group consisting of: antimetabolites, platinum-based drugs, mitotic inhibitors, anthracycline antibiotics, topoisomerase inhibitors, anti-angiogenic agents and combinations thereof.

According to a currently preferred embodiment, the at least one chemotherapeutic agent is selected so that hBAT-1 enhances survival of lymphocytes when used in combination with the chemotherapeutic agent. Typically, the enhanced or increased survival may be conveniently assayed in vitro, as exemplified hereinbelow.

According to some embodiments, the at least one chemotherapeutic agent is an antimetabolite, including purine antagonists, pyrimidine antagonists and folate antagonists. According to some embodiments, the antimetabolite is a pyrimidine antagonist. According to some embodiments, the antimetabolite is selected from the group consisting of: 5-fluorouracil, uracil mustard, uracil, capecitabine, 6-mercaptopurine, methotrexate, gemcitabine, cytarabine, fludarabine, and pemetrexed.

According to some embodiments, the at least one chemotherapeutic agent is 5-fluorouracil.

According to some embodiments, the at least one chemotherapeutic agent is cytarabine.

According to some embodiments, the at least one chemotherapeutic agent is a platinum-based drug selected from the group consisting of: cisplatin, carboplatin and oxaliplatin.

According to yet other embodiments, the at least one chemotherapeutic agent is a mitotic inhibitor selected from the group consisting of: paclitaxel, docetaxel, etoposide, vinblastine, vincristine and vinorelbine.

According to yet other embodiments, the at least one chemotherapeutic agent is an anthracycline antibiotic selected from the group consisting of: daunorubicin, respinomycin D and idarubicin.

According to some embodiments, the at least one chemotherapeutic agent is an anti-angiogenic agent selected from the group consisting of: bevacizumab, dopamine, tetrathiomolybdate, and antiangiogenic variants of VEGF.

According to some embodiments, the at least one chemotherapeutic agent is other than a topoisomerase I inhibitor. According to some embodiments, the at least one chemotherapeutic agent is other than an alkylating agent.

According to various embodiments, the administering of the humanized antibody and of the at least one chemotherapeutic agent is carried out substantially simultaneously, concurrently, alternately, sequentially or successively. In some embodiments, the humanized antibody and the at least one chemotherapeutic agent are administered according to overlapping schedules.

According to particular embodiments, administering of the humanized antibody is carried out prior to initial administration of the at least one chemotherapeutic agent.

According to other embodiments, administering of either or both of the humanized antibody and the at least one chemotherapeutic agent is carried out by a route selected from the group consisting of intravenous, oral, intraperitoneal, subcutaneous, isolated limb perfusion, infusion into an organ and combinations thereof.

According to various embodiments, the methods further comprise treating the subject with radiation. According to various embodiments, the methods comprise all of administering the humanized antibody, administering the at least one chemotherapeutic agent and treating the subject with radiation.

According to some embodiments, the humanized antibody, the at least one chemotherapeutic agent and radiation treatment are administered substantially simultaneously, concurrently, alternately, successively or according to overlapping schedules.

In particular embodiments, the methods of the invention further comprise assessing at least one parameter selected from the group consisting of: rate of tumor growth, tumor volume, number of metastases, tumor recurrence and combinations thereof.

In some embodiments, the tumor is a solid or a non-solid tumor. In some embodiments, the non-solid tumor is a hematologic malignancy. In particular embodiments, the tumor is selected from the group consisting of a colorectal carcinoma tumor; a non-small lung cancer (NSCLC) tumor; a small cell lung cancer (SCLC) tumor; a breast carcinoma tumor; a melanoma tumor; an ovarian carcinoma tumor; a cervical carcinoma tumor; a pancreatic cancer tumor; a head and neck carcinoma tumor; a gastrointestinal carcinoma tumor; an esophageal tumor; a hepatocellular carcinoma tumor; multiple myeloma; a renal cell carcinoma tumor; a prostate tumor; non-Hodgkin's lymphoma; Hodgkin's disease; mantle cell lymphoma; Kaposi's sarcoma; a squamous cell carcinoma tumor; a basal cell carcinoma tumor; acute myeloid leukemia (AML); chronic myelocytic leukemia (CML); acute lymphocytic leukemia (ALL), and chronic lymphocytic leukemia (CLL).

According to various embodiments, the subject is a human or non-human mammal. According to various preferred embodiments, the subject is a human.

In an additional aspect, the invention provides use of (i) a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom; and (ii) at least one chemotherapeutic agent; for the preparation of a medicament for treating a tumor.

In another aspect, the invention provides a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom; for the treatment of a tumor in a subject undergoing chemotherapy with at least one chemotherapeutic agent.

In an additional aspect, the invention provides use of a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom, for the preparation of a medicament for improving tolerability to at least one chemotherapeutic agent in a subject undergoing chemotherapy with said at least one chemotherapeutic agent.

In an additional aspect, the invention provides a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom, for improving tolerability to at least one chemotherapeutic agent in a subject undergoing chemotherapy with said at least one chemotherapeutic agent.

According to another aspect, the invention provides use of a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom; for the preparation of a medicament for enhancing survival or inhibiting disease progression in a subject having a tumor, wherein the subject is treated with at least one chemotherapeutic agent.

According to another aspect, the invention provides a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom; for enhancing survival or inhibiting disease progression in a subject having a tumor, wherein the subject is treated with at least one chemotherapeutic agent.

According to yet another aspect, the invention provides use of a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom; for the preparation of a medicament of reducing or preventing recurrence of a tumor.

According to yet another aspect, the invention provides a humanized monoclonal antibody or a fragment thereof, wherein the antibody or the fragment thereof has at least one complementarity determining region of murine monoclonal antibody BAT (mBAT-1) and a framework region (FR) from an acceptor human immunoglobulin, or modified therefrom; for reducing or preventing recurrence of a tumor.

In particular embodiments, the subject has undergone, is undergoing, or is scheduled to undergo chemotherapy with at least one chemotherapeutic agent.

BRIEF DESCRIPTION OF THE DRAWINGS

FIG. 1A. hBAT-1 (0.5 or 0.75 ug/ml as indicated) activity in the absence and presence of 5FU, presented as % difference in cell survival. FIG. 1B. hBAT-1 (0.75 ug/ml) activity in the absence and presence of 5FU, expressed by Area Under dose response Curve (AUC presented as % difference×ug/ml). The incubation time with hBAT-1 (72 hours) is indicated on the x-axis. FIG. 1C. The effect of 5FU or vehicle control in the functional assay presented as viable cells/ml. The incubation time with 5FU or vehicle control (72 hours) is indicated on the x-axis.

FIG. 2A. hBAT-1 (0.5 or 0.75 ug/ml as indicated) activity in the absence and presence of 5FU, presented as % difference in cell survival. FIG. 2B. hBAT-1 (0.75 ug/ml) activity in the absence and presence of 5FU, presented as Area Under a dose response Curve (AUC presented as % difference×ug/ml). The incubation time with hBAT-1 (72 hours) is indicated on the x-axis.

FIG. 3A. hBAT-1 (0.5 or 0.75 ug/ml as indicated) activity in the absence and presence of SN-38, presented as % difference in cell survival. FIG. 3B. hBAT-1 (0.75 ug/ml) activity expressed by Area Under dose response Curve (AUC presented as % difference×ug/ml). The incubation time with hBAT-1 (72 hours) is indicated on the x-axis.

FIG. 4A. hBAT-1 (0.5 or 0.75 ug/ml as indicated) activity in the absence and presence of SN-38, presented as % difference in cell survival. FIG. 4B. hBAT-1 (0.75 ug/ml) activity expressed as Area Under a dose response Curve (AUC presented as % difference×ug/ml). The incubation time with hBAT-1 (72 hours) is indicated on the x-axis.

FIG. 19 shows the amino acid sequences of various embodiments of the humanized BAT-1 VK region (SEQ ID NOS. 15-18). Where the BAT-1 Vκ region residues and the human TEL9 Vκ region (SEQ ID NO. 130) sequence match a dot [.] is shown. Where no amino acid is present at a specific residue position a dash [–] is shown. Where an amino acid in the TEL9 FRs is changed in the humanized BAT-1 Vκ region, it is highlighted in bold. The CDRs are described by the use of the nomenclature [=L1=]. The numbering used is as according to Kabat (Kabat et al., Sequences of proteins of immunological interest, Fifth Edition, U.S. Department of Health and Human Services, U.S. Government Printing Office, 1991).

FIG. 20 presents the amino acid sequences of various embodiments of the humanized BAT-1 VH region (SEQ ID NOS. 20-24). Where the BAT-1 VH region residues and the human hsighv1295 VH region (SEQ ID NO. 146) sequence match a dot [.] is shown. Where no amino acid is present at a specific residue position a dash [-] is shown. Where an amino acid in the hsighv1295 FRs is changed in the humanized BAT-1 VH region, it is highlighted in bold. The CDRs are described by the use of the nomenclature [=H1=], while [-----] denotes part of the H1 structural loop. The numbering used is as according to Kabat (Kabat et al., ibid).

DETAILED DESCRIPTION OF THE INVENTION

Definitions

Figure 1A:
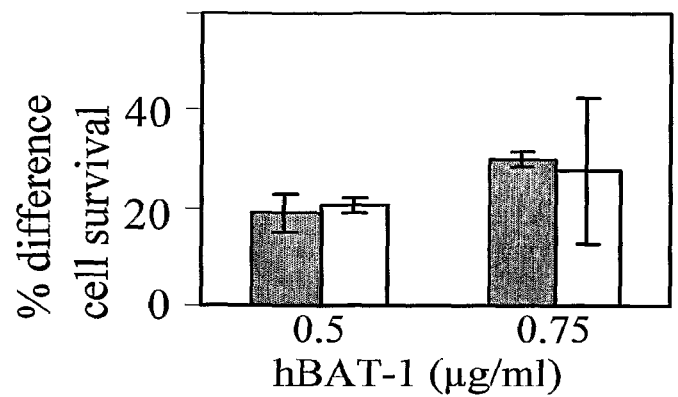
FIGS. 1A-1C show the effect of hBAT-1 in an assay based on viability of lymphocytes, when added to cultures concomitantly with vehicle control (gray bars) or in combination with 5FU (0.5 mg/ml, white bars) and incubated for 72 hours.
Figure 1B:
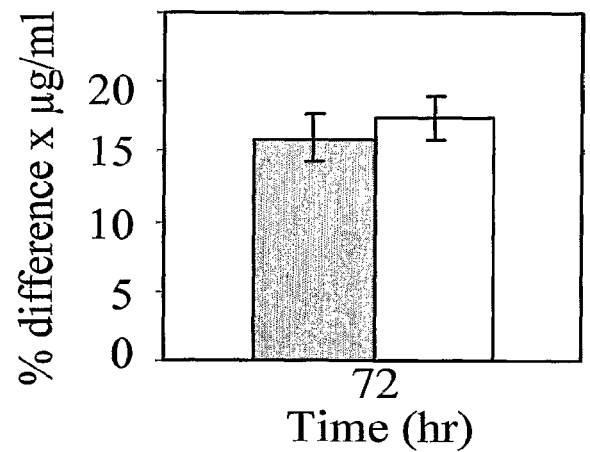

The term "antibody" (also referred to as an "immunoglobulin") is used in the broadest sense and specifically encompasses monoclonal antibodies (including full length monoclonal antibodies) and antibody fragments so long as they exhibit the desired biological activity. "Antibody fragments" comprise a portion of a full length antibody, generally the antigen binding or variable region thereof. Examples of antibody fragments include Fab, Fab', F(ab')2, and Fv fragments; diabodies; linear antibodies; single-chain antibody molecules; and multispecific antibodies formed from antibody fragments.

The basic unit of the naturally occurring antibody structure is a heterotetrameric glycoprotein complex of about 150,000 daltons, composed of two identical light (L) chains and two identical heavy (H) chains, linked together by both noncovalent associations and by disulfide bonds. Each heavy and light chain also has regularly spaced intrachain disulfide bridges. Five human antibody classes (IgG, IgA, IgM, IgD and IgE) exist, and within these classes, various subclasses, are recognized on the basis of structural differences, such as the number of immunoglobulin units in a single antibody molecule, the disulfide bridge structure of the individual units, and differences in chain length and sequence. The class and subclass of an antibody is its isotype.

The amino terminal regions of the heavy and light chains are more diverse in sequence than the carboxy terminal regions, and hence are termed the variable domains. This part of the antibody structure confers the antigen-binding specificity of the antibody. A heavy variable (VH) domain and a light variable (VL) domain together form a single antigen-binding site, thus, the basic immunoglobulin unit has two antigen-binding sites. Particular amino acid residues are believed to form an interface between the light and heavy chain variable domains (Chothia et al., J. Mol. Biol. 186, 651-63 (1985); Novotny and Haber, (1985) Proc. Natl. Acad. Sci. USA 82 4592-4596).

The carboxy terminal portion of the heavy and light chains form the constant domains i.e. CH1, CH2, CH3, CL. While there is much less diversity in these domains, there are differences from one animal species to another, and further, within the same individual there are several different isotypes of antibody, each having a different function.

The term "framework region" or "FR" refers to the amino acid residues in the variable domain of an antibody which are other than the hypervariable region amino acid residues as herein defined. The term "hypervariable region" as used herein refers to the amino acid residues in the variable domain of an antibody which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Rabat et al., ibid).

The term "acceptor human immunoblobulin" refers to the human immunoglobulin providing the framework for a humanized antibody.

As used herein, the term "humanized antibody" refers to an antibody comprising a framework region from a human antibody and one or more CDRs from a non-human (usually a mouse or rat) immunoglobulin. Parts of a humanized immunoglobulin, except possibly the CDRs, are substantially identical to corresponding parts of natural human immunoglobulin sequences. In some cases however, specific amino acid residues, for example in the framework regions, may be modified, so as to optimize performance of the humanized antibody. Importantly, the humanized antibody is expected to bind to the same antigen as the donor antibody that provides the CDRs. For further details, see e.g. U.S. Pat. No. 5,225,539 assigned to Medical Research Council, UK.

The terms "a framework region from an acceptor human immunoglobulin" and "a framework region derived from an acceptor human immunoblobulin", and similar grammatical expressions are used interchangeably herein to refer to a framework region or portion thereof that has the same amino acid sequence of the acceptor human immunoblobulin.

The term "a framework region modified from an acceptor human immunoglobulin" and similar grammatical expressions refers to a framework region that is altered in its amino acid sequence, for example by substitution or deletion or chemical modification of one or more amino acid residues, as compared to the sequence of the original acceptor human immunoblobulin. Modification in the FR region may be carried out so as to optimize performance of the humanized antibody being constructed, for example to optimize antigen binding and avoid steric clashes. A detailed explanation of the basis and rationale for modifying specific residues in the FR regions of an acceptor immunoglobulin for construction of a humanized BAT antibody is provided in U.S. Patent Application Publication No. 2008/0025980.

Further, an FR may be chemically modified at one or more amino acid residues, either by natural processes, such as processing or other post-translational modifications, or by chemical modification techniques. Chemical modifications include, without limitation, acetylation, acylation, amidation, ADP-ribosylation, glycosylation, GPI anchor formation, covalent attachment of a liquid or lipid derivative, methylation, myristylation, pegylation, prenylation, phosphorylation, ubiquitination, or any similar process.

The term "human antibody" refers to an antibody encoded by a gene actually occurring in a human, or an allele, variant or mutant thereof.

The term "antitumor effect" as used herein, refers to a beneficial biological effect, which can be manifested by any one or more of: a decrease or stabilization of tumor volume, a decrease or stabilization of the number of tumor cells, a decrease or stabilization of the rate of tumor growth, a decrease or stabilization of the number of metastases, protection from tumor recurrence, an increase in life expectancy or survival of the subject with the tumor, an increase in life expectancy or survival without disease progression of the subject with the tumor or amelioration of various physiological symptoms associated with the cancerous condition. An "antitumor effect" can also be manifested by the ability of the combination of the invention to prevent the occurrence of tumor in the first place or the recurrence of the tumor. Given its properties, the methods of the invention can be used in the treatment of acute cancer, of dormant, controlled or stabilized cancer, as well as in cancer prophylaxis.

The term "mammal" means any mammal, including pet animals, such as dogs and cats; farm animals, such as pigs, cattle, sheep, and goats; laboratory animals, such as mice and rats; primates, such as monkeys, apes, and chimpanzees; and preferably, humans.

The term "effective amount" with respect to the humanized antibody and the chemotherapeutic agent(s) of the invention should be understood as meaning an amount of each of these active agents required to achieve a therapeutic effect, without causing excessive or uncontrollable adverse side effects. The effective amount required to achieve the therapeutic end result may depend on a number of factors including, for example, the specific type of the tumor and the severity of the patient's condition, and whether the combination is further co-administered with radiation. The effective amount (dose) of the active agents, in the context of the present invention should be sufficient to effect a beneficial therapeutic response in the subject over time, including inhibition of tumor growth, reduction in the rate of tumor growth, prevention of tumor and metastasis growth and enhanced survival.

The term "enhanced survival", as used herein, refers to a prolonged length of time during which the subject or patient is alive following treatment with a method of the invention. Enhanced survival denotes the increased probability of staying free of disease progression for an individual suffering from cancer after a particular treatment. It is also used to describe the elevated percentage of individuals in a group whose disease is likely to remain stable (not showing signs of progression) after a specified duration of time, compared to a control group. It is also used to describe the elevated percentage of individuals in a group whose disease is likely to be cured (not showing signs of disease) after a specified duration of time, compared to a control group. This parameter may be measured by any one of the customary clinical endpoints denoted as "progression-free survival", "overall survival" and "disease free survival" used as an indication of the efficacy of a particular treatment.

The term "tolerability to chemotherapeutic agents" refers to the physiological, physicochemical and immunological capacity of a subject to tolerate the adverse side effects associated with treatment with one or more chemotherapeutic agents. Accordingly, the term "improving tolerability to chemotherapeutic agents" refers to increasing the physiological and physicochemical capacity to such adverse side effects, such that the severity of the adverse side effects is decreased and/or the number of side effects is decreased. Accordingly, "improving tolerability to chemotherapeutic agents" may refer to improving the quality of life of cancer patients treated with chemotherapeutic agents.

The term "tumor recurrence" refers to the re-emergence, reappearance, re-growth or proliferation of a tumor of the same type in either the same location or a different location, following a period during which the growth of the original tumor has been reversed, arrested or inhibited.

The term "enhances or increases lymphocyte survival" as used herein refers to the ability of a particular combination of treatments to prolong the viability of lymphocytes in vitro or in vivo, as compared to the viability of an identical cell population with only one of the treatments. For example, certain combinations of hBAT-1 and chemotherapeutic agents enhance lymphoctye survival, as assessed in an in vitro assay, as exemplified in Example 1 herein.

Methods of the Invention

Cancer immunotherapeutics are aimed by and large at modulating the response of the immune system to induce or enhance killing of tumor cells and control tumor growth. This approach utilizes using various immunomodulators including monoclonal antibodies that selectively bind to specific determinants on T cells thereby either initiating an activation pathway or inducing an inhibitory effect.

According to certain aspects of the present invention, administration of the immunostimulatory humanized antibody in conjunction with at least one antitumor chemotherapeutic agent acts to enhance the antitumor effect of chemotherapeutic agents, and vice versa. In preferred embodiments, the combinations of the immunostimulatory antibody together with the at least one chemotherapeutic agent improve the clinical outcome in a significant manner versus each of the treatments alone. In a preferred embodiment, there is synergy when tumors are treated with the humanized antibody of the invention in conjunction with at least one chemotherapeutic agent, and, optionally further in conjunction with radiation.

Figure 8:
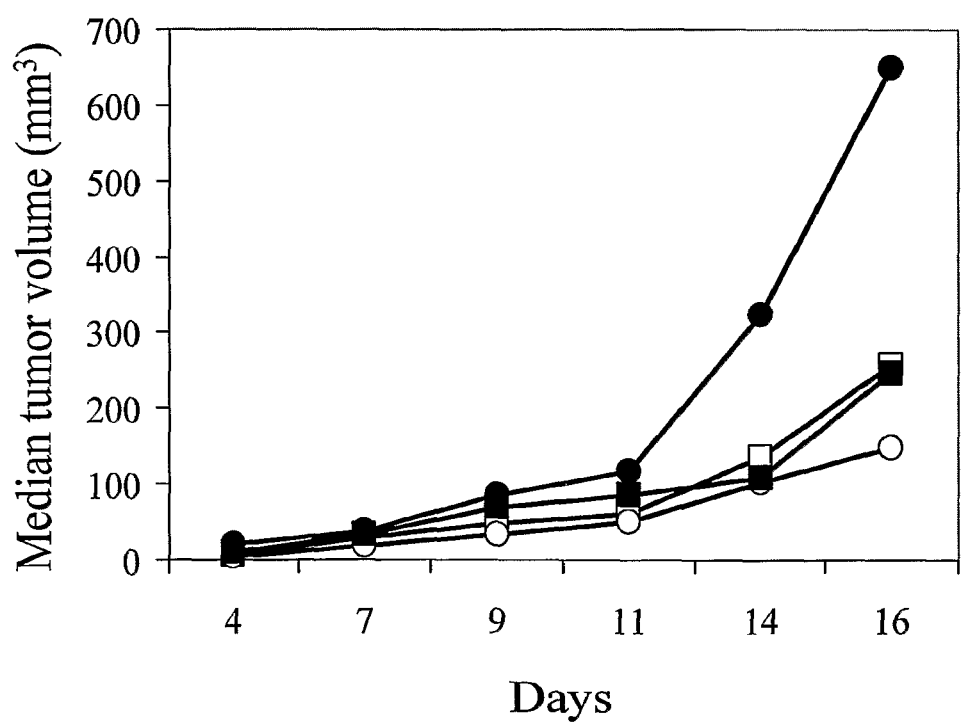
FIG. 8 shows the antitumor effect in colorectal adenocarcinoma (CRC) bearing mice of vehicle (black circles); 5FU (20 mg/kg administered on days 6-9 and 15-16; white squares); hBAT-1 (10 µg/mouse administered on day 10; black squares); and a combination regimen (white circles) of hBAT-1 (10 µg/mouse administered on day 10) and 5FU (20 mg/kg administered on days 6-9 and 15-16).
Figure 9:
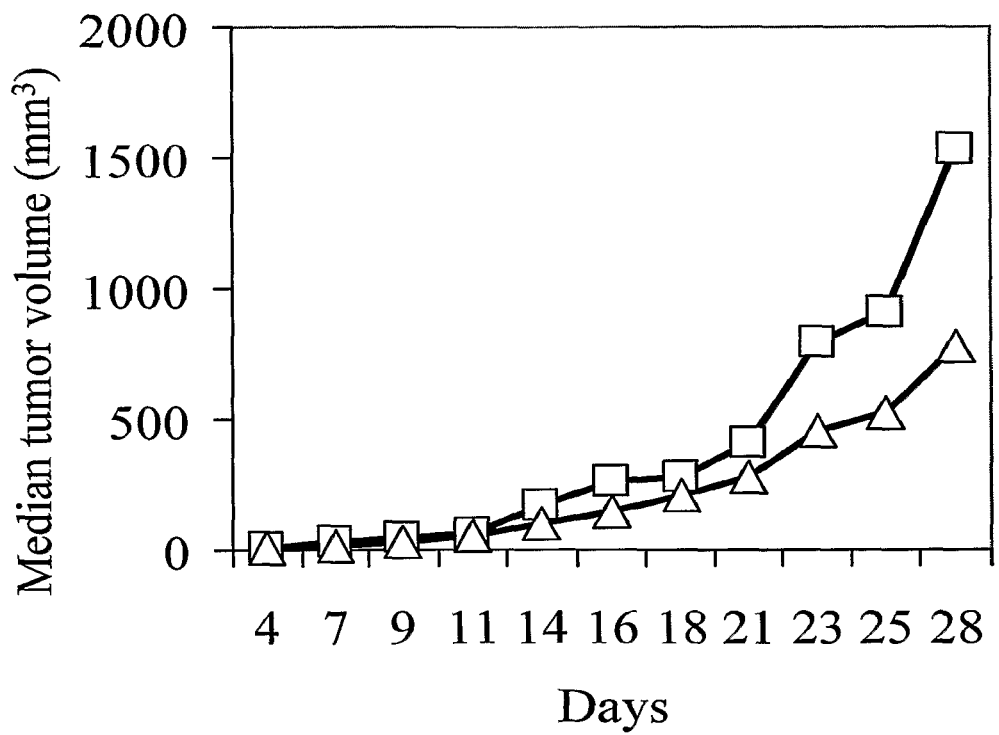
FIG. 9 shows the antitumor effect in CRC bearing mice of 5FU (20 mg/kg administered on days 6-9, 15-17, 22-24 and 29-31; white squares) and a combination regimen (white triangles) of hBAT-1 (10 µg/mouse administered on days 10, 18 and 25) and 5FU (20 mg/kg administered on days 6-9, 15-17, 22-24 and 29-31).
Figure 10:
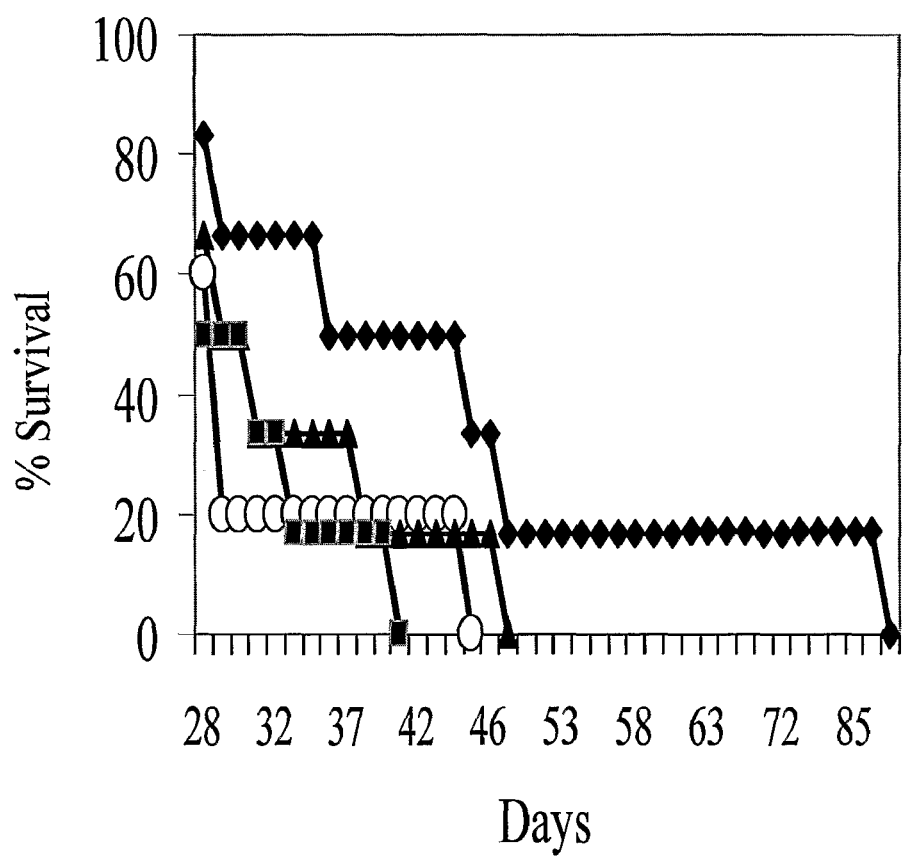
FIG. 10 shows percentage of survival of CRC bearing mice treated with vehicle (white circles); 5FU (20 mg/kg administered on days 6-9, 15-17, 22-24, 29-31, 36-38 and 43-45; black triangles); hBAT-1 (10 µg/mouse administered on days 10, 18, 25, 32 and 39; black squares); and a combination regimen (black diamonds) of hBAT-1 (10 µg/mouse administered on days 10, 18, 25, 32 and 39) and 5FU (20 mg/kg administered on days 6-9, 15-17, 22-24, 29-31, 36-38 and 43-45).
Figure 11:
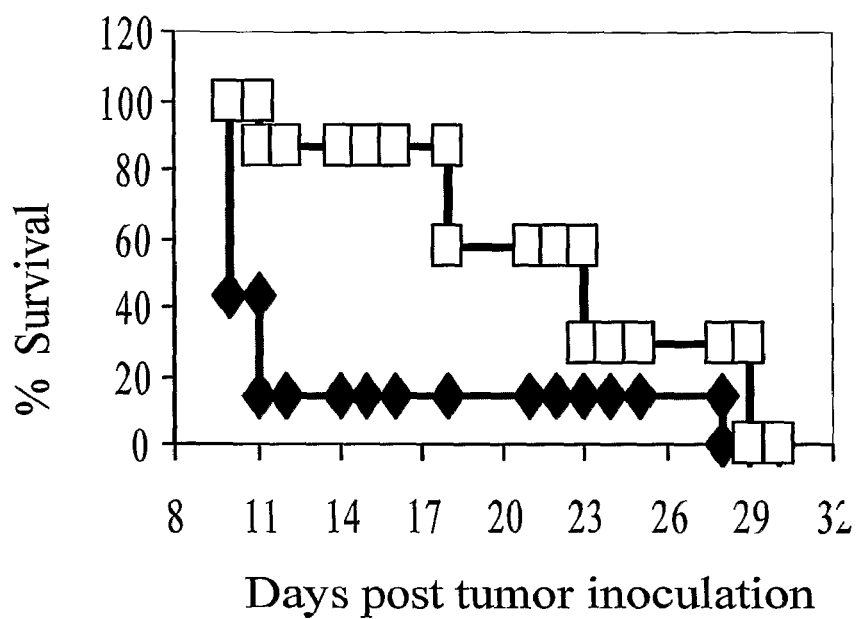
FIG. 11 shows percentage of survival of mice injected with B16 melanoma cells and treated with 5FU (50 mg/kg administered on days 1-4 and 7-8; black diamonds) or a combination regimen (white squares) of hBAT-1 (10 µg/mouse administered on day 10) and 5FU (50 mg/kg administered on days 1-4 and 7-8).
Figure 15:
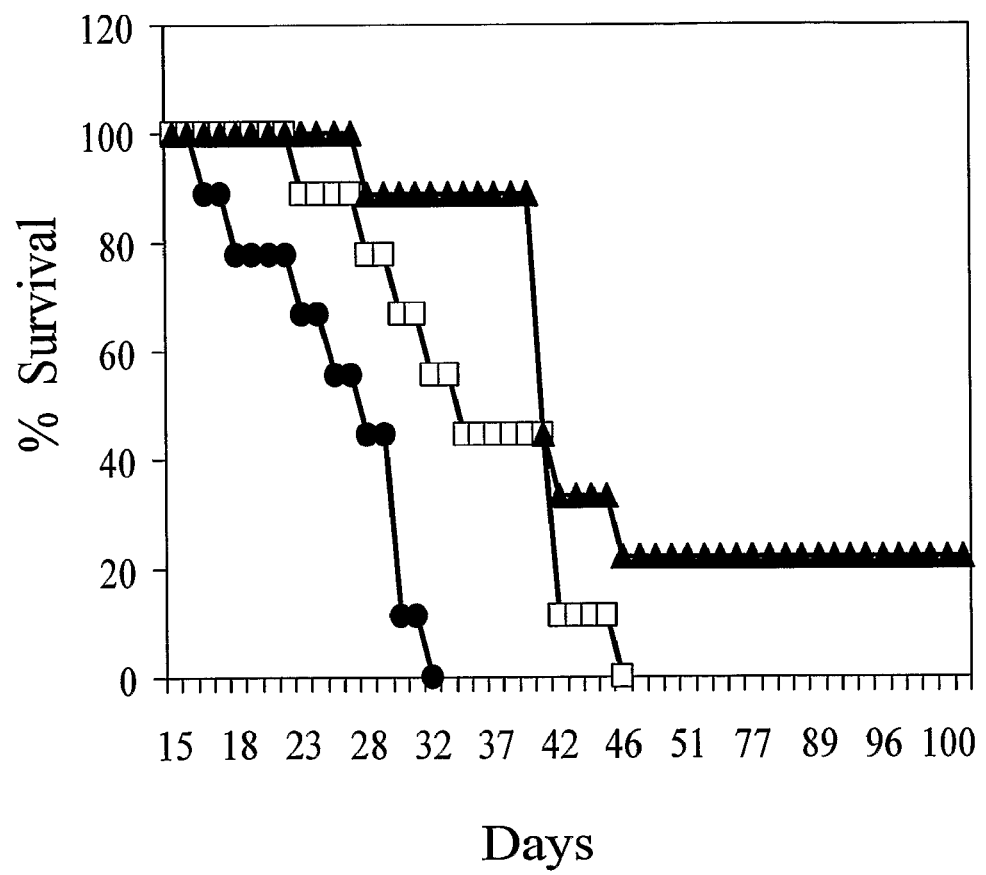
FIG. 15 shows percentage of survival of CRC bearing mice treated with vehicle (black circles); oxaliplatin (1 mg/kg administered on days 4, 7-10, 14-17, 22-24, 29-31; white squares); and a combination regimen (black triangles) of hBAT-1 (10 µg/mouse administered on days 11, 18, 25 and 32) and oxaliplatin (1 mg/kg administered on days 4, 7-10, 14-17, 22-24, 29-31).

In other words, according to one aspect of the present invention the antitumor effect of the humanized antibody of the invention is augmented more than expected when combined with at least one chemotherapeutic agent. Synergy may be shown by greater antitumor effect with combined treatment than would be expected from the additive effect of treatment with the humanized antibody and the chemotherapeutic agent(s), each on its own. For example, synergy is demonstrated in Examples 2, 3 and 6 herein, which disclose that combination therapy according to the invention exerts an increased antitumor effect, as measured by both tumor volume and survival of tumor bearing mice, as compared to the effect of either the antibody or chemotherapy alone. More specifically, in assessing effect on tumor volume, FIG. 8 shows that administration of the combination of hBAT-1 and 5FU is advantageous over each agent on its own, and FIG. 9 shows that the combination of hBAT-1 and 5FU is synergistic over 5FU on its own. Similarly, in assessing effect on survival, it has been demonstrated that administration of the combination of hBAT-1 and 5FU is advantageous over each agent on its own (FIG. 10) or over 5FU on its own (FIG. 11). A different combination, namely hBAT-1 and oxaliplatin, is not only advantageous over oxaliplatin in increasing survival, but also induces complete remission in some of the subjects (FIG. 15). Synergy is also demonstrated by complete remission and generation of tumor-specific memory protection in tumor bearing mice treated with the combination therapy of the invention as compared to the corresponding monotherapies (FIGS. 10, 15, 16, 17).

Figure 1C:
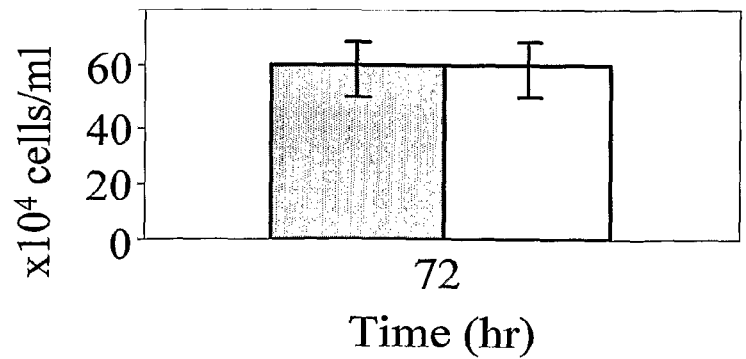
Figure 2A:
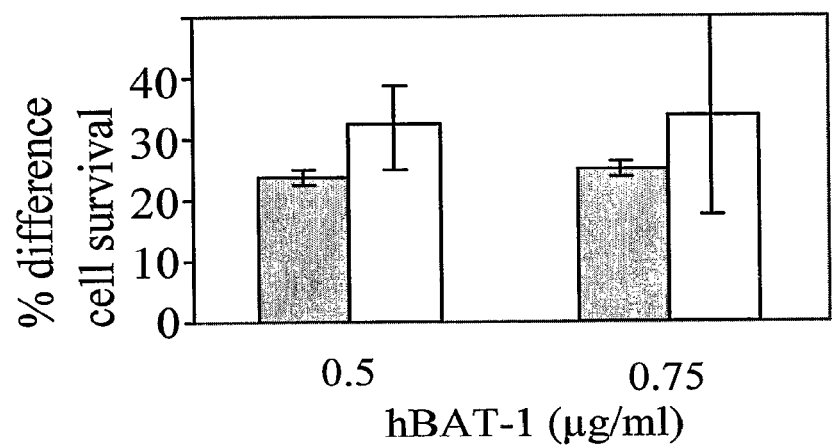
FIGS. 2A-2B show the effect of hBAT-1 in an assay based on viability of lymphocytes when added to cultures 24 prior to addition of vehicle control (gray bars) or 5FU (0.5 mg/ml, white bars), followed by incubation for 72 hours.
Figure 2B:
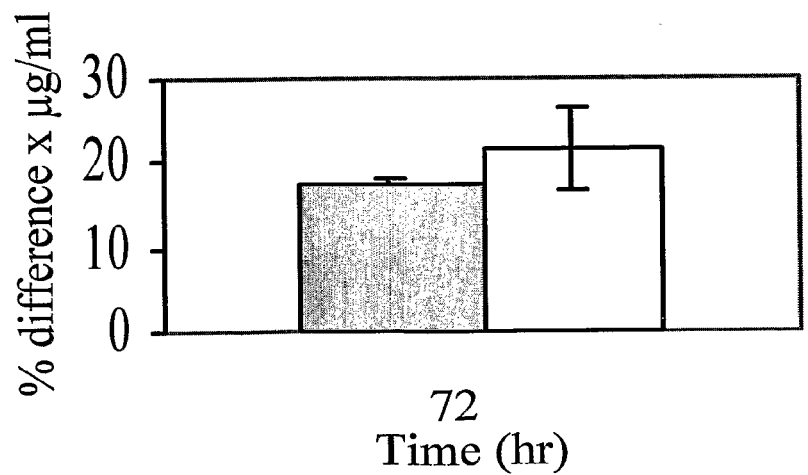
Figure 7A:
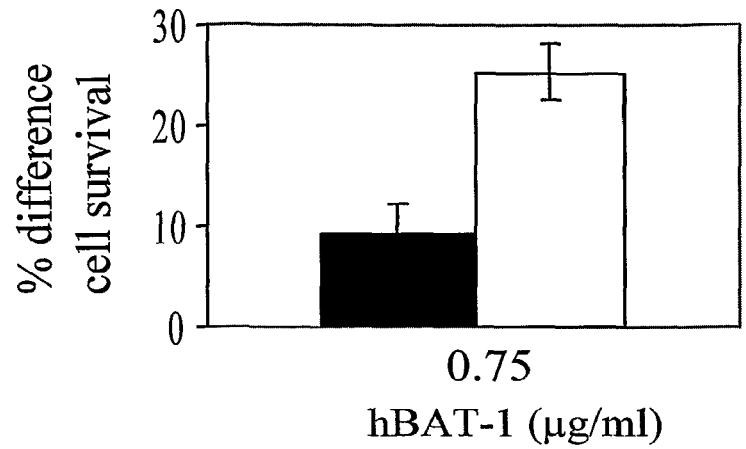
FIGS. 7A-7B show the effect of hBAT-1 in an assay based on viability of isolated human CD4+ lymphocytes when added (at 0.75 ug/ml) 24 prior to addition of vehicle control (black bars) or a chemotherapeutic agent (white bars), followed by incubation for 72 hours. Chemotherapeutic agents used were: 5FU at 1 ug/ml (FIG. 7A) and cisplatin at 10 ug/ml (FIG. 7B). hBAT-1 activity is presented as % difference in cell survival.
Figure 7B:
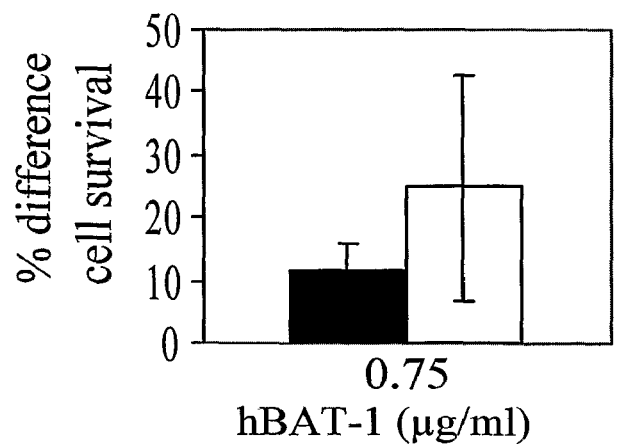

The in vivo effects exerted by the combinations of the invention are supported by in vitro functional assays of lymphocyte cell survival as disclosed in Example 1 herein. As exemplified, sequential treatment of murine lymphocytes with hBAT-1 followed by 5FU (administered after a period of 24 hours) unexpectedly enhanced lymphocyte survival by approximately 30% (FIG. 2A). Concomitant treatment of lymphocytes with hBAT-1 and 5FU only slightly increased lymphocyte survival (FIG. 1A) compared to treatment with hBAT-1 alone, and 5FU on its own did not enhance cell survival (FIG. 1C), indicating mechanistic synergy of the sequential scheduled treatment. Synergistic activity was also observed in in vitro assays with the combination of the chemotherapeutic agent cisplatin and the humanized antibody (FIG. 7B). Thus, combining certain chemotherapeutic agents, with the humanized antibody of the invention results in synergistic effects in vitro and in vivo.

The synergistic effect disclosed and exemplified herein is utterly unexpected, given that BAT antibodies and chemotherapeutic agents are known to have completely different and even opposing mechanisms of action and types of targets. That is, BAT antibodies function by stimulating immune-functioning cells (as disclosed for example in Hardy et al 1994; Hardy et al 1997), whereas chemotherapeutic agents such as 5FU and oxaliplatin act by killing rapidly dividing cells including immune-functioning cells.

As exemplified herein, the combinations according to the present invention are those where use of the chemotherapeutic agents in combination with the humanized antibody of the invention, demonstrate increased or enhanced lymphocyte cell survival. As disclosed in Example 1 and FIGS. 1-7, lymphocyte cell survival may be conveniently assessed using in vitro assays.

Accordingly, in various embodiments, the chemotherapeutic agent may be selected from an antimetabolite, such as the pyrimidine analog 5-fluorouracil, or cytarabin, or a platinum-based drug, such as oxaliplatin or cisplatin. Further, in various embodiments, the chemotherapeutic agent may be other than an agent selected from a topoisomerase I inhibitor (such as SN-38) and an alkylating agent (such as cyclophosphamide). Antitumor effect induced by the combinations of the invention includes the prevention, inhibition of the progression of a tumor, reduction of tumor growth and protection against tumor recurrence, including cancerous and noncancerous tumors. The progression of a tumor includes the invasiveness, metastasis, recurrence and increase in size of the tumor. The reduction of tumor growth also includes the destruction or elimination of a tumor leading to complete remission.

In addition, the invention has been further found to be effective for improving tolerability to chemotherapeutic agents. As is known in the art, a major setback for patients undergoing cancer chemotherapy is the appearance of severe and detrimental adverse side effects due to the potent toxicity of most chemotherapeutic agents. As exemplified herein in Example 3, use of a humanized BAT antibody (CT-011) in combination with 5FU at dose-limiting toxicity (DLT) levels, using a sequential administration schedule, results in enhanced survival of mice. These observations support use of humanized BAT antibodies for improving tolerability to chemotherapeutic agents in patients undergoing chemotherapy.

The invention further provides a method of enhancing survival in a subject with a tumor, which comprises administration of the humanized antibody of the invention, either on its own, or optionally, combined with the further administration of one or more chemotherapeutic agents. For example, the "cure" effect induced by CT-011 in human cancer patients (Example 8) supports such an antibody monotherapy. This aspect of the invention is particularly advantageous in cases where chemotherapy has failed or where the patient is unable to tolerate chemotherapeutic agents.

The invention further provides a method of reducing or preventing recurrence of a tumor, which comprises administration of the humanized antibody of the invention, either on its own, or optionally, combined with the further administration of one or more chemotherapeutic agents. As demonstrated herein in Example 6, combination treatment of experimental animals using the humanized antibody of the invention and chemotherapeutic agents clearly induced a "memory" effect, such that tumor recurrence was inhibited upon re-challenge with the original tumor type.

All types of tumors may be treated by the methods of the present invention. The tumors may be solid or non-solid.

Some examples of solid tumors that can be treated with the combination of the present invention include carcinomas, sarcomas, blastomas or gliomas. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, liver tumors, esophageal tumors and gastric tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers include squamous cell carcinoma, basal cell carcinoma and skin cancers that can be treated by suppressing the growth of malignant keratinocytes, such as human malignant keratinocytes.

Some examples of non-solid tumors include leukemias, multiple myelomas and lymphomas. Some examples of leukemias include acute myelocytic leukemia (AML), chronic myelocytic leukemia (CML), acute lymphocytic leukemia (ALL), chronic lymphocytic leukemia (CLL), erythrocytic leukemia or monocytic leukemia. Some examples of lymphomas include lymphomas associated with Hodgkin's disease, Non-Hodgkin's disease or mantle cell lymphoma.

Currently preferred types of tumors are selected from the following group: colorectal carcinoma; lung carcinoma including non small lung cancer (NSCLC) and small cell lung cancer (SCLC); breast carcinoma; melanoma; ovarian carcinoma; cervical carcinoma, pancreatic cancer; head and neck carcinoma; gastrointestinal carcinoma; esophageal tumors; hepatocellular carcinoma; multiple myeloma; renal cell carcinoma; prostate tumors; non-Hodgkin's lymphoma; Hodgkin's disease; mantle cell lymphoma; Kaposi's sarcoma; squamous cell carcinoma; basal cell carcinoma; acute myeloid leukemia (AML); chronic myelocytic leukemia (CML); acute lymphocytic leukemia (ALL); chronic lymphocytic leukemia (CLL).

It should be noted that according to the teaching of the present invention, the humanized antibody of the invention may be administered before, during, or after commencing chemotherapy and, optionally, radiation therapy, as well as any combination thereof, i.e. before and during, before and after, during and after, or before, during, and after commencing the chemotherapy and, optionally, the radiation therapy. For example, the antibody of the invention may be administered between 1 and 30 days prior to or after commencing chemotherapy. The antibody may further be administered between courses of chemotherapy.

In the combination therapy methods of the invention, the antibodies may be administered in parallel to the chemotherapy, for example substantially simultaneously or concurrently. Other administration schedules may also be used, for example, overlapping schedules or those which involve alternately, sequentially or successively administering the two types of treatment.

Humanized Antibody of the Invention

As used herein, the terms "BAT" and a BAT antibody" are used in a broad sense and specifically cover antibodies identical to or based on the murine monoclonal antibody known as mBAT-1, or an antigen binding fragment thereof. The monoclonal antibody mBAT-1 is secreted by the hybridoma cell line deposited at the Collection Nationale de Cultures de Microorganismes (CNCM), under Accession No. 1-1397, as disclosed in U.S. Pat. No. 5,897,862. Further "BAT" and a BAT antibody" may refer to an antibody, which recognizes the same antigenic epitope as mBAT-1, for example a chimeric antibody as described in U.S. Patent Application Publication No. 2003/0026800. A BAT antibody also includes a humanized antibody, various examples of which are disclosed in WO03/099196 and U.S. Patent Application Publication No. 2008/0025980. The terms "CT-011", "hBAT" and "hBAT-1" are interchangeably used herein to refer to one humanized antibody according to the invention.

In general, the light chain variable region of the humanized monoclonal antibody is characterized by the formula:

$$FR_{L1}\text{-}CDR_{L1}\text{-}FR_{L2}\text{-}CDR_{L2}\text{-}FR_{L3}\text{-}CDR_{L3}\text{-}FR_{L4}$$

wherein each FR is independently a framework region of a human antibody and each CDR is independently a complementarity determining region of the monoclonal mBAT-1 antibody.

In general, the heavy chain variable region of the humanized monoclonal antibody is characterized by the formula:

$$FR_{H1}\text{-}CDR_{H1}\text{-}FR_{H2}\text{-}CDR_{H2}\text{-}FR_{H3}\text{-}CDR_{H3}\text{-}FR_{H4}$$

wherein each FR is independently a framework region of a human antibody and each CDR is independently a complementarity determining region of the monoclonal mBAT-1 antibody.

In particular embodiments, the FRs are derived from the light chain variable region of the human TEL9 antibody (SEQ ID NO: 130), or are modified therefrom in certain amino acid residues.

Human TEL-9 antibody was identified in diverse libraries of immunoglobulin heavy (VH) and light (V kappa and V lambda) chain variable (V) genes prepared from peripheral blood lymphocytes of unimmunized donors (Marks et al. J Mol Biol. 1991, 222:581-97). This antibody was shown to bind specifically to the turkey egg-white lysozyme (TEL) antigen.

FR amino acid sequences derived or modified from the light chain variable region of the human TEL9 antibody may be selected from the group consisting of: $FR_{L1}$, [EIVLT QSPSS LSASV GDRVT ITC; SEQ ID NO: 1]; $FR_{L2}$, [W (F or Y) QQKPG KAPKL (W or L) IY; SEQ ID NO: 2]; $FR_{L3}$, [GVPSR FSGSG SGT (D or S) (Y or F) (C or T) LTINS LQPED FATYY C; SEQ ID NO: 3]; and $FR_{L4}$, [FGGGT KLEIK; SEQ ID NO: 4].

In particular embodiments, the FRs are derived from the heavy chain variable region of the human hsighv1295 antibody (SEQ ID NO: 146), or modified therefrom in certain amino acid residues.

Human hsiggv1295 antibody was isolated from stable hybridomas and Epstein-Barr virus-transformed B cell lines from the synovial fluid or peripheral blood of three patients with rheumatoid arthritis and one patient with systemic lupus erythematosus (Fang et al., J Exp Med. 1994, 179:1445-56).

FR amino acid sequences derived or modified from the heavy chain variable region of the human hsighv1295 antibody may be selected from the group consisting of $FR_{H1}$, [Q (I or V) QLV QSGSE LKKPG ASVKI SCKAS GY (T or S) F (T or S); SEQ ID NO: 5]; $FR_{H2}$, [WV (R OR K) QAPGQ GL (Q or K) WMG; SEQ ID NO: 6]; $FR_{H3}$, [RF (V or A) FSLDT SV (N or S) TAYLQ ITSL (T or N) AEDTG MYFC (V or A) (R or K); SEQ ID NO: 7]; and $FR_{H4}$, [WGQGT LVTVS S; SEQ ID NO: 8].

According to various embodiments, the light chain variable region comprises at least one amino acid sequence selected from the group consisting of: $CDR_{L1}$ [SARSS VSYMH; SEQ ID NO: 9]; $CDR_{L2}$ [RTSNL AS; SEQ ID NO: 10]; $CDR_{L3}$ [QQRSS FPLT; SEQ ID NO: 11], wherein the CDRs are derived from the murine BAT-1 antibody and the subscripts "L" and "H" refer to light and heavy chain regions, respectively.

According to various embodiments, the heavy chain variable region comprises at least one amino acid sequence selected from the group consisting of: $CDR_{H1}$ [NYGMN; SEQ ID NO: 12]; $CDR_{H2}$ [WINTD SGEST YAEEF KG; SEQ ID NO: 13]; $CDR_{H3}$ [VGYDA LDY; SEQ ID NO: 14].

According to various embodiments, the humanized antibody comprises: a light chain variable region selected from the group consisting of: $BATR\kappa_A$ (SEQ ID NO: 15), $BATR\kappa_B$ (SEQ ID NO: 16), $BATR\kappa_C$ (SEQ ID NO: 17), and $BATR\kappa_D$ (SEQ ID NO: 18); and a heavy chain variable region selected from the group consisting of: A (SEQ ID NO: 20), $BATRH_B$ (SEQ ID NO: 21), $BATRH_C$ (SEQ ID NO: 22), $BATRH_D$ (SEQ ID NO: 23) and $BATRH_E$ (SEQ ID NO: 24).

According to yet other embodiments, the humanized antibody comprises variable regions selected from the group consisting of: $BATRH_A/BATR\kappa_A$ (SEQ ID NO: 20/SEQ ID NO: 15), $BATRH_B/BATR\kappa_A$ (SEQ ID NO: 21/SEQ ID NO: 15), $BATRH_B/BATR\kappa_B$ (SEQ ID NO: 21/SEQ ID NO: 16), $BATRH_C/BATR\kappa_B$ (SEQ ID NO: 22/SEQ ID NO: 16), $BATRH_B/BATR\kappa_D$ (SEQ ID NO: 21/SEQ ID NO: 18), and $BATRH_C/BATR\kappa_D$ (SEQ ID NO: 22/SEQ ID NO: 18).

According to various preferred embodiments, the humanized monoclonal antibody has variable regions corresponding to $BATRH_C/BATR\kappa_D$ (SEQ ID NO: 22/SEQ ID NO: 18).

In one embodiment, the humanized BAT antibody has a heavy chain variable region as set forth in SEQ ID NO: 22 which may be encoded by the polynucleotide sequence set forth in SEQ ID NO: 90.

In one embodiment, the humanized antibody has a light chain variable region as set forth in SEQ ID NO: 18 which may be encoded by the polynucleotide sequence set forth in SEQ ID NO: 89. Amino acid and nucleotide sequences of humanized antibodies suitable for use in the invention are disclosed in U.S. Patent Application Publication No. 2008/0025980. Human antibody framework regions of heavy chain variable regions and light chain variable regions suitable for use in the invention include for example SEQ ID NOS: 111-128 and SEQ ID NOS: 130-144, respectively.

Chemotherapy

Chemotherapy drugs are divided into several groups based on their effect on cancer cells, the cellular activities or processes the drug interferes with, or the specific phases of the cell cycle the drug affects. Accordingly, chemotherapy drugs fall in one of the following categories: alkylating agents, nitrosoureas, antimetabolites, anthracyclines, topoisomerase I and II inhibitors, mitotic inhibitors, inter alia platinum based drugs, steroids and anti-angiogenic agents.

Antimetabolites, also termed "nucleoside analogs", replace natural substances as building blocks in DNA molecules, thereby altering the function of enzymes required for cell metabolism and protein synthesis. In the event that they mimic nutrients required for cell growth, the cells eventually undergo lysis. If a nucleoside is replaced with a non-functional nucleoside analog, the latter is incorporated into DNA and RNA, finally inducing cell cycle arrest and apoptosis by inhibiting the celPs ability to synthesize DNA. Antimetabolites are cell-cycle specific and are most effective during the S-phase of cell division as they primarily act upon cells undergoing synthesis of new DNA for formation of new cells. The toxicities associated with these drugs are seen in cells that are growing and dividing quickly. Examples of antimetabolites include purine antagonists, pyrimidine antagonists, and folate antagonists. These agents damage cells during the S phase and are commonly used to treat leukemias, tumors of the breast, ovary, and the gastrointestinal tract, as well as other cancers. Specific examples of antimetabolites include 5-fluorouracil (also known as 5FU), capecitabine, 6-mercaptopurine, methotrexate, gemcitabine, cytarabine, fludarabine and pemetrexed.

Platinum-based chemotherapeutic drugs crosslink DNA in several different ways, interfering with cell division by mitosis. The damaged DNA elicits DNA repair mechanisms, which in turn activate apoptosis when repair proves impossible. Most notable among the DNA changes are the 1,2-intrastrand cross-links with purine bases. These include 1,2-intrastrand d(GpG) adducts which form nearly 90% of the adducts and the less common 1,2-intrastrand d(ApG) adducts. 1,3-intrastrand d(GpXpG) adducts occur but are readily excised by the nucleotide excision repair (NER). Other adducts include inter-strand crosslinks and nonfunctional adducts that have been postulated to contribute to the activity of platinum-based drugs. Interaction with cellular proteins, particularly HMG domain proteins, has also been advanced as a mechanism of interfering with mitosis, although this is probably not its primary method of action. Platinum-based chemotherapeutic drugs include cisplatin (also known as cisplatinum or cis-diamminedichloridoplatinum II (CDDP), carboplatin and oxaliplatin. Cisplatin is frequently designated as an alkylating agent, though it has no alkyl group and cannot carry out alkylating reactions. It is correctly classified as alkylating-like. Platinum-based chemotherapeutic drugs are used to treat various types of cancers, including sarcomas, some carcinomas (e.g. small cell lung cancer, and ovarian cancer), lymphomas and germ cell tumors.

Mitotic inhibitors interfere with cell division. The most known chemotherapeutic agent in this category is paclitaxel (also known as Taxol®, "plant alkaloid", "taxane" and an "antimicrotubule agent"). Together with docetaxel, it forms the drug category of the taxanes. However, other mitotic inhibitors are known, including, but not limited to etoposide, vinblastine and vincristine. Paclitaxel acts by interfering with normal microtubule growth during cell division by arrests their function; it hyper-stabilizes their structure. This destroys the cell's ability to use its cytoskeleton in a flexible manner. Specifically, paclitaxel binds to the β subunit of tubulin, the "building block" of microtubules, and the binding of paclitaxel locks these building blocks in place. The resulting microtubule/paclitaxel complex does not have the ability to disassemble. This adversely affects cell function because the shortening and lengthening of microtubules (termed dynamic instability) is necessary for their function as a mechanism to transport other cellular components. For example, during mitosis, microtubules position the chromosomes all through their replication and subsequent separation into the two daughter-cell nuclei. Furthermore, paclitaxel induces programmed cell death (apoptosis) in cancer cells by binding to the apoptosis stopping protein Bcl-2 (B-cell leukemia 2) and thus arresting its function.

Another group of DNA-interacting drugs widely used in anti-cancer chemotherapy is the group of anthracycline antibiotics which includes, inter alia, daunorubicin, doxorubicin (also known as Adriamycin® and doxorubicin hydrochloride), respinomycin D and idarubicin. These drugs interact with DNA by intercalation and inhibition of macromolecular biosynthesis thereby inhibiting the progression of the enzyme topoisomerase II, which unwinds DNA for transcription. They stabilize the topoisomerase II complex after it has broken the DNA chain for replication, preventing the DNA double helix from being resealed and thereby stopping the process of replication. It is commonly used in the treatment of a wide range of cancers.

Alkylating antineoplastic agents directly attack DNA. They attach an alkyl group to DNA, cross-linking guanine nucleobases in DNA double-helix strands. This makes the strands unable to uncoil and separate. As this is necessary in DNA replication, the cells can no longer divide. These drugs act nonspecifically. Cyclophosphamide is an alkylating agent, however, it is a highly potent immunosuppressive substance.

Topoisomerase I and II inhibitors interfere with the enzymatic activity of topoisomerase I and 2, respectively, eventually leading to inhibition of both DNA replication and transcription. Examples of topoisomerase I inhibitors include topotecan and irinotecan. Irinotecan, is a prodrug converted to a biologically active metabolite 7-ethyl-10-hydroxy-camptothecin (SN-38) by a carboxylesterase-converting enzyme. One thousand-fold more potent than its parent compound irinotecan, SN-38 inhibits topoisomerase I activity by stabilizing the cleavable complex between topoisomerase I and DNA, resulting in DNA breaks that inhibit DNA replication and trigger apoptotic cell death. Because ongoing DNA synthesis is necessary for irinotecan to exert its cytotoxic effects, it is also classified as an S-phase-specific agent. Examples of topoisomerase II inhibitors include etoposide and teniposide.

Anti-angiogenic agents interfere with the generation of new blood vessels, eventually leading to the "starvation" of tumors. Non-limiting examples of anti-angiogenic agents include the monoclonal antibody bevacizumab, dopamine and tetrathiomolybdate.

Vascular endothelial growth factor (VEGF) is a 32-42 kDa dimeric glycoprotein which mediates vasodilatation, increased vascular permeability and endothelial cell mitogenesis. Differential exon splicing of the VEGF gene results in three main mRNA species which code for three secreted isoforms (subscripts denote numbers of amino acids): VEGF189, VEGF165, and VEGF121. A number of minor splice variants have also been described (VEGF206, VEGF183, VEGF145 and VEGF148). Variants of VEGF polypeptides and their use in cancer therapy is disclosed for example, in WO/2003/012105.

Radiation

The source of radiation that may be used in combination with the humanized antibody of the invention and the chemotherapeutic agent(s) can be either external or internal to the patient being treated. When the source is external to the patient, the therapy is known as external beam radiation therapy (EBRT). When the source of radiation is internal to the patient, the treatment is called brachytherapy (BT).

Radiation is administered in accordance with well known standard techniques using standard equipment manufactured for this purpose, such as AECL Theratron and Varian Clinac.

The distance between the source of the external radiation and the point of entry into the patient may be any distance that represents an acceptable balance between killing target cells and minimizing side effects. Typically, the source of the external radiation is between 70 and 100 cm from the point of entry into the patient.

Brachytherapy is generally carried out by placing the source of radiation in the patient. Typically, the source of radiation is placed approximately 0-3 cm from the tissue being treated. Known techniques include interstitial, intercavitary, and surface brachytherapy. The radioactive seeds can be implanted permanently or temporarily. Some typical radioactive atoms that have been used in permanent implants include iodine-125 and radon. Some typical radioactive atoms that have been used in temporary implants include radium, cesium-137, and iridium-192. Some additional radioactive atoms that have been used in brachytherapy include americium-241 and gold-198.

The dose of radiation depends on numerous factors as is well known in the art. Such factors include the organ being treated, the healthy organs in the path of the radiation that might inadvertently be adversely affected, the tolerance of the patient for radiation therapy, and the area of the body in need of treatment. The dose will typically be between 1 and 100 Gy, and more particularly between 2 and 80 Gy. Some doses that have been reported include 35 Gy to the spinal cord, 15 Gy to the kidneys, 20 Gy to the liver, and 65-80 Gy to the prostate. It should be emphasized, however, that the invention is not limited to any particular dose. The dose will be determined by the treating physician in accordance with the particular factors in a given situation, including the factors mentioned above.

The dose of radiation for brachytherapy can be the same as that mentioned above for external beam radiation therapy. In addition to the factors mentioned above for determining the dose of external beam radiation therapy, the nature of the radioactive atom used is also taken into account in determining the dose of brachytherapy.

Compositions, Administration and Dosages

For use in the methods of the invention, the humanized antibody may be formulated in a conventional manner using one or more pharmaceutically acceptable carriers, stabilizers or excipients (vehicles) to form a pharmaceutical composition as is known in the art, in particular with respect to protein active agents. Carrier(s) are "acceptable" in the sense of being compatible with the other ingredients of the composition and not deleterious to the recipient thereof. Suitable carriers typically include physiological saline or ethanol polyols such as glycerol or propylene glycol.

The antibody may be formulated as neutral or salt forms. Pharmaceutically acceptable salts include the acid addition salts (formed with free amino groups) and which are formed with inorganic acids such as hydrochloric or phosphoric acids, or such organic acids such as acetic, oxalic, tartaric and maleic. Salts formed with the free carboxyl groups may also be derived from inorganic bases such as sodium, potassium, ammonium, calcium, or ferric hydroxides, and organic bases as isopropylamine, trimethylamine, 2-ethylamino ethanol, histidine and procaine.

The compositions may be suitably formulated for intravenous intramuscular, subcutaneous, or intraperitoneal administration and conveniently comprise sterile aqueous solutions of the antibody, which are preferably isotonic with the blood of the recipient. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example trehalose), amino acids, inorganic acids and admixtures thereof. Stabilizers are used in aqueous solutions at the appropriate concentration and pH. The pH of the aqueous solution is adjusted to be within the range of 5.0-9.0, preferably within the range of 6-8. In formulating the antibody, anti-adsorption agent may be used. Other suitable excipients may typically include an antioxidant such as ascorbic acid.

The compositions may be formulated as controlled release preparations which may be achieved through the use of polymer to complex or absorb the proteins. Appropriate polymers for controlled release formulations include for example polyester, polyamino acids, polyvinyl, pyrrolidone, ethylenevinylacetate, and methylcellulose. Another possible method for controlled release is to incorporate the antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with carriers, such as lactose, sucrose, starch, talc magnesium stearate, crystalline cellulose, methyl cellulose, carboxymethyl cellulose, glycerin, sodium alginate or gum arabic.

The humanized antibody of the invention is preferably administered parenterally, generally by intravenous infusion. Administration may also be by intraperitoneal, oral, subcutaneous, or intramuscular routes. Antibodies are generally administered in the range of about 0.1 to about 20 mg/kg of patient weight, commonly about 0.5 to about 10 mg/kg, and often about 1 to about 5 mg/kg. In this regard, it is preferred to use antibodies having a circulating half-life of at least 12 hours, preferably at least 4 days, more preferably up to 21 days. Chimeric and humanized antibodies are expected to have circulatory half-lives of up to four and up to 14-21 days, respectively. In some cases it may be advantageous to administer a large loading dose followed by periodic (e.g., weekly) maintenance doses over the treatment period. Antibodies can also be delivered by slow-release delivery systems, pumps, and other known delivery systems for continuous infusion. Dosing regimens may be varied to provide the desired circulating levels of a particular antibody based on its pharmacokinetics. Thus, doses will be calculated so that the desired circulating level of therapeutic agent is maintained.

Typically, the effective dose will be determined by the activity of the therapeutic combination and the condition of the subject, as well as the body weight or surface area of the subject to be treated. The size of the dose and the dosing regimen also will be determined by the existence, nature, and extent of any adverse side effects that accompany the administration of each agent in the combination of the invention in a particular subject. In determining the effective amount of the therapeutic composition to be administered, the physician needs to evaluate inter alia circulating plasma levels, toxicity, and progression of the disease.

In various embodiments of the combination methods of the invention, the humanized antibody and the chemotherapeutic agent may be administered according to any of a number of treatment schedules, also referred to "dosing schedules" and "administration regimens", referring to the frequency of administration and order of administration of each active agent. For example, the humanized antibody and the chemotherapeutic agent may be administered substantially simultaneously i.e. at the same time, using for example a combined dosage form or separate dosage forms. This form of administration may also be referred to as "concomitant" administration. Concurrent administration refers to administration of the active agents within the same general time period, for example on the same day(s) but not necessarily at the same time. For example, one active agent may require administration with food, while the other requires administration in the semi-fasting state. Alternate administration includes administration of one agent during a particular time period, for example over the course of a few days or a week, followed by administration of the other agent during a subsequent identical period of time, and then repeating the pattern for one or more cycles. Sequential or successive administration includes administration of one agent during a first time period, using one or more doses, followed by administration of the other agent during a second time period using one or more doses. An overlapping schedule may also be employed, which includes administration of the active agents on different days over the treatment period, not necessarily according to a regular sequence. Variations on these general guidelines may also be employed, according to the agents used and the condition of the subject.

In some particular combinations, it may be advantageous to use a specific sequence of administration e.g. one agent prior to the other. For example, as demonstrated herein (FIG. 5) dacarbazine adversely affects the activity of the antibody when given concomitantly but not when added 24 hours after the humanized antibody.

Having now generally described the invention, the same will be more readily understood through reference to the following examples, which are provided by way of illustration and are not intended to be limiting of the present invention.

EXAMPLES

Example 1

In Vitro Functional Assay

Figure 5A:
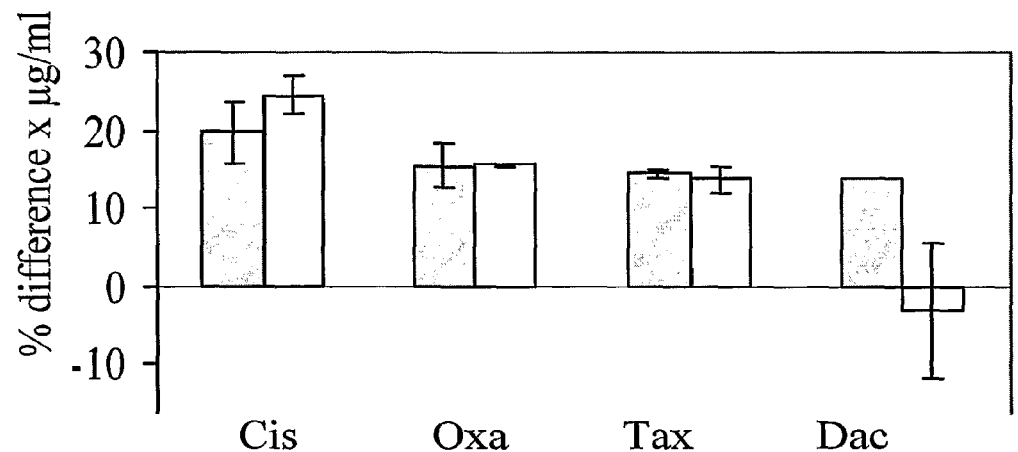
FIGS. 5A-5B show the effect of hBAT-1 in an assay based on viability of lymphocytes when added to cultures (at dose response concentrations of 0.25 to 1.25 ug/ml) concomitantly (FIG. 5A) or 24 prior to (FIG. 5B) addition of vehicle control (gray bars) or the indicated chemotherapeutic agent (white bars), followed by incubation for 72 hours. Cis, cisplatin (10 ug/ml); Oxa, oxaliplatin (10 ug/ml); Tax, paclitaxel (0.43 ug/ml); Dac, dacarbazine (1 ug/ml). hBAT-1 activity is presented as Area Under a dose response Curve (AUC presented as % difference×ug/ml). The incubation time with hBAT-1 (72 hours) is indicated on the x-axis.
Figure 5B:
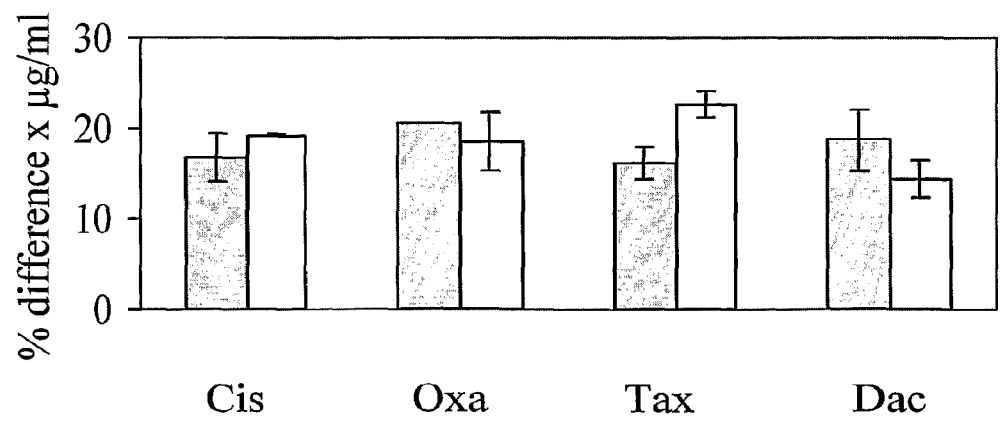
Figure 6A:
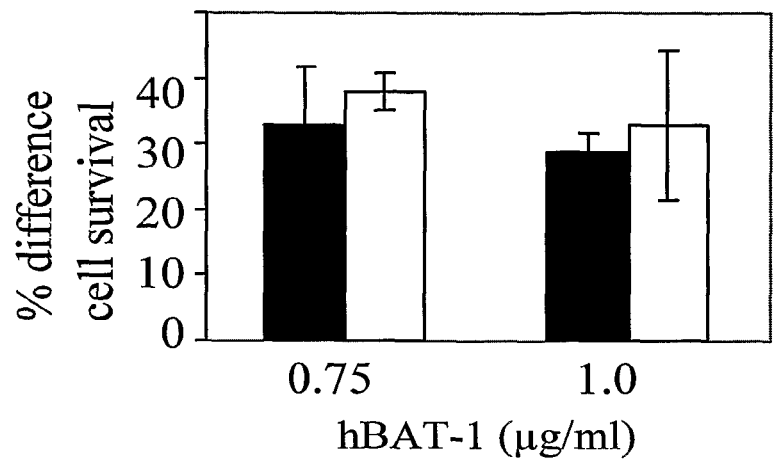
FIGS. 6A, 6B and 6C show the effect of hBAT-1 (0.75 or 1 ug/ml, as indicated) in an assay based on viability of lymphocytes when added concomitantly to cultures with vehicle control) (black bars) or in combination with a chemotherapeutic agent (white bars) followed by incubation for 72 hours. Chemotherapeutic agents used were: cytarabine at 2 mg/ml (FIG. 6A), cyclophosphamide at 1 mg/ml (FIG. 6B) and doxorubicin at 0.03 mg/ml (FIG. 6C). hBAT-1 activity is presented as % difference in cell survival.
Figure 6B:
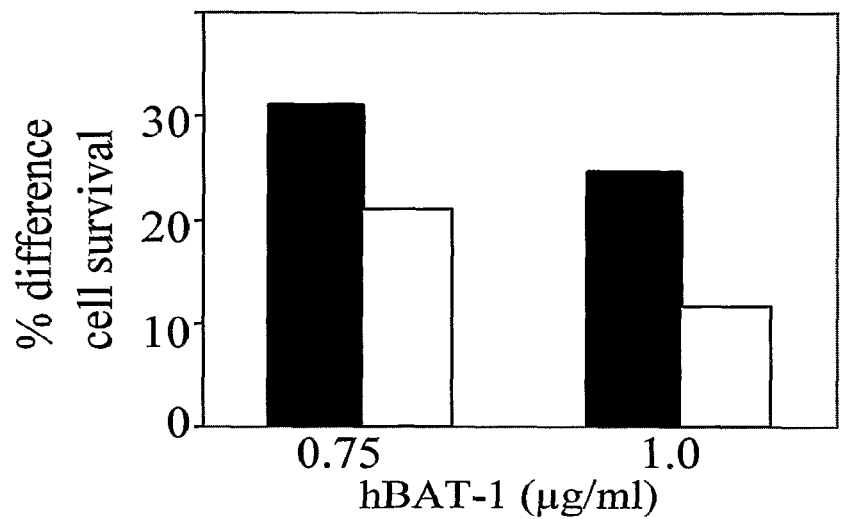
Figure 6C:
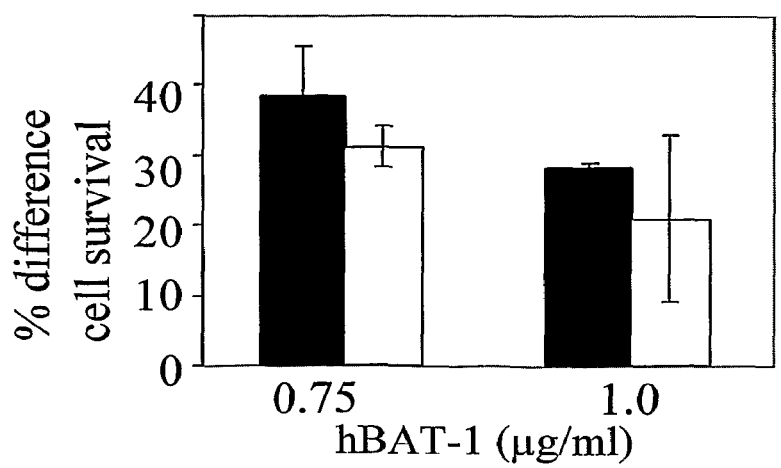

The functional assay is based on the ability of hBAT-1 to enhance the survival of murine and human lymphocytes in culture. In the present Example, the effect of hBAT-on enhanced survival of lymphocytes alone and in combination with chemotherapeutic drugs was evaluated and expressed by % difference in cell survival or by the Area Under the dose response Curve (AUC, expressed in % difference×µg/ml). The chemotherapeutic agent was applied concomitantly or 24 hours after hBAT-1 treatment at the indicated concentrations. Chemotherapeutic agents tested in the functional assay included 5FU (FIGS. 1, 2 and 7), SN-38, an active derivative of irinotecan (FIGS. 3 and 4), cisplatin, oxaliplatin, Taxol (paclitaxel) and dacarbazine (FIGS. 5 and 7), cytarabine, cyclophosphamide and doxorubicin (FIG. 6).

Figure 3A:
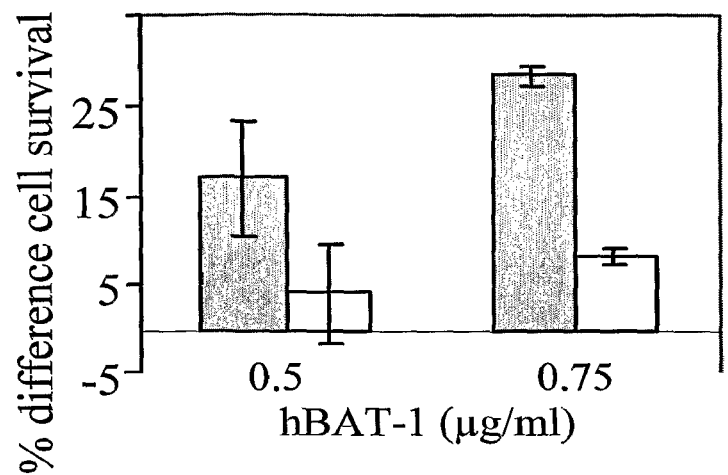
FIGS. 3A-3B show the effect of hBAT-1 in an assay based on viability of lymphocytes when concomitantly added to cultures with vehicle control (gray bars) or in combination with SN-38 (active form of irinotecan at 0.1 mg/ml, white bars) and incubated for 72 hours.
Figure 3B:
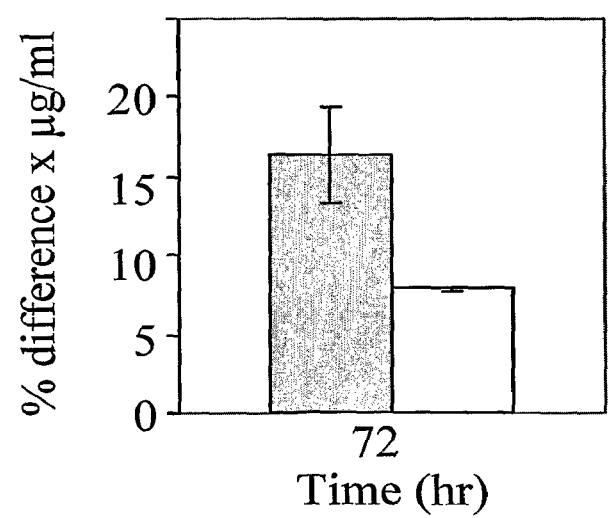
Figure 4A:
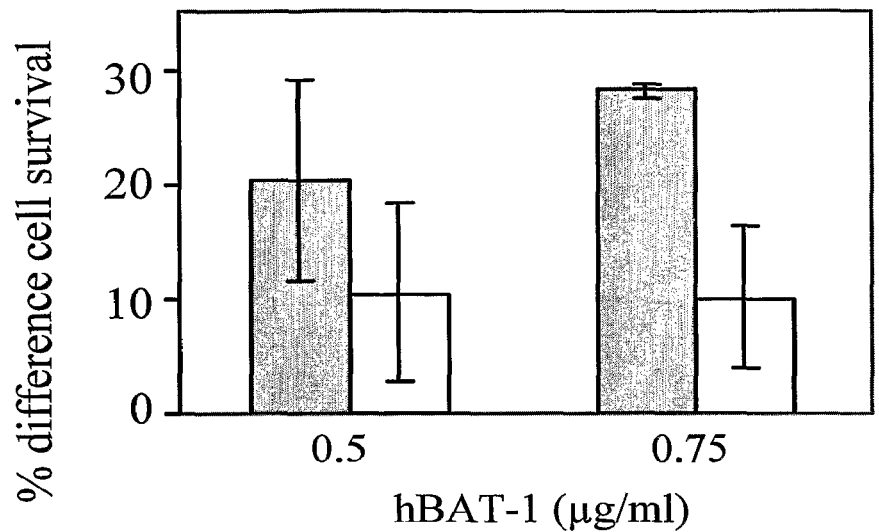
FIGS. 4A-4B show the effect of hBAT-1 in an assay based on viability of lymphocytes when added to cultures 24 prior to addition of vehicle control (gray bars) or SN-38 (active form of irinotecan at 0.1 ug/ml, white bars), followed by incubation for 72 hours.
Figure 4B:
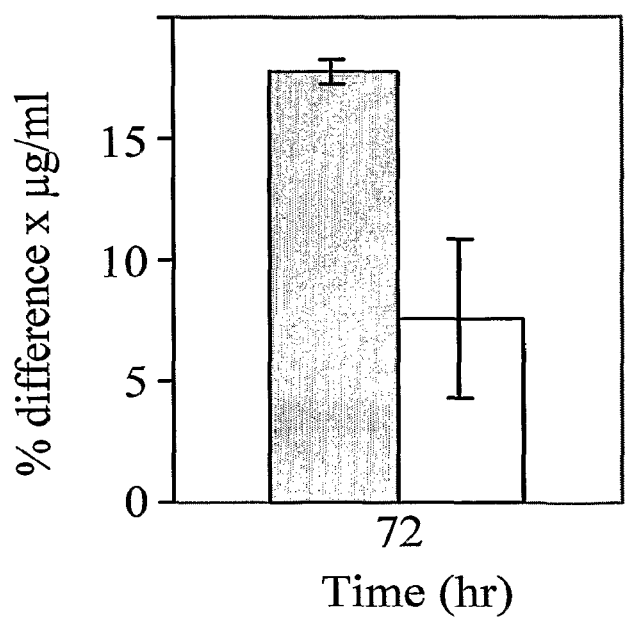

The results indicate that specific agents (e.g. 5FU, cisplatin, oxaliplatin, paclitaxel and cytarabine) do not adversely affect the activity of hBAT-1 in murine lymphocytes. Moreover, when given concomitantly with (cisplatin), or sequentially (5FU and paclitaxel) with hBAT-1, a synergistic effect is observed, expressed by 20% to 30% enhancement in activity values (% difference in cell survival and AUC). Use of a chemotherapeutic agent alone has no activity in increasing lymphocyte cell survival in this functional assay (FIG. 1C). Synergistic results were obtained with isolated human CD4+ lymphocytes, demonstrating that sequential treatment of 5FU or cisplatin in combination with hBAT resulted in activity (% difference in cell survival) that is 2 fold higher than the activity of the antibody alone (FIG. 7). The results also suggest that certain chemotherapeutic agents (e.g. SN-38; cyclophosphamide) may not be suitable for use in combination with humanized BAT antibodies, since they do not enhance cell survival when given in combination with hBAT-1 in murine lymphocyte culture. In addition, certain chemotherapeutic agents (e.g. dacarbazine) may be suitable only when used in a sequential administration schedule (FIG. 3-5).

Example 2

Combination Therapy for Colorectal Cancer Tumors

Colorectal carcinoma tumors (CT26 tumors) were induced by S.C. injection of CT26 cells, $10^6$ cells/mouse (n=6). Day of injection is referred herein as day 0. 5-FU, 20 mg/kg, was administered I.P. on days 6-9, 15-17, 22-24 and 29-31, 36-38 and 43-45. hBAT-1, 10 mg/mouse, was administered I.V. on days 10, 18, 25, 32 and 39 (FIG. 8-10). A case of relapse after complete remission (observed only in the combination therapy group) was further treated with 5FU at 20 mg/kg, on days 73-74, 77-80, 85-87, 92-93 and hBAT-1, 10 mg/mouse, administered I.V. on days 81 and 88.

In a follow up study on tumor size after a single cycle of treatment, tumor volume was measured every other day on days 4 to 16 post tumor inoculation. The results indicate that the combined therapy with 5FU is advantageous over therapy with either 5FU or hBAT-1 alone (FIG. 8).

In a follow up study on tumor size after 3 alternate cycles of treatment, tumor volume was measured every other day on days 4 to 28. The results indicate that the combination therapy of hBAT-1 antibody with 5FU is not only advantageous over 5FU monotherapy but the increase in activity is synergistic (FIG. 9).

In a follow up study on overall survival, percentage survival was monitored and is presented in FIG. 10 from day 28 and onwards. The results clearly show that in mice treated with the combination therapy, the percent of survival is significantly higher than in mice treated with either hBAT-1 or 5FU monotherapies, leading to durable complete remission in approximately 17% of the mice.

Example 3

Combination Therapy for Melanoma

Mice (n=7) were inoculated subcutaneously with B16 melanoma cells at $5×10^5$ cells/mouse. Inoculation day is referred herein as day 0. 5-FU was administered intraperitonally at 50 mg/kg on days 1-4 and 7-8. In the combination therapy group, a single dose of 10 mg/mouse of hBAT-1 was injected intravenously on day 10.

Percentage survival was monitored beginning at day 8. In mice treated with the combination therapy the percent of survival was significantly higher than in mice treated with high dosage of 5FU (FIG. 11).

Stated otherwise, combination treatment, using a sequential administration schedule in which the humanized antibody was administered after 9 daily cycles of 5FU at dose-limiting toxicity (DLT) levels (50 mg/kg/day), resulted in enhanced survival of mice in an experimental melanoma model. The results clearly suggest that the combination therapy improves tolerability to DLT levels of 5-FU.

Example 4

Combination Therapy with Irinotecan (1)

Figure 12:
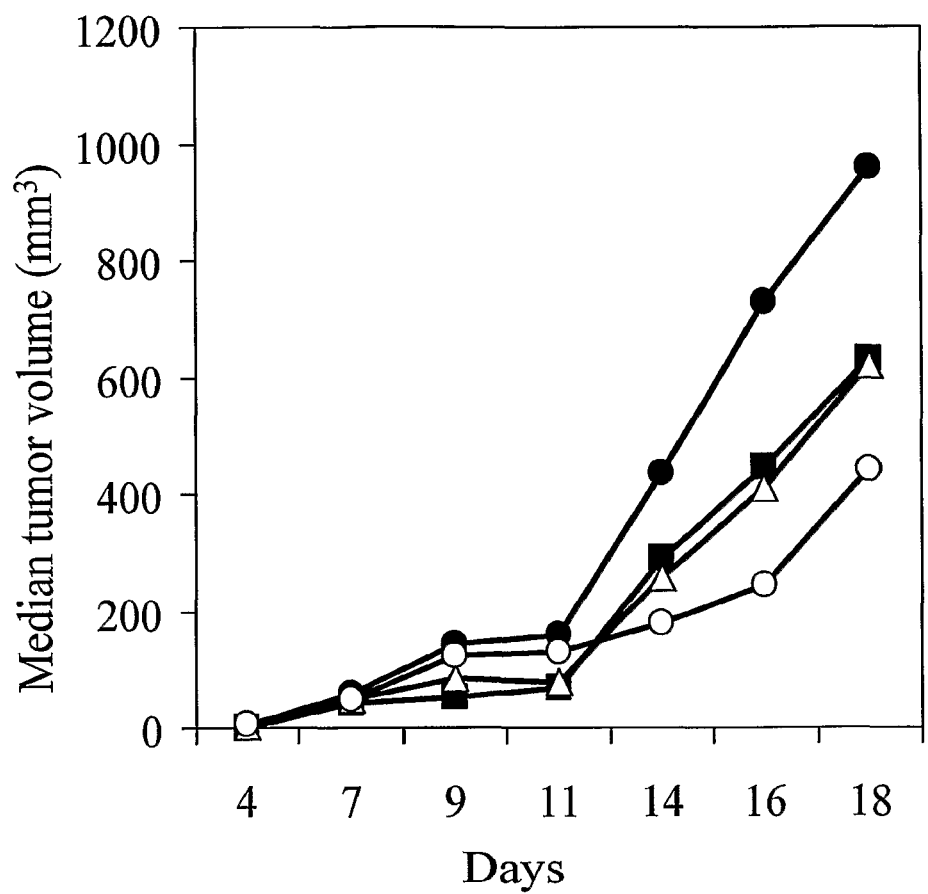
FIG. 12 shows the antitumor effect, as evaluated by median tumor volume, upon treatment with vehicle (black circles); irinotecan (100 mg/kg administered on days 7 and 15; black squares); hBAT-1 (10 µg/mouse administered on day 10; white circles); and a combination regimen (white triangles) of hBAT-1 (10 µg/mouse administered on day 10) and irinotecan (100 mg/kg administered on days 7 and 15) in CRC bearing mice.

Colorectal carcinoma tumors (CT26 tumors) were induced by S.C. injection of CT26 cells, $10^6$ cells/mouse (n=6). Day of injection is referred herein as day 0. Irinotecan, 100 mg/kg, was administered I.P. on days 7 and 15. hBAT-1, 10 mg/mouse, was administered I.V. on day 10 (FIG. 12).

In a follow up study on tumor size after a single cycle of treatment, tumor volume was measured daily on days 4 to 18. The results indicate that the combination therapy of hBAT-1 antibody with irinotecan is as effective as monotherapy with irinotecan, but less effective than hBAT-1 monotherapy (FIG. 12).

Example 5

Combination Therapy with Irinotecan (2)

Figure 13:
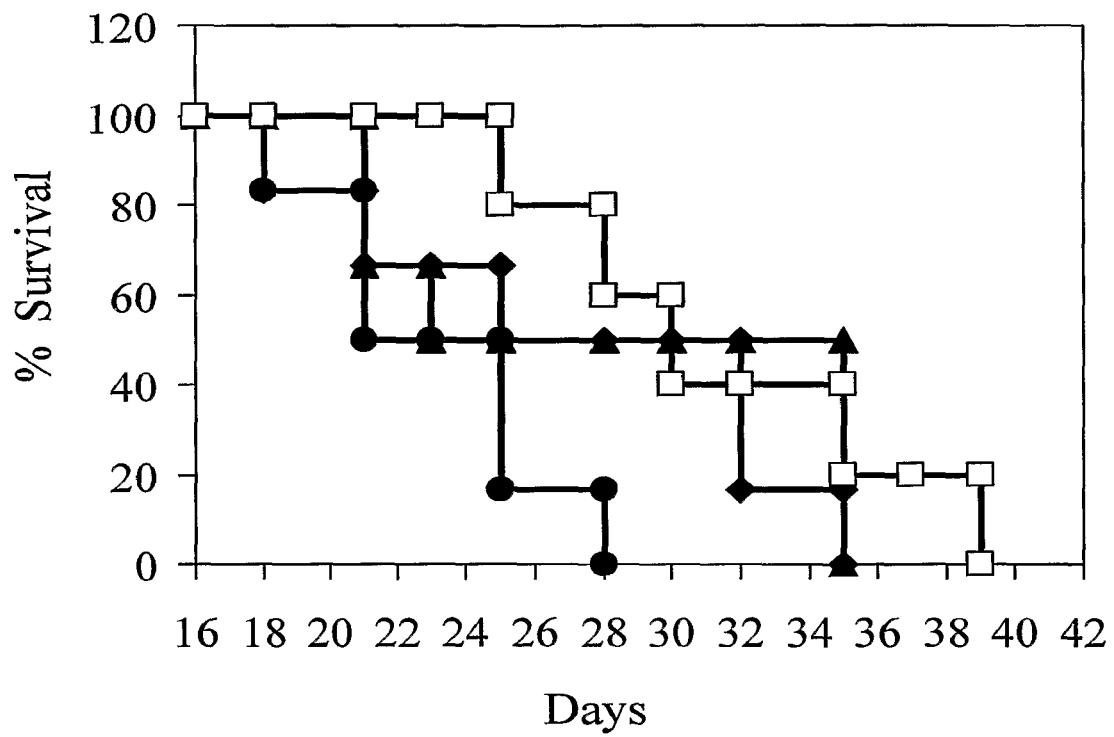
FIG. 13 shows percentage of survival of CRC bearing mice treated with vehicle (black circles); irinotecan (100 mg/kg administered on days 7 and 15, 22 and 29; black triangles); hBAT-1 (10 µg/mouse administered on days 10, 18, 25 and 32; white squares); and a combination regimen (black diamonds) of hBAT-1 (10 µg/mouse administered on days 10, 18, 25 and 32) and irinotecan (100 mg/kg administered on days 7 and 15, 22 and 29).

Colorectal carcinoma tumors (CT26 tumors) were induced by S.C. injection of CT26 cells, $10^6$ cells/mouse (n=6). Day of injection is referred herein as day 0. Irinotecan, 100 mg/kg, was administered I.P. on days 7 and 15. hBAT-1, 10 mg/mouse, was administered I.V. on day 10 (FIG. 13).

Percentage survival was monitored beginning at day 16. The results show that in mice treated with the combination therapy, the percent of survival is comparable to that of mice treated with irinotecan monotherapy, but lower than in mice treated with hBAT-1 monotherapy (FIG. 13).

Example 6

Combination Therapy with Oxaliplatin

Figure 14:
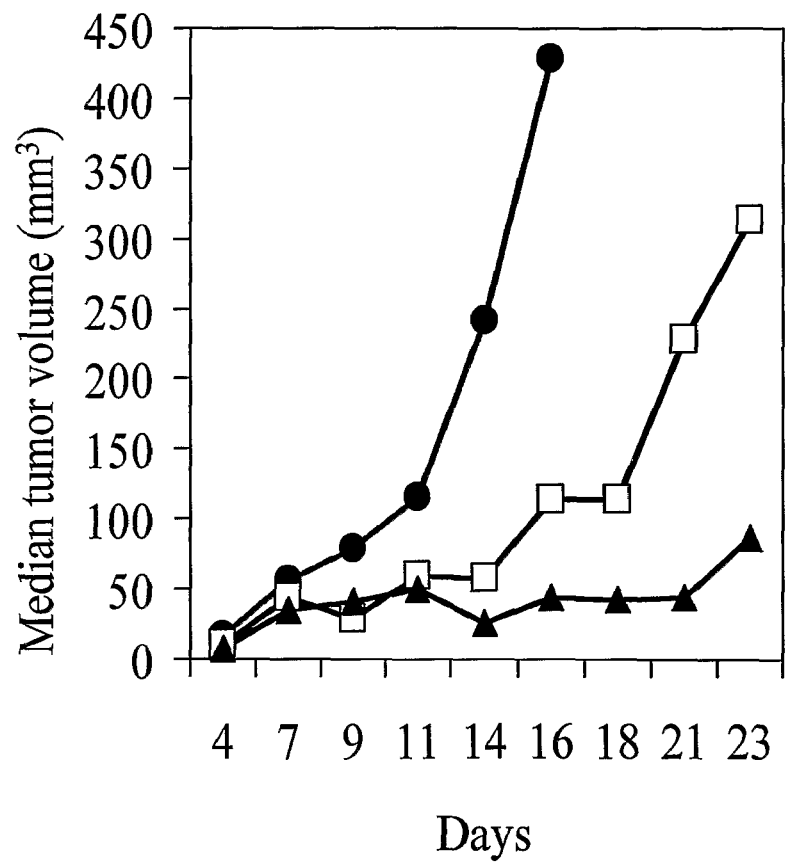
FIG. 14 shows the antitumor effect, as evaluated by the median tumor volume, upon treatment with vehicle (black circles); oxaliplatin (1 mg/kg administered on days 4, 7-10, 14-17 and 22-23; white squares); and a combination regimen (black triangles) of hBAT-1 (10 µg/mouse administered on days 11 and 18) and oxaliplatin (1 mg/kg administered on days 4, 7-10, 14-17 and 22-23) in CRC bearing mice.

Colorectal carcinoma tumors (CT26 tumors) were induced by S.C. injection of CT26 cells, $10^6$ cells/mouse (n=6). Day of injection is referred herein as day 0. Oxaliplatin, 1 mg/kg, was administered I.P. on days 4, 7-10, 14-17, 22-24 and 29-31. hBAT-1, 10 mg/mouse, was administered I.V. on days 11, 18, 25 and 32 (FIG. 14-15).

In a follow up study on tumor size, tumor volume was measured every other day on days 4 to 23 post tumor inoculation. The results indicate that the combined therapy with oxaliplatin is advantageous over therapy with oxaliplatin alone (FIG. 14).

In a follow up on overall survival, percentage survival was monitored beginning at day 15. The results clearly show that in mice treated with the combination therapy, the percent of survival is significantly higher than in mice treated with oxaliplatin monotherapy leading to durable complete remission in approximately 20% of the mice (FIG. 15).

Colorectal carcinoma tumors (CT26 tumors) were re-induced by S.C. injection of CT26 cells, $10^6$ cells/mouse in mice that had been cured for 2 or 5 months by hBAT-1 and oxaliplatin combination therapy (n=3). Colorectal carcinoma tumors were newly induced in control naïve mice at a similar age (n=6). Day of injection is referred herein as day 0 (FIG. 16). Before the re-induction (re-challenge) of CRC, treatment-experienced mice were evaluated for complete clearance of serum levels of hBAT-1 by specific ELISA.

Figure 16A:
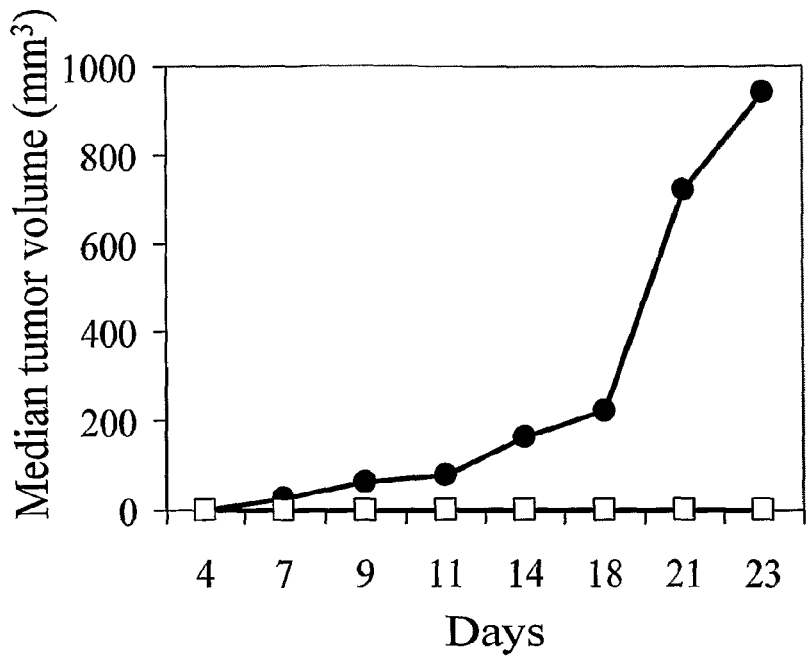
FIGS. 16A-16B show the effect of a combination of hBAT-1 and a chemotherapeutic agent in protecting against tumor recurrence, as evaluated by median tumor volume (FIG. 16A) and percentage of survival (FIG. 16B). Mice (n=3) that had been cured of CRC for 2 or 5 months by a combination regimen of hBAT-1 and oxaliplatin, were then re-challenged with the same CRC cell line (white squares). In addition, naive mice (n=6) were newly introduced with CRC (black circles).

In a follow up study on tumor size, tumor volume was measured every other day and is presented as a follow up from days 4 to 23 post tumor inoculation. The results indicate that in mice previously cured by hBAT-1 and oxaliplatin combination therapy, no tumor was observed during the 2 months follow up, whilst in the control group, the tumor developed within days in all mice (FIG. 16A).

Figure 16B:
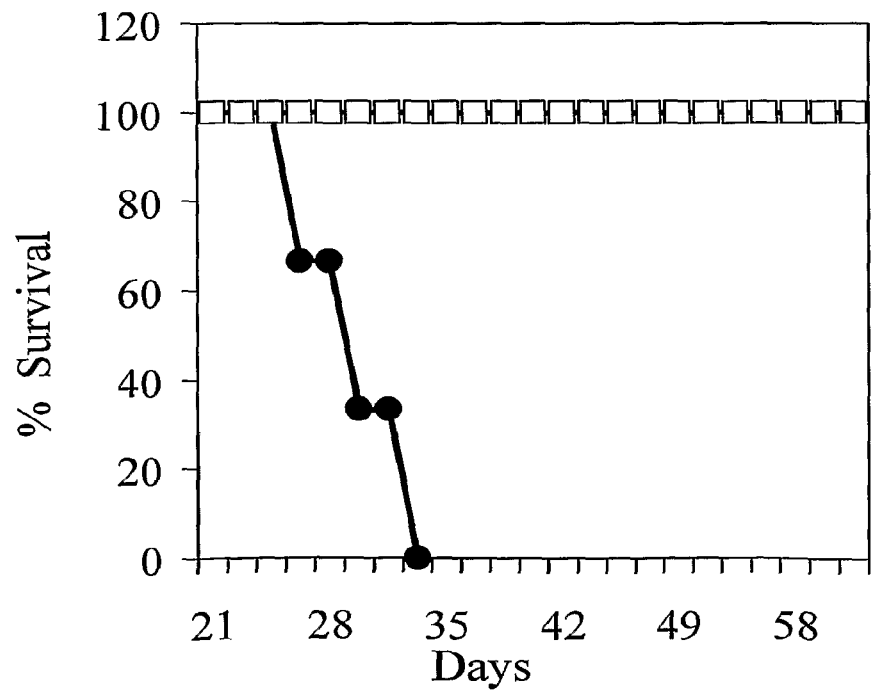

In a follow up study on overall survival, percentage survival was monitored beginning at day 21 post tumor re-inoculation. The results clearly show that the mice which were newly introduced with the tumor (CRC) died within 35 days, whilst mice previously cured by hBAT-1 and oxaliplatin combination therapy were protected from tumor growth, tumor recurrence and death for more than the 72 days of the study follow up (FIG. 16B).

Figure 17A:
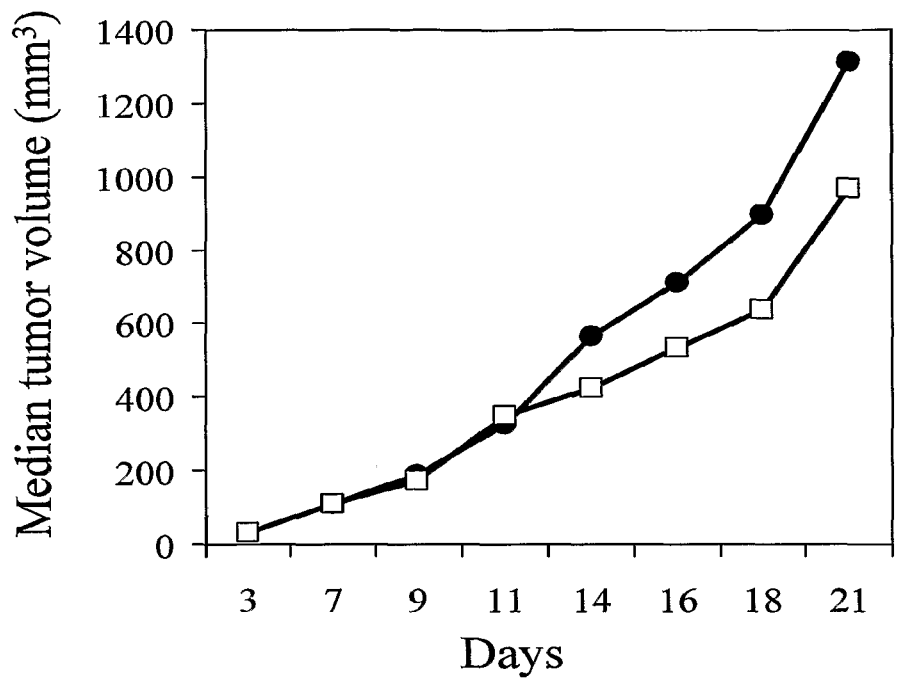
FIGS. 17A-17B show the effect of a combination of hBAT-1 and a chemotherapeutic agent in protecting against tumor recurrence, as evaluated by median tumor volume (FIG. 17A) and percentage of survival (FIG. 17B). Mice (n=2) that had been previously cured of CRC by a combination regimen of hBAT-1 and oxaliplatin, as indicated by the lack of tumor recurrence upon challenge with the same CRC cell line, were then re-challenged with breast carcinoma (white squares). Challenge with breast carcinoma was carried out 2 months after mice exhibited resistance against CRC tumor recurrence. In addition, naïve mice (n=6) were newly introduced with CRC (black circles).
Figure 17B:
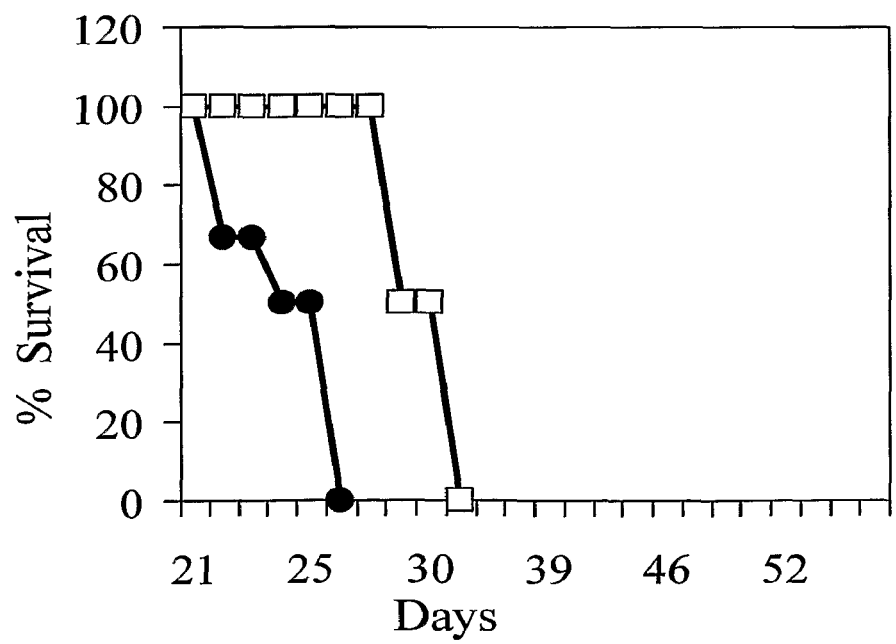

Breast adenocarcinoma tumors (4T1 tumors) were re-induced by S.C. injection of 4T1 cells, $10^6$ cells/mouse in mice previously cured by hBAT and oxaliplatin and protected against re-challenge of CRC for approximately 3 months (Mice described in FIG. 16, n=2). In these mice, the tumor was injected S.C. at a different site than that of the $1^{st}$ CRC and $2^{nd}$ CRC injection sites (re-challenged CRC tumors). Breast adenocarcinoma tumors were also introduced in naïve mice at a similar age (n=6). Day of injection is referred herein as day 0 (FIG. 17).

In a follow up study on tumor size, tumor volume was measured every other day and is presented from days 3 to 21 post tumor inoculation. The results indicate that the breast adenocarcinoma tumors progressed in both mice groups (FIG. 17A). These results clearly show that mice that have acquired full protection against colorectal carcinoma following combination therapy of hBAT-1 and oxaliplatin (FIG. 16A), were not as protected against breast carcinoma (FIG. 17A).

In a follow up study on overall survival, percentage survival was monitored beginning at day 21 post tumor re-inoculation. The results clearly show that the mice in both groups died within 28 to 35 days from breast carcinoma, indicating that mice exhibiting long term protection against CRC recurrence (re-challenge) were not fully protected against a different type of tumor e.g. breast carcinoma. Since all previously treated mice were tested for the complete elimination of circulating serum levels of the antibody of the invention, it appears that the acquired tumor specific protection against colorectal carcinoma was not a result of an active therapy but rather of an immunological memory response induced following previous treatment with the antibody of the invention and oxaliplatin.

Overall, combination therapy of the antibody of the invention and specific chemotherapeutic agents, such as 5FU or oxaliplatin, when administered according to an alternating schedule, results in enhanced antitumor activity, as evaluated by the reduction in tumor growth and the enhancement in survival of tumor bearing mice. Unexpectedly, mice in the combination therapy groups have reached durable complete remission and in the case of oxaliplatin even acquired memory protection against tumor recurrence, as evaluated by re-challenge with the specific tumor (CRC).

Example 7

Effect of CT-011 on Human Effector/Memory T Cells

Figure 18:
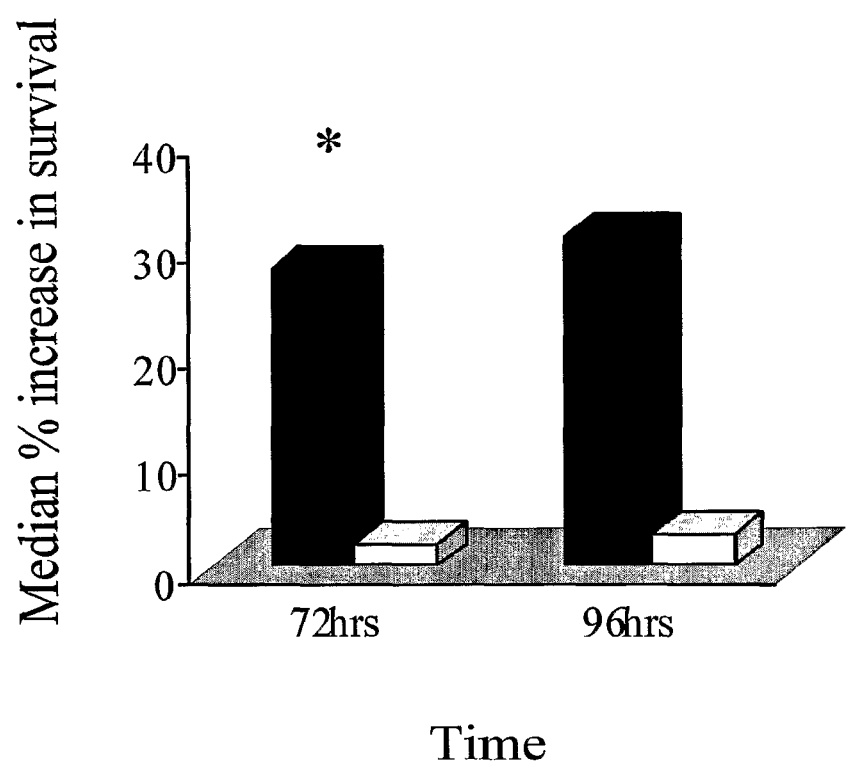
FIG. 18 shows the effect of CT-11 in an cell viability assay, using human CD4+CD45RO+ effector/memory T cells (black bars) and naïve CD4+CD45RO− T cells (white bars) treated with hBAT (1 ug/ml), followed by incubation for 72 and 96 hours. Results are expressed as % difference in cell survival.

The activity of hBAT-1 (CT-011) was assessed in an assay based on viability of human lymphocytes. Effector/memory CD4+CD45RO+ and naïve CD4+CD45RO-lymphocytes were treated with hBAT at 1 ug/ml, followed by incubation for 72 and 96 hours. The results are expressed as % difference in cell survival (FIG. 18).

The results clearly indicate that CT-011 has a significant effect in enhancing the survival of human effector/memory CD4+CD45RO+ lymphocytes, but not that of naïve CD4+CD45RO− lymphocytes. The demonstrated activity of CT-011 in promoting the viability of memory precursor cells is consistent with the in vivo results demonstrating that CT-011 has activity in inducing immunological memory against tumor recurrence.

Example 8

Phase I Clinical Trial of Humanized Monoclonal Antibody CT-011

Introduction

The objectives of this study were to assess the dose-limiting toxicities (DLTs), to determine the maximum tolerated dose (MTD) and to study the pharmacokinetics of CT-011 administered once to patients with advanced hematological malignancies. A full description of the study is provided in Berger et al. Clin. Cancer Res. 2008; 14 (10) May 15, 2008.

Patients And Methods

Entrance criteria for the study required that enrolled patients had to have one of the following hematological malignancies: acute myeloid leukemia (AML), chronic lymphocytic leukemia (CLL), non-Hodgkin's lymphoma (NHL), Hodgkin's lymphoma (HL), or multiple myeloma (MM) at an advanced stage of their disease and following chemotherapy and/or stem cell transplantation (SCT). Patients were eligible for this study provided that they met the criteria as set out in Berger et al.

Importantly, the criteria included: At least 4 weeks from stem cell transplantation (SCT) or 1 week from donor lymphocyte infusion (DLI); Life expectancy >3 months; Patients who were either receiving or did not recover from the effect of therapies having immune suppressive effects, or who were suffering from an autoimmune disorder were to be excluded. The exception to this was hydroxyurea treatment of AML patients, which was allowed to proceed. The use of concomitant anti-cancer treatment (chemotherapy and immunotherapy) was prohibited and accordingly was to be stopped at least 4 weeks prior to CT-011 administration.

The study enrolled a total of 17 patients. One patient who was enrolled at the lowest dose level (0.2 mg/kg) was re-enrolled 5 months after the first administration at a higher dose level (3.0 mg/kg) as a compassionate treatment for a total of 18 administered treatments. The total amount of CT-011 was determined based on the planned dosing (mg/kg base) and body weight. The infusion was carried out in a stepwise manner increasing the rate from 50 mL/hr to 100 mL/hr, and all patients received pre-medication prior to infusion consisting of a pain relief medication (paracetamol), corticosteroid (hydrocortison 100 mg) and an antihistamine (phenergan). The starting dose was 0.2 mg/kg, which was several ten-fold lower than the highest dose tested in toxicology studies conducted in non-human primates and mice on a human-equivalent-dose (HED) base. The further dose levels were 0.6 mg/kg, 1.5 mg/kg, 3 mg/kg, and 6 mg/kg. Escalation from one dose level to the next was allowed after all patients at the previous level were evaluated for at least 7 days following the dose administration.

Toxicity was evaluated according to the National Cancer Institute (NCI) Common Toxicity Criteria (CTCAE V2) and by its intensity (i.e., mild, moderate, severe). DLT was defined as that dose which induces any Grade 3 or 4 toxicity in one or more patients, or any Grade 2 toxicity in at least 2/3 or 3/6 patients. Adverse events not judged to be related to CT-011 were not considered as toxicity in terms of these dose escalation and MTD rules.

Subsequent to drug administration, patients were monitored for safety, including adverse events and clinical and laboratory responses at 24 hours, 48 hours, and on days 7, 14, and 21.

Sample collection, parameters used to assess clinical responses, pharmacokinetic analysis, immune system activation and statistical analysis are as described in Berger et al, 2008.

Results

The main characteristics of the enrolled patients (n=17) are listed in Table 1. Patient 003, initially treated at 0.2 mg/kg, requested a repeat compassionate treatment and was treated again at 3 mg/kg. Due to the 5 month interval between the first and second treatment, the different treatments were analyzed as separate individuals. Therefore, the number of CT-011 administrations used for the analyses was 18.

TABLE 1

Patient Characteristics

| ID | Dose (mg/kg) | Age | Gender | Disease | Classification/Type | Stage | ECOG | Last Treatment prior to CT-011 therapy |
|---|---|---|---|---|---|---|---|---|
| 001 | 0.2 | 64 | F | AML | M4-Myelomonocytic | NR | 2 | Allogeneic SCT |
| 002 | 0.2 | 62 | F | NHL | ALCL | III | 3 | Irradiation |
| 003 | 0.2 | 73 | F | AML | M4-Myelomonocytic | NR | 0 | G-CSF, Erythropoietin, Blood transfusion |
| 004 | 0.6 | 60 | F | NHL | DLBCL | IV | 1 | Irradiation |
| 005 | 0.6 | 52 | M | CLL |  | C | 2 | Irradiation |
| 006 | 0.6 | 26 | F | HD |  | IVB | 0 | Irradiation |
| 007 | 1.5 | 58 | F | CLL |  | C | 2 | Mitoxantrone |
| 008 | 1.5 | 68 | F | CLL |  | A | 1 | Chlorambucil |
| 009 | 1.5 | 53 | M | AML | M2-Myelocytic | NR | 1 | Allogeneic SCT |
| 010 | 3.0 | 33 | F | AML | M4-Myelomonocytic | NR | 1 | Allogeneic SCT |

TABLE 1-continued

Patient Characteristics

| ID | Dose (mg/kg) | Age | Gender | Disease | Classification/ Type | Stage | ECOG | Last Treatment prior to CT-011 therapy |
|---|---|---|---|---|---|---|---|---|
| 011 | 3.0 | 20 | M | AML | M1-Myelocytic | NR | 0 | Mitoxantrone + cytosar |
| 012 | 3.0 | 78 | M | MDS | CMML | NR | 2 | Hydroxyurea, Thalidomide |
| 013 | 6.0 | 65 | M | AML | M4-Myelomonocytic | NR | 2 | Allogeneic SCT |
| 014 | 3.0 | 40 | F | NHL | DLBCL | II | 4 | Autologous SCT |
| 015 | 3.0 | 56 | F | NHL | Follicular Lymphoma | III | 1 | No therapy |
| 016 | 3.0 | 73 | F | AML | M4-Myelomonocytic | NR | 1 | CT-011 |
| 017 | 6.0 | 78 | M | MM | IgG; Kappa | IA | 1 | No therapy |
| 018 | 6.0 | 72 | F | AML | M4-Myelomonocytic | NR | 1 | Hydroxyurea |

Abbreviations: ALCL, Acute lymphocytic cell lymphoma, CMML, Chronic myelomonocytic leukemia, DLBCL, Diffuse large B cell lymphoma, FAB classification-French, American and British, M1, M2, M4 according to the FAB classification, NR, Non relevant, SCT, Stem cell transplantation.

No DLT was reached in the study. CT-011 was found to be safe and well tolerated with no treatment-related toxicities. No single dose MTD was found in this study.

During the study, 61% (11 of 18) of patients reported adverse events (AE), the most frequent AE observed was diarrhea, but it was concluded that it was not associated with CT-011 treatment.

Four serious adverse events occurred, all of which resulted in death and occurred in AML patients. Clinical analysis concluded that all of these patients died from fulminate resistant leukemia and none of these deaths was considered to be related to study drug.

Over the 21 days of the study no change in the average percentage of blasts in the peripheral blood of AML patients were observed with the exclusion of one AML patient (reduction in peripheral blasts from 50% to 5%). Additionally, there were no changes in disease parameters during the 21 days of the study in 2 CLL patients, 4 NHL patients and in one Multiple Myeloma patient.

The cumulative survival of all patients (n=18) at 21 days was 76%, with a 95% confidence interval of 48%-90%. No difference in mean survival time across the dose groups was noted.

Patients were followed for survival beyond the 21 days of the study. The mean survival time in the study was 25±27 weeks, ranging from 1.7 to over 77 weeks. This follow-up suggested that 6 patients exhibited apparent response to treatment with extended survival averaging at least 60 weeks. The 6 "responder" patients are represented in Table 2. There was one complete remission in patient #015 that received the fourth dose level of 3.0 mg/kg. This patient was diagnosed with stage III follicular lymphoma involving nodes below and above the diaphragm. The patient did not receive any prior treatment for her disease. In a CT scan performed during a periodic check 10 month post CT-011 treatment complete elimination of tumor masses was observed. Interestingly, the patient did not receive any further treatment during the period lapsed between CT-011 treatment and the 10 month check. The patient has demonstrated a sustained remission 68 weeks following CT-011 treatment. One minimal response was observed in an AML patient receiving CT-011 at 0.2 and 3 mg/kg). The patient progressed 61 weeks after receiving CT-011. Four patients have shown stable disease: one with HD receiving CT-011 at 0.6 mg/kg had a stable disease for 35 weeks. Two patients with CLL receiving the antibody at 0.6 mg/kg and at 1.5 mg/kg were stable for 36 weeks and over 78 weeks, respectively. A MM patient receiving CT-011 at 6.0 mg/kg showed stable disease for over 60 weeks.

TABLE 2

Clinical responses during the study follow-up period.

| Disease (Pt. No.) | Dose (mg/kg) | Observations | Overall Survival (Weeks) | Comments |
|---|---|---|---|---|
| NHL (015) | 3.0 | CR | >68 | Follicular B cell lymphoma with large tumor masses at nodes above and below the diaphragm and at the mediastinum<br>No previous treatment<br>Elimination of tumor masses by CT scan noted 10 months post CT-011 treatment |
| CLL (008) | 1.5 | SD | >78 | Binet stage A with bone marrow involvement and at ECOG 3<br>Received Leukeran about 2 years prior to CT-011<br>Stable for >17 months |
| CLL (005) | 0.6 | SD | 36 | Binet stage C with large tumor masses not responding to chemo- or radiotherapy and allogeneic SCT<br>Stable for 8 months prior to deterioration |
| HD (006) | 0.6 | SD | 35 | Classification IV B; Resistant disease, failed autologous SCT and radiotherapy<br>Stable for 8 months prior to deterioration |
| MM (017) | 6.0 | SD | >60 | Common type, IgG kappa at Stage IA and ECOG 1 who did not receive any previous treatment for his disease<br>Stable for >13 months |
| AML (003/016) | 0.2/3.0 | MR | 61 | Second dose 5 months post first dose<br>Platelet transfusion-independent for 9 months<br>Reduction in peripheral blasts (50% to 5%) on first dose |

CR = complete response;
SD = stable disease;
MR = minimal response.

DISCUSSION AND CONCLUSION

The cumulative survival of all patients at 21 days was 76%, and follow up beyond the 21 days of the study revealed mean survival of 25 weeks. Given that most of the patients were at an advanced stage of their disease, it was surprisingly and unexpectedly found that 6 patients exhibited clinical benefit with extended survival averaging 60 weeks.

The median $t_{1/2}$, of CT-011 ranged from 217 hr to 410 hr (9 to 17 days), consistent with observations with other monoclonal antibodies in humans. Interestingly, the median $t_{1/2}$ for the 6 patients with apparent clinical response (Table 2) was somewhat higher than that of the rest of the patients. Taking into account the duration of the response with an average of 60 weeks in these 6 patients and the pharmacokinetics of the antibody with a highest half life of 410 hours, it appears that in some patients, tumor-specific immunological memory is induced, leading to durable anti-tumor immune response long after the antibody has been eliminated from the blood.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A method of treating a tumor or enhancing survival of a subject having a tumor, the method comprising (i) administering to a subject in need thereof an effective amount of a humanized monoclonal antibody or a fragment thereof, wherein the antibody or the fragment thereof has all complementarity determining regions of murine monoclonal antibody BAT (mBAT-1) and a framework region (FR) from an acceptor human immunoglobulin, or modified therefrom; and (ii) administering to the subject an effective amount of at least one chemotherapeutic agent selected from the group consisting of: 5-fluorouracil, cytarabine, oxaliplatin, paclitaxel, cisplatin and combinations thereof, wherein the humanized antibody is administered between 1 and 30 days after commencing chemotherapy or according to an alternating schedule with the at least one chemotherapeutic agent; thereby treating the tumor or enhancing survival of the subject having the tumor.

2. The method according to claim 1, wherein the humanized antibody comprises: a light chain variable region selected from the group consisting of: BATRκA (SEQ ID NO: 15), BATRκB (SEQ ID NO: 16), BATRκC (SEQ ID NO: 17), and BATRκD (SEQ ID NO: 18), and a heavy chain variable region selected from the group consisting of: BATRHA (SEQ ID NO: 20), BATRHB (SEQ ID NO: 21), BATRHC (SEQ ID NO: 22), BATRHD (SEQ ID NO: 23) and BATRHE (SEQ ID NO: 24).

3. The method according to claim 1, wherein the humanized antibody comprises variable regions selected from the group consisting of: BATRHA/BATRκA (SEQ ID NO: 20/SEQ ID NO: 15), BATRHB/BATRκA (SEQ ID NO: 21/SEQ ID NO: 15), BATRHB/BATRκB (SEQ ID NO: 21/SEQ ID NO: 16), BATRHC/BATRκB (SEQ ID NO: 22/SEQ ID NO: 16), BATRHB/BATRκD (SEQ ID NO: 21/SEQ ID NO: 18), and BATRHC/BATRκD (SEQ ID NO: 22/SEQ ID NO: 18).

4. The method according to claim 3, wherein the humanized monoclonal antibody has variable regions corresponding to BATRHC/BATRκD (SEQ ID NO: 22/SEQ ID NO: 18).

5. The method according to claim 1, wherein the fragment of the humanized antibody is selected from the group consisting of: Fv, Fab', F(ab')2, and a single chain antibody; or wherein the humanized antibody or the fragment thereof retains the antitumor activity of mBAT-1.

6. The method according to claim 1, wherein the administering of the humanized antibody is carried out between 1 and 30 days after initial administration of the at least one chemotherapeutic agent.

7. The method according to claim 1, wherein the administering of the humanized antibody is carried out according to an alternating schedule with the at least one chemotherapeutic agent.

8. The method according to claim 1, wherein the administering of either or both of the humanized antibody and the at least one chemotherapeutic agent is carried out by a route selected from the group consisting of intravenous, oral, intraperitoneal, subcutaneous, isolated limb perfusion, infusion into an organ and combinations thereof.

9. The method according to claim 1, further comprising treating the subject with radiation; or further comprising assessing at least one parameter selected from the group consisting of: rate of tumor growth, tumor volume, number of metastases, tumor recurrence and combinations thereof.

10. The method according to claim 1, wherein the tumor is selected from the group consisting of colorectal carcinoma; lung carcinoma; breast carcinoma; melanoma; ovarian carcinoma; cervical carcinoma, pancreatic cancer; multiple myeloma; renal cell carcinoma; non-Hodgkin's lymphoma; Hodgkin's disease; mantle cell lymphoma; Kaposi's sarcoma; squamous cell carcinoma; basal cell carcinoma; acute myeloid leukemia (AML); chronic myelocytic leukemia (CML); acute lymphocytic leukemia (ALL), chronic lymphocytic leukemia (CLL).

11. The method according to claim 1, wherein the light chain variable region of the humanized monoclonal antibody is SEQ ID NO: 18, the heavy chain variable region of the humanized monoclonal antibody is SEQ ID NO: 22, the chemotherapeutic agent is paclitaxel, the tumor is breast carcinoma and the humanized antibody is administered between 1 and 30 days after commencing chemotherapy.

12. The method according to claim 1, wherein said method reduces or prevents tumor recurrence.

13. A method of improving tolerability to at least one chemotherapeutic agent, the method comprising administering to a subject in need thereof an effective amount of a humanized monoclonal antibody BAT (mBAT-1) or a fragment thereof, wherein the antibody or the fragment thereof has all complementarity determining regions of mBAT-1 and a framework region (FR) from an acceptor human immunoglobulin, or modified therefrom; wherein the subject is undergoing chemotherapy with at least one chemotherapeutic agent; thereby improving tolerability to said at least one chemotherapeutic agent, wherein the at least one chemotherapeutic agent is selected from the group consisting of: 5-fluorouracil, cytarabine, oxaliplatin, paclitaxel, cisplatin and combinations thereof, and the humanized antibody is administered between 1 and 30 days after commencing chemotherapy or according to an alternating schedule with the at least one chemotherapeutic agent.

14. The method according to claim 13, wherein the humanized antibody comprises: a light chain variable region selected from the group consisting of: BATRκA (SEQ ID NO: 15), BATRκB (SEQ ID NO: 16), BATRκC (SEQ ID NO: 17), and BATRκD (SEQ ID NO: 18), and a heavy chain variable region selected from the group consisting of: BATRHA (SEQ ID NO: 20), BATRHB (SEQ ID NO: 21), BATRHC (SEQ ID NO: 22), BATRHD (SEQ ID NO: 23) and BATRHE (SEQ ID NO: 24).

15. The method according to claim 14, wherein the humanized antibody comprises variable regions selected from the group consisting of: BATRHA/BATRκA (SEQ ID NO: 20/SEQ ID NO: 15), BATRHB/BATRκA (SEQ ID NO: 21/SEQ ID NO: 15), BATRHB/BATRκB (SEQ ID NO: 21/SEQ ID NO: 16), BATRHC/BATRκB (SEQ ID NO: 22/SEQ ID NO: 16), BATRHB/BATRκD (SEQ ID NO: 21/SEQ ID NO: 18), and BATRHC/BATRκD (SEQ ID NO: 22/SEQ ID NO: 18).

16. The method according to claim 15, wherein the humanized monoclonal has variable regions corresponding to BATRHC/BATRκD (SEQ ID NO: 22/SEQ ID NO: 18).

17. The method according to claim 13, wherein the fragment of the humanized antibody is selected from the group consisting of: Fv, Fab', F(ab')2, and a single chain antibody; or wherein the humanized antibody or the fragment thereof retains the antitumor activity of mBAT-1.

18. The method according to claim 13, wherein the administering of the humanized antibody is carried out between 1 and 30 days after initial administration of the at least one chemotherapeutic agent.

19. The method according to claim 13, wherein the administering of either or both of the humanized antibody and the at least one chemotherapeutic agent is carried out by a route selected from the group consisting of intravenous, oral, intraperitoneal, subcutaneous, isolated limb perfusion, infusion into an organ and combinations thereof; or wherein the chemotherapy is for treatment of a tumor selected from the group consisting of colorectal carcinoma; lung carcinoma; breast carcinoma; melanoma; ovarian carcinoma; cervical carcinoma, pancreatic cancer; multiple myeloma; renal cell carcinoma; non-Hodgkin's lymphoma; Hodgkin's disease; mantle cell lymphoma; Kaposi's sarcoma; squamous cell carcinoma; basal cell carcinoma; acute myeloid leukemia (AML); chronic myelocytic leukemia (CML); acute lymphocytic leukemia (ALL), and chronic lymphocytic leukemia (CLL).

20. The method according to claim 13, wherein the light chain variable region of the humanized monoclonal antibody is SEQ ID NO: 18, the heavy chain variable region of the humanized monoclonal antibody is SEQ ID NO: 22, the chemotherapeutic agent is paclitaxel, the tumor is breast carcinoma and the humanized antibody is administered between 1 and 30 days after commencing chemotherapy.

* * * * *

UNITED STATES PATENT AND TRADEMARK OFFICE
CERTIFICATE OF CORRECTION

PATENT NO. : 9,309,308 B2
APPLICATION NO. : 14/264338
DATED : April 12, 2016
INVENTOR(S) : Rotem-Yehudar et al.

Page 1 of 1

It is certified that error appears in the above-identified patent and that said Letters Patent is hereby corrected as shown below:

Title Page:
Item (62), Related U.S. Application Data, before "of application No. 12/867,208, filed as", change "Division" to -- Continuation --.

Signed and Sealed this
Twenty-sixth Day of July, 2016

Michelle K. Lee
*Director of the United States Patent and Trademark Office*

SEQUENCE LISTING

```
<160> NUMBER OF SEQ ID NOS: 193

<210> SEQ ID NO 1
<211> LENGTH: 23
<212> TYPE: PRT
<213> ORGANISM: Artificial sequence
<220> FEATURE:
<223> OTHER INFORMATION: Synthetic peptide

<400> SEQUENCE: 1

Glu Ile Val Leu Thr Gln Ser Pro Ser Ser Leu Ser Ala Ser Val Gly
1               5                   10                  15

Asp Arg Val Thr Ile Thr Cys
            20

<210> SEQ ID NO 2
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = Phe or Tyr
<220> FEATURE:
<221> NAME/KEY: MISC_FEATURE
<222> LOCATION: (13)..(13)
<223> OTHER INFORMATION: Xaa = Trp or Leu

<400> SEQUENCE: 2

Trp Xaa Gln Gln Lys Pro Gly Lys Ala Pro Lys Leu Xaa Ile Tyr
1               5                   10                  15

<210> SEQ ID NO 3
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: Xaa = Asp or Ser
<220> FEATURE:
<221> NAME/KEY: MISC_FEATURE
<222> LOCATION: (15)..(15)
<223> OTHER INFORMATION: Xaa = Tyr or Phe
<220> FEATURE:
<221> NAME/KEY: MISC_FEATURE
<222> LOCATION: (16)..(16)
<223> OTHER INFORMATION: Xaa = Cys or Thr
```

```
<400> SEQUENCE: 3

Gly Val Pro Ser Arg Phe Ser Gly Ser Gly Ser Gly Thr Xaa Xaa Xaa
1               5                   10                  15

Leu Thr Ile Asn Ser Leu Gln Pro Glu Asp Phe Ala Thr Tyr Tyr Cys
            20                  25                  30

<210> SEQ ID NO 4
<211> LENGTH: 10
<212> TYPE: PRT
<213> ORGANISM: Artificial sequence
<220> FEATURE:
<223> OTHER INFORMATION: Synthetic peptide

<400> SEQUENCE: 4

Phe Gly Gly Gly Thr Lys Leu Glu Ile Lys
1               5                   10

<210> SEQ ID NO 5
<211> LENGTH: 30
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = Ile or Val
<220> FEATURE:
<221> NAME/KEY: MISC_FEATURE
<222> LOCATION: (28)..(28)
<223> OTHER INFORMATION: Xaa = Thr or ser
<220> FEATURE:
<221> NAME/KEY: MISC_FEATURE
<222> LOCATION: (30)..(30)
<223> OTHER INFORMATION: Xaa = Thr or Ser

<400> SEQUENCE: 5

Gln Xaa Gln Leu Val Gln Ser Gly Ser Glu Leu Lys Lys Pro Gly Ala
1               5                   10                  15

Ser Val Lys Ile Ser Cys Lys Ala Ser Gly Tyr Xaa Phe Xaa
            20                  25                  30

<210> SEQ ID NO 6
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa = Arg or Lys
<220> FEATURE:
<221> NAME/KEY: MISC_FEATURE
<222> LOCATION: (11)..(11)
<223> OTHER INFORMATION: Xaa = Gln or Lys

<400> SEQUENCE: 6

Trp Val Xaa Gln Ala Pro Gly Gln Gly Leu Xaa Trp Met Gly
1               5                   10

<210> SEQ ID NO 7
<211> LENGTH: 32
<212> TYPE: PRT
<213> ORGANISM: Artificial sequence
<220> FEATURE:
<223> OTHER INFORMATION: Synthetic peptide
<220> FEATURE:
```

```
<221> NAME/KEY: MISC_FEATURE
<222> LOCATION: (3)..(3)
<223> OTHER INFORMATION: Xaa = Val or Ala
<220> FEATURE:
<221> NAME/KEY: MISC_FEATURE
<222> LOCATION: (11)..(11)
<223> OTHER INFORMATION: Xaa = Asn or Ser
<220> FEATURE:
<221> NAME/KEY: MISC_FEATURE
<222> LOCATION: (21)..(21)
<223> OTHER INFORMATION: Xaa = Thr or Asn
<220> FEATURE:
<221> NAME/KEY: MISC_FEATURE
<222> LOCATION: (31)..(31)
<223> OTHER INFORMATION: Xaa = Val or Ala
<220> FEATURE:
<221> NAME/KEY: MISC_FEATURE
<222> LOCATION: (32)..(32)
<223> OTHER INFORMATION: Xaa = Arg or Lys

<400> SEQUENCE: 7

Arg Phe Xaa Phe Ser Leu Asp Thr Ser Val Xaa Thr Ala Tyr Leu Gln
1               5                   10                  15

Ile Thr Ser Leu Xaa Ala Glu Asp Thr Gly Met Tyr Phe Cys Xaa Xaa
            20                  25                  30

<210> SEQ ID NO 8
<211> LENGTH: 11
<212> TYPE: PRT
<213> ORGANISM: Artificial sequence
<220> FEATURE:
<223> OTHER INFORMATION: Synthetic peptide

<400> SEQUENCE: 8

Trp Gly Gln Gly Thr Leu Val Thr Val Ser Ser
1               5                   10

<210> SEQ ID NO 9
<211> LENGTH: 10
<212> TYPE: PRT
<213> ORGANISM: Artificial sequence
<220> FEATURE:
<223> OTHER INFORMATION: Synthetic peptide

<400> SEQUENCE: 9

Ser Ala Arg Ser Ser Val Ser Tyr Met His
1               5                   10

<210> SEQ ID NO 10
<211> LENGTH: 7
<212> TYPE: PRT
<213> ORGANISM: Artificial sequence
<220> FEATURE:
<223> OTHER INFORMATION: Synthetic peptide

<400> SEQUENCE: 10

Arg Thr Ser Asn Leu Ala Ser
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic peptide

<400> SEQUENCE: 11

Gln Gln Arg Ser Ser Phe Pro Leu Thr
1               5
```

```
<210> SEQ ID NO 12
<211> LENGTH: 5
<212> TYPE: PRT
<213> ORGANISM: Artificial sequence
<220> FEATURE:
<223> OTHER INFORMATION: Synthetic peptide

<400> SEQUENCE: 12

Asn Tyr Gly Met Asn
1               5

<210> SEQ ID NO 13
<211> LENGTH: 17
<212> TYPE: PRT
<213> ORGANISM: Artificial sequence
<220> FEATURE:
<223> OTHER INFORMATION: Synthetic peptide

<400> SEQUENCE: 13

Trp Ile Asn Thr Asp Ser Gly Glu Ser Thr Tyr Ala Glu Glu Phe Lys
1               5                   10                  15

Gly

<210> SEQ ID NO 14
<211> LENGTH: 8
<212> TYPE: PRT
<213> ORGANISM: Artificial sequence
<220> FEATURE:
<223> OTHER INFORMATION: Synthetic peptide

<400> SEQUENCE: 14

Val Gly Tyr Asp Ala Leu Asp Tyr
1               5

<210> SEQ ID NO 15
<211> LENGTH: 106
<212> TYPE: PRT
<213> ORGANISM: Artificial sequence
<220> FEATURE:
<223> OTHER INFORMATION: Synthetic peptide

<400> SEQUENCE: 15

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
                20                  25                  30

His Trp Tyr Gln Gln Lys Pro Gly Lys Ala Pro Lys Leu Leu Ile Tyr
            35                  40                  45

Arg Thr Ser Asn Leu Ala Ser Gly Val Pro Ser Arg Phe Ser Gly Ser
        50                  55                  60

Gly Ser Gly Thr Asp Phe Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 16
<211> LENGTH: 106
<212> TYPE: PRT
<213> ORGANISM: Artificial sequence
<220> FEATURE:
```

<223> OTHER INFORMATION: Synthetic peptide

<400> SEQUENCE: 16

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 17
<211> LENGTH: 106
<212> TYPE: PRT
<213> ORGANISM: Artificial sequence
<220> FEATURE:
<223> OTHER INFORMATION: Synthetic peptide

<400> SEQUENCE: 17

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 18
<211> LENGTH: 106
<212> TYPE: PRT
<213> ORGANISM: Artificial sequence
<220> FEATURE:
<223> OTHER INFORMATION: Synthetic peptide

<400> SEQUENCE: 18

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu

```
                65                  70                  75                  80
Asp Phe Ala Thr Tyr Tyr Cys Gln Gln Arg Ser Ser Phe Pro Leu Thr
                    85                  90                  95

Phe Gly Gly Gly Thr Lys Leu Glu Ile Lys
                100                 105

<210> SEQ ID NO 19
<211> LENGTH: 128
<212> TYPE: PRT
<213> ORGANISM: Artificial sequence
<220> FEATURE:
<223> OTHER INFORMATION: Synthetic peptide

<400> SEQUENCE: 19

Met Asp Leu Gln Val Gln Ile Ile Ser Phe Leu Leu Ile Ser Ala Ser
1               5                   10                  15

Val Ile Met Ser Arg Gly Gln Ile Val Leu Thr Gln Ser Pro Ala Ile
                20                  25                  30

Met Ser Ala Ser Pro Gly Glu Lys Val Thr Ile Thr Cys Ser Ala Arg
            35                  40                  45

Ser Ser Val Ser Tyr Met His Trp Phe Gln Gln Lys Pro Gly Thr Ser
        50                  55                  60

Pro Lys Leu Trp Ile Tyr Arg Thr Ser Asn Leu Ala Ser Gly Val Pro
65                  70                  75                  80

Ala Arg Phe Ser Gly Ser Gly Ser Gly Thr Ser Tyr Cys Leu Thr Ile
                85                  90                  95

Ser Arg Met Glu Ala Glu Asp Ala Ala Thr Tyr Tyr Cys Gln Gln Arg
                100                 105                 110

Ser Ser Phe Pro Leu Thr Phe Gly Ser Gly Thr Lys Leu Glu Ile Lys
        115                 120                 125

<210> SEQ ID NO 20
<211> LENGTH: 117
<212> TYPE: PRT
<213> ORGANISM: Artificial sequence
<220> FEATURE:
<223> OTHER INFORMATION: Synthetic peptide

<400> SEQUENCE: 20

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Ser Phe Ser Asn Tyr
                20                  25                  30

Gly Met Asn Trp Val Arg Gln Ala Pro Gly Gln Gly Leu Gln Trp Met
            35                  40                  45

Gly Trp Ile Asn Thr Asp Ser Gly Glu Ser Thr Tyr Ala Glu Glu Phe
        50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Val Gly Tyr Asp Ala Leu Asp Tyr Trp Gly Gln Gly Thr Leu
                100                 105                 110

Val Thr Val Ser Ser
        115

<210> SEQ ID NO 21
<211> LENGTH: 117
```

<212> TYPE: PRT
<213> ORGANISM: Artificial sequence
<220> FEATURE:
<223> OTHER INFORMATION: Synthetic peptide

<400> SEQUENCE: 21

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
                20                  25                  30

Gly Met Asn Trp Val Arg Gln Ala Pro Gly Gln Gly Leu Gln Trp Met
            35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Val Gly Tyr Asp Ala Leu Asp Tyr Trp Gly Gln Gly Thr Leu
                100                 105                 110

Val Thr Val Ser Ser
        115

<210> SEQ ID NO 22
<211> LENGTH: 117
<212> TYPE: PRT
<213> ORGANISM: Artificial sequence
<220> FEATURE:
<223> OTHER INFORMATION: Synthetic peptide

<400> SEQUENCE: 22

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
                20                  25                  30

Gly Met Asn Trp Val Arg Gln Ala Pro Gly Gln Gly Leu Gln Trp Met
            35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
                100                 105                 110

Val Thr Val Ser Ser
        115

<210> SEQ ID NO 23
<211> LENGTH: 117
<212> TYPE: PRT
<213> ORGANISM: Artificial sequence
<220> FEATURE:
<223> OTHER INFORMATION: Synthetic peptide

<400> SEQUENCE: 23

Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr

```
            20                  25                  30
Gly Met Asn Trp Val Arg Gln Ala Pro Gly Gln Gly Leu Gln Trp Met
         35                  40                  45

Gly Trp Ile Asn Thr Asp Ser Gly Glu Ser Thr Tyr Ala Glu Glu Phe
     50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
             85                  90                  95

Val Arg Val Gly Tyr Asp Ala Leu Asp Tyr Trp Gly Gln Gly Thr Leu
           100                 105                 110

Val Thr Val Ser Ser
        115

<210> SEQ ID NO 24
<211> LENGTH: 117
<212> TYPE: PRT
<213> ORGANISM: Artificial sequence
<220> FEATURE:
<223> OTHER INFORMATION: Synthetic peptide

<400> SEQUENCE: 24

Gln Ile Gln Leu Val Gln Ser Gly Ser Glu Leu Lys Lys Pro Gly Ala
1               5                  10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
         35                  40                  45

Gly Trp Ile Asn Thr Asp Ser Gly Glu Ser Thr Tyr Ala Glu Glu Phe
     50                  55                  60

Lys Gly Arg Phe Ala Phe Ser Leu Asp Thr Ser Val Asn Thr Ala Tyr
65                  70                  75                  80

Leu Gln Ile Thr Ser Leu Asn Ala Glu Asp Thr Gly Met Tyr Phe Cys
             85                  90                  95

Val Arg Val Gly Tyr Asp Ala Leu Asp Tyr Trp Gly Gln Gly Thr Leu
           100                 105                 110

Val Thr Val Ser Ser
        115

<210> SEQ ID NO 25
<211> LENGTH: 384
<212> TYPE: DNA
<213> ORGANISM: Artificial sequence
<220> FEATURE:
<223> OTHER INFORMATION: Synthetic polynucleotide

<400> SEQUENCE: 25
atggatttac aggtgcagat tatcagcttc ctgctaatca gtgcctcagt cataatgtcc      60
agaggacaaa ttgttctcac ccagtctcca gcaatcatgt ctgcatctcc aggggagaag     120
gtcaccataa cctgcagtgc caggtcaagt gtaagttaca tgcactggtt ccagcagaag     180
ccaggcactt ctcccaaact ctggatttat aggacatcca acctggcttc tggagtccct     240
gctcgcttca gtggcagtgg atctgggacc tcttactgtc tcacaatcag ccgaatggag     300
gctgaagatg ctgccactta ttactgccag caaaggagta gtttcccact cacgttcggc     360
tcggggacaa agttggaaat aaaa                                            384
```

<210> SEQ ID NO 26
<211> LENGTH: 136
<212> TYPE: PRT
<213> ORGANISM: Artificial sequence
<220> FEATURE:
<223> OTHER INFORMATION: Synthetic peptide

<400> SEQUENCE: 26

```
Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asp Ser Gly Glu Ser Thr Tyr Ala
65                  70                  75                  80

Glu Glu Phe Lys Gly Arg Phe Ala Phe Ser Leu Glu Thr Ser Ala Asn
                85                  90                  95

Thr Ala Tyr Leu Gln Ile Asn Asn Leu Asn Asn Glu Asp Thr Ala Thr
            100                 105                 110

Tyr Phe Cys Val Arg Val Gly Tyr Asp Ala Leu Asp Tyr Trp Gly Gln
        115                 120                 125

Gly Thr Ser Val Thr Val Ser Ser
    130                 135
```

<210> SEQ ID NO 27
<211> LENGTH: 408
<212> TYPE: DNA
<213> ORGANISM: Artificial sequence
<220> FEATURE:
<223> OTHER INFORMATION: Synthetic polynucleotide

<400> SEQUENCE: 27

```
atggcttggg tgtggacctt gctattcctg atggcagctg cccaaagtat ccaagcacag    60
atccagttgg tgcagtctgg acctgagttg aagaagcctg gagagacagt caagatctcc   120
tgcaaggctt ctggatatac tttcacaaac tatggaatga actgggtgaa gcaggctcca   180
ggaaagggtt taaagtggat gggctggata acaccgaca gtggagagtc aacatatgct   240
gaagagttca agggacggtt tgccttctct ttggaaacct ctgccaacac tgcctatttg   300
cagatcaaca acctcaacaa tgaggacacg gctacatatt tctgtgtgag agtcggctac   360
gatgctttgg actactgggg tcaaggaacc tcagtcaccg tctcctca                408
```

<210> SEQ ID NO 28
<211> LENGTH: 107
<212> TYPE: PRT
<213> ORGANISM: Artificial sequence
<220> FEATURE:
<223> OTHER INFORMATION: Synthetic peptide

<400> SEQUENCE: 28

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
            35                  40                  45
```

```
Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Gln Gln Thr Asn Ser Phe Pro Leu
                 85                  90                  95

Thr Phe Gly Gly Gly Thr Lys Leu Glu Ile Lys
            100                 105
```

<210> SEQ ID NO 29
<211> LENGTH: 120
<212> TYPE: PRT
<213> ORGANISM: Artificial sequence
<220> FEATURE:
<223> OTHER INFORMATION: Synthetic peptide

<400> SEQUENCE: 29

```
Gln Val Gln Leu Val Gln Ser Gly Ser Glu Leu Lys Lys Pro Gly Ala
 1               5                  10                  15

Ser Val Lys Ile Ser Cys Lys Ala Ser Gly Tyr Ser Phe Ser Ser His
             20                  25                  30

Ala Ile Asn Trp Val Arg Gln Ala Pro Gly Gln Gly Leu Gln Trp Met
         35                  40                  45

Gly Trp Ile Asn Thr Asn Thr Gly Ser Pro Thr Tyr Ala Gln Gly Phe
     50                  55                  60

Thr Gly Arg Phe Val Phe Ser Leu Asp Thr Ser Val Ser Thr Ala Tyr
 65                  70                  75                  80

Leu Gln Ile Thr Ser Leu Thr Ala Glu Asp Thr Gly Met Tyr Phe Cys
                 85                  90                  95

Ala Lys Glu Ser His Ser Ser Ala Leu Asp Leu Asp Tyr Trp Gly Gln
            100                 105                 110

Gly Thr Leu Val Thr Val Ser Ser
        115                 120
```

<210> SEQ ID NO 30
<211> LENGTH: 43
<212> TYPE: DNA
<213> ORGANISM: Artificial sequence
<220> FEATURE:
<223> OTHER INFORMATION: Synthetic polynucleotide

<400> SEQUENCE: 30
cccaagcttg ccgccaccat ggacatgagg gtccccgctc agc       43

<210> SEQ ID NO 31
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 31
tcctggggct cctgctgctc tggctcccag gtgccaaatg       40

<210> SEQ ID NO 32
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 32
tgaaattgtg ttgacgcagt ctccatcctc cctgtctgca                        40

<210> SEQ ID NO 33
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 33
tctgtaggag acagagtcac catcacttgc agtgccaggt                        40

<210> SEQ ID NO 34
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 34
caagtgtaag ttacatgcac tggtatcagc agaaaccagg                        40

<210> SEQ ID NO 35
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 35
gaaagcccct aagctcctga tctataggac atccaacctg                        40

<210> SEQ ID NO 36
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 36
gcttctgggg tcccatctag attcagcggc agtggatctg                        40

<210> SEQ ID NO 37
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 37
ggacagattt cactctcacc atcaacagcc tgcagcctga                        40

<210> SEQ ID NO 38
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 38
agattttgca acttactatt gccagcaaag gagtagtttc                        40

<210> SEQ ID NO 39
<211> LENGTH: 55
<212> TYPE: DNA

<213> ORGANISM: Artificial sequence
<220> FEATURE:
<223> OTHER INFORMATION: Synthetic polynucleotide

<400> SEQUENCE: 39
ccactcacgt tcggcggagg gaccaagctg gagatcaaac gtgagtggat ccgcg         55

<210> SEQ ID NO 40
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 40
gagcagcagg agccccagga gctgagcggg gaccctcatg         40

<210> SEQ ID NO 41
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 41
actgcgtcaa cacaatttca catttggcac ctgggagcca         40

<210> SEQ ID NO 42
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 42
gtgactctgt ctcctacaga tgcagacagg gaggatggag         40

<210> SEQ ID NO 43
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 43
gtgcatgtaa cttacacttg acctggcact gcaagtgatg         40

<210> SEQ ID NO 44
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 44
tcaggagctt agggggctttc cctggtttct gctgatacca         40

<210> SEQ ID NO 45
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 45
ctagatggga ccccagaaagc caggttggat gtcctataga         40

<210> SEQ ID NO 46
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 46
ggtgagagtg aaatctgtcc cagatccact gccgctgaat                                40

<210> SEQ ID NO 47
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 47
aatagtaagt tgcaaaatct tcaggctgca ggctgttgat                                40

<210> SEQ ID NO 48
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 48
cctccgccga acgtgagtgg gaaactactc ctttgctggc                                40

<210> SEQ ID NO 49
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 49
cgcggatcca ctcacgtttg atctccagct tggtc                                     35

<210> SEQ ID NO 50
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 50
caagtgtaag ttacatgcac tggttccagc agaaaccagg                                40

<210> SEQ ID NO 51
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 51
gaaagcccct aagctctgga tctataggac atccaacctg                                40

<210> SEQ ID NO 52
<211> LENGTH: 40
<212> TYPE: DNA
<213> ORGANISM: Artificial sequence
<220> FEATURE:

```
<223> OTHER INFORMATION: Synthetic polynucleotide

<400> SEQUENCE: 52
ggacagatta cactctcacc atcaacagcc tgcagcctga                              40

<210> SEQ ID NO 53
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 53
tccagagctt aggggctttc cctggtttct gctggaacca                              40

<210> SEQ ID NO 54
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 54
ggtgagagtg taatctgtcc cagatccact gccgctgaac                              40

<210> SEQ ID NO 55
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 55
ggtgagacag taagatgtcc cagatccact gccgctgaac                              40

<210> SEQ ID NO 56
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 56
ggacatctta ctgtctcacc atcaacagcc tgcagcctga                              40

<210> SEQ ID NO 57
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 57
cccaagcttg ccgccaccat ggactggacc tggaggatcc                              40

<210> SEQ ID NO 58
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 58
tcttcttggt ggcagcagca acaggtgccc act                                    33
```

```
<210> SEQ ID NO 59
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 59
cccaggtgca gctggtgcaa tctgggtctg agcttaagaa                          40

<210> SEQ ID NO 60
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 60
gcctggggcc tcagtgaaga tctcctgcaa ggcttctgga                          40

<210> SEQ ID NO 61
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 61
tatagcttca gtaactatgg aatgaactgg gtgcgacagg                          40

<210> SEQ ID NO 62
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 62
cccctggaca agggcttcag tggatgggat ggataaacac                          40

<210> SEQ ID NO 63
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 63
cgacagtgga gagtcaacat atgctgaaga gttcaaggga                          40

<210> SEQ ID NO 64
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 64
cggtttgtct tctccttgga cacctctgtc agcacggcat                          40

<210> SEQ ID NO 65
<211> LENGTH: 40
<212> TYPE: DNA
<213> ORGANISM: Artificial sequence
<220> FEATURE:
<223> OTHER INFORMATION: Synthetic polynucleotide
```

<400> SEQUENCE: 65
atctgcagat caccagcctc acggctgagg acactggcat        40

<210> SEQ ID NO 66
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 66
gtatttctgt gcgaaagtcg gctacgatgc tttgg        35

<210> SEQ ID NO 67
<211> LENGTH: 54
<212> TYPE: DNA
<213> ORGANISM: Artificial sequence
<220> FEATURE:
<223> OTHER INFORMATION: Synthetic polynucleotide

<400> SEQUENCE: 67
actactgggg ccagggaacc ctggtcaccg tctcctcagg tgagtggatc cgcg        54

<210> SEQ ID NO 68
<211> LENGTH: 45
<212> TYPE: DNA
<213> ORGANISM: Artificial sequence
<220> FEATURE:
<223> OTHER INFORMATION: Synthetic polynucleotide

<400> SEQUENCE: 68
tgctgccacc aagaagagga tccttccagg tggagtccat ggtgg        45

<210> SEQ ID NO 69
<211> LENGTH: 36
<212> TYPE: DNA
<213> ORGANISM: Artificial sequence
<220> FEATURE:
<223> OTHER INFORMATION: Synthetic polynucleotide

<400> SEQUENCE: 69
ttgcaccagc tgcacctggg agtgggcacc tgttgc        36

<210> SEQ ID NO 70
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 70
tcttcactga ggccccaggc ttcttaagct cagacccaga        40

<210> SEQ ID NO 71
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 71
ccatagttac tgaagctata tccagaagct tgcaggaga        39

<210> SEQ ID NO 72
<211> LENGTH: 40

```
<212> TYPE: DNA
<213> ORGANISM: Artificial sequence
<220> FEATURE:
<223> OTHER INFORMATION: Synthetic polynucleotide

<400> SEQUENCE: 72
ctgaagccct tgtccagggg cctgtcgcac ccagttcatt                    40

<210> SEQ ID NO 73
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 73
atgttgactc tccactgtcg gtgtttatcc atcccatcca                    40

<210> SEQ ID NO 74
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 74
tccaaggaga agacaaaccg tcccttgaac tcttcagcat                    40

<210> SEQ ID NO 75
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 75
gaggctggtg atctgcagat atgccgtgct gacagaggtg                    40

<210> SEQ ID NO 76
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 76
cgactttcgc acagaaatac atgccagtgt cctcagccgt                    40

<210> SEQ ID NO 77
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 77
ttccctggcc ccagtagtcc aaagcatcgt agc                           33

<210> SEQ ID NO 78
<211> LENGTH: 36
<212> TYPE: DNA
<213> ORGANISM: Artificial sequence
<220> FEATURE:
<223> OTHER INFORMATION: Synthetic polynucleotide

<400> SEQUENCE: 78
```
cgcggatcca ctcacctgag gagacggtga ccaggg        36

<210> SEQ ID NO 79
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 79
tatactttca caaactatgg aatgaactgg gtgcgacagg        40

<210> SEQ ID NO 80
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 80
ccatagtttg tgaaagtata tccagaagcc ttgcaggaga        40

<210> SEQ ID NO 81
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 81
cggtttgtct tctccttgga cacctctgtc aacacggcat        40

<210> SEQ ID NO 82
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 82
gtatttctgt gtgagagtcg gctacgatgc tttgg        35

<210> SEQ ID NO 83
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 83
cgactctcac acagaaatac atgccagtgt cctcagccgt        40

<210> SEQ ID NO 84
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 84
atctgcagat caccagcctc aacgctgagg acactggcat        40

<210> SEQ ID NO 85
<211> LENGTH: 40
<212> TYPE: DNA
<213> ORGANISM: Artificial sequence

```
<220> FEATURE:
<223> OTHER INFORMATION: Synthetic polynucleotide

<400> SEQUENCE: 85
gaggctggtg atctgcagat atgccgtgtt gacagaggtg                          40

<210> SEQ ID NO 86
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 86
tatactttca caaactatgg aatgaactgg gtgaagcagg                          40

<210> SEQ ID NO 87
<211> LENGTH: 412
<212> TYPE: DNA
<213> ORGANISM: Artificial sequence
<220> FEATURE:
<223> OTHER INFORMATION: Synthetic polynucleotide

<400> SEQUENCE: 87
aagcttgccg ccaccatgga catgagggtc cccgctcagc tcctggggct cctgctgctc    60
tggctcccag gtgccaaatg tgaaattgtg ttgacgcagt ctccatcctc cctgtctgca   120
tctgtaggag acagagtcac catcacttgc agtgccaggt caagtgtaag ttacatgcac   180
tggtatcagc agaaaccagg gaaagcccct aagctcctga tctataggac atccaacctg   240
gcttctgggg tcccatctag attcagcggc agtggatctg ggacagattt cactctcacc   300
atcaacagcc tgcagcctga agattttgca acttactatt gccagcaaag gagtagtttc   360
ccactcacgt tcggcggagg gaccaagctg gagatcaaac gtgagtggat cc           412

<210> SEQ ID NO 88
<211> LENGTH: 412
<212> TYPE: DNA
<213> ORGANISM: Artificial sequence
<220> FEATURE:
<223> OTHER INFORMATION: Synthetic polynucleotide

<400> SEQUENCE: 88
aagcttgccg ccaccatgga catgagggtc cccgctcagc tcctggggct cctgctgctc    60
tggctcccag gtgccaaatg tgaaattgtg ttgacgcagt ctccatcctc cctgtctgca   120
tctgtaggag acagagtcac catcacttgc agtgccaggt caagtgtaag ttacatgcac   180
tggttccagc agaaaccagg gaaagcccct aagctctgga tctataggac atccaacctg   240
gcttctgggg tcccatctag attcagcggc agtggatctg ggacagatta cactctcacc   300
atcaacagcc tgcagcctga agattttgca acttactatt gccagcaaag gagtagtttc   360
ccactcacgt tcggcggagg gaccaagctg gagatcaaac gtgagtggat cc           412

<210> SEQ ID NO 89
<211> LENGTH: 412
<212> TYPE: DNA
<213> ORGANISM: Artificial sequence
<220> FEATURE:
<223> OTHER INFORMATION: Synthetic polynucleotide

<400> SEQUENCE: 89
aagcttgccg ccaccatgga catgagggtc cccgctcagc tcctggggct cctgctgctc    60
```

| | |
|---|---|
| tggctcccag gtgccaaatg tgaaattgtg ttgacgcagt ctccatcctc cctgtctgca | 120 |
| tctgtaggag acagagtcac catcacttgc agtgccaggt caagtgtaag ttacatgcac | 180 |
| tggttccagc agaaaccagg gaaagcccct aagctctgga tctataggac atccaacctg | 240 |
| gcttctgggg tcccatctag attcagcggc agtggatctg ggacatctta ctgtctcacc | 300 |
| atcaacagcc tgcagcctga agattttgca acttactatt gccagcaaag gagtagtttc | 360 |
| ccactcacgt tcggcggagg gaccaagctg gagatcaaac gtgagtggat cc | 412 |

```
<210> SEQ ID NO 90
<211> LENGTH: 436
<212> TYPE: DNA
<213> ORGANISM: Artificial sequence
<220> FEATURE:
<223> OTHER INFORMATION: Synthetic polynucleotide

<400> SEQUENCE: 90
```

| | |
|---|---|
| aagcttgccg ccaccatgga ctggacctgg aggatcctct tcttggtggc agcagcaaca | 60 |
| ggtgcccact cccaggtgca gctggtgcaa tctgggtctg agcttaagaa gcctggggcc | 120 |
| tcagtgaaga tctcctgcaa ggcttctgga tatactttca caaactatgg aatgaactgg | 180 |
| gtgcgacagg cccctggaca agggcttcag tggatgggat ggataaacac cgacagtgga | 240 |
| gagtcaacat atgctgaaga gttcaaggga cggtttgtct ctccttgga cacctctgtc | 300 |
| aacacggcat atctgcagat caccagcctc acggctgagg acactggcat gtatttctgt | 360 |
| gtgagagtcg gctacgatgc tttggactac tggggccagg gaaccctggt caccgtctcc | 420 |
| tcaggtgagt ggatcc | 436 |

```
<210> SEQ ID NO 91
<211> LENGTH: 436
<212> TYPE: DNA
<213> ORGANISM: Artificial sequence
<220> FEATURE:
<223> OTHER INFORMATION: Synthetic polynucleotide

<400> SEQUENCE: 91
```

| | |
|---|---|
| aagcttgccg ccaccatgga ctggacctgg aggatcctct tcttggtggc agcagcaaca | 60 |
| ggtgcccact cccaggtgca gctggtgcaa tctgggtctg agcttaagaa gcctggggcc | 120 |
| tcagtgaaga tctcctgcaa ggcttctgga tatactttca caaactatgg aatgaactgg | 180 |
| gtgcgacagg cccctggaca agggcttcag tggatgggat ggataaacac cgacagtgga | 240 |
| gagtcaacat atgctgaaga gttcaaggga cggtttgtct ctccttgga cacctctgtc | 300 |
| agcacggcat atctgcagat caccagcctc acggctgagg acactggcat gtatttctgt | 360 |
| gcgaaagtcg gctacgatgc tttggactac tggggccagg gaaccctggt caccgtctcc | 420 |
| tcaggtgagt ggatcc | 436 |

```
<210> SEQ ID NO 92
<211> LENGTH: 436
<212> TYPE: DNA
<213> ORGANISM: Artificial sequence
<220> FEATURE:
<223> OTHER INFORMATION: Synthetic polynucleotide

<400> SEQUENCE: 92
```

| | |
|---|---|
| aagcttgccg ccaccatgga ctggacctgg aggatcctct tcttggtggc agcagcaaca | 60 |
| ggtgcccact cccaggtgca gctggtgcaa tctgggtctg agcttaagaa gcctggggcc | 120 |
| tcagtgaaga tctcctgcaa ggcttctgga tatactttca caaactatgg aatgaactgg | 180 |

-continued

```
gtgcgacagg cccctggaca agggcttcag tggatgggat ggataaacac cgacagtgga    240
gagtcaacat atgctgaaga gttcaaggga cggtttgtct tctccttgga cacctctgtc    300
agcacggcat atctgcagat caccagcctc acggctgagg acactggcat gtatttctgt    360
gcgaaagtcg gctacgatgc tttggactac tggggccagg aaccctggt caccgtctcc    420 tcaggtgagt ggatcc                                                    436
```

<210> SEQ ID NO 93
<211> LENGTH: 10259
<212> TYPE: DNA
<213> ORGANISM: Artificial sequence
<220> FEATURE:
<223> OTHER INFORMATION: pG1KD210.BAT-1.RHC/RkD single expression vector

<400> SEQUENCE: 93

```
ttgaagacga aagggcctcg tgatacgcct attttatag gttaatgtca tgataataat     60
ggtttcttag acgtcaggtg cacttttcg gggaaatgtg cgcggaaccc ctatttgttt    120 attttctaa atacattcaa atatgtatcc gctcatgaga caataaccct gataaatgct    180
tcaataatat tgaaaaagga agagtatgag tattcaacat ttccgtgtcg cccttattcc    240
cttttttgcg gcattttgcc ttcctgtttt tgctcaccca gaaacgctgg tgaaagtaaa    300
agatgctgaa gatcagttgg gtgcacgagt gggttacatc gaactggatc tcaacagcgg    360
taagatcctt gagagttttc gccccgaaga acgttttcca atgatgagca cttttaaagt    420
tctgctatgt ggcgcggtat tatcccgtgt tgacgccggg caagagcaac tcggtcgccg    480
catacactat tctcagaatg acttggttga gtactcacca gtcacagaaa agcatcttac    540
ggatggcatg acagtaagag aattatgcag tgctgccata accatgagtg ataacactgc    600
ggccaactta cttctgacaa cgatcggagg accgaaggag ctaaccgctt ttttgcacaa    660
catgggggat catgtaactc gccttgatcg ttgggaaccg gagctgaatg aagccatacc    720
aaacgacgag cgtgacacca cgatgcctgc agcaatggca acaacgttgc gcaaactatt    780
aactggcgaa ctacttactc tagcttcccg gcaacaatta atagactgga tggaggcgga    840
taaagttgca ggaccacttc tgcgctcggc ccttccggct ggctggttta ttgctgataa    900
atctggagcc ggtgagcgtg ggtctcgcgg tatcattgca gcactggggc cagatggtaa    960
gccctcccgt atcgtagtta tctacacgac ggggagtcag gcaactatgg atgaacgaaa   1020
tagacagatc gctgagatag gtgcctcact gattaagcat tggtaactgt cagaccaagt   1080
ttactcatat atactttaga ttgatttaaa acttcatttt taatttaaaa ggatctaggt   1140
gaagatcctt tttgataatc tcatgaccaa atcccttaa cgtgagtttt cgttccactg   1200
agcgtcagac cccgtagaaa agatcaaagg atcttcttga tccttttttt ttctgcgcgt   1260
aatctgctgc ttgcaaacaa aaaaaccacc gctaccagcg gtggtttgtt tgccggatca   1320
agagctacca actctttttc cgaaggtaac tggcttcagc agagcgcaga taccaaatac   1380
tgtccttcta gtgtagccgt agttaggcca ccacttcaag aactctgtag caccgcctac   1440
atacctcgct ctgctaatcc tgttaccagt ggctgctgcc agtggcgata agtcgtgtct   1500
taccgggttg gactcaagac gatagttacc ggataaggcg cagcggtcgg gctgaacggg   1560
gggttcgtgc acacagccca gcttggagcg aacgacctac accgaactga gatacctaca   1620
gcgtgagcta tgagaaagcg ccacgcttcc cgaagggaga aaggcggaca ggtatccggt   1680
aagcggcagg gtcggaacag gagagcgcac gagggagctt ccaggggaa acgcctggta   1740
```

```
tctttatagt cctgtcgggt ttcgccacct ctgacttgag cgtcgatttt tgtgatgctc    1800
gtcagggggg cggagcctat ggaaaaacgc cagcaacgcg ccttttttac ggttcctggc    1860
cttttgctgg ccttttgctc acatgttctt tcctgcgtta tccctgatt ctgtggataa     1920
ccgtattacc gcctttgagt gagctgatac cgctcgccgc agccgaacga ccgagcgcag    1980
cgagtcagtg agcgaggaag cggaagagcg cctgatgcgg tattttctcc ttacgcatct    2040
gtgcggtatt tcacaccgca tatggtgcac tctcagtaca atctgctctg atgccgcata    2100
gttaagccag tatacactcc gctatcgcta cgtgactggg tcatggctgc gccccgacac    2160
ccgccaacac ccgctgacgc gccctgacgg gcttgtctgc tcccggcatc cgcttacaga    2220
caagctgtga ccgtctccgg gagctgcatg tgtcagaggt tttcaccgtc atcaccgaaa    2280
cgcgcgaggc agcatgcatc tcaattagtc agcaaccata gtcccgcccc taactccgcc    2340
catcccgccc ctaactccgc ccagttccgc ccattctccg cccatggct gactaatttt     2400
ttttatttat gcagaggccg aggccgcctc ggcctctgag ctattccaga agtagtgagg    2460
aggcttttt ggaggcctag gcttttgcaa aaagctagct tacagctcag gctgcgatt      2520
tcgcgccaaa cttgacggca atcctagcgt gaaggctggt aggattttat ccccgctgcc    2580
atcatggttc gaccattgaa ctgcatcgtc gccgtgtccc aaaatatggg gattggcaag    2640
aacggagacc taccctggcc tccgctcagg aacgagttca agtacttcca agaatgacc     2700
acaacctctt cagtggaagg taaacagaat ctggtgatta tgggtaggaa aacctggttc    2760
tccattcctg agaagaatcg accttttaaag gacagaatta atatagttct cagtagagaa   2820
ctcaaagaac caccacgagg agctcatttt cttgccaaaa gtttggatga tgccttaaga   2880
cttattgaac aaccggaatt ggcaagtaaa gtagacatgg tttggatagt cggaggcagt    2940
tctgtttacc aggaagccat gaatcaacca ggccacctca gactctttgt gacaaggatc    3000
atgcaggaat ttgaaagtga cacgtttttc ccagaaattg atttggggaa atataaactt    3060
ctcccagaat acccaggcgt cctctctgag gtccaggagg aaaaaggcat caagtataag    3120
tttgaagtct acgagaagaa agactaacag gaagatgctt tcaagttctc tgctcccctc    3180
ctaaagctat gcatttttat aagaccatgg gactttgct ggctttagat ctttgtgaag     3240
gaaccttact tctgtggtgt gacataattg gacaaactac ctacagagat ttaaagctct    3300
aaggtaaata taaattttt aagtgtataa tgtgttaaac tactgattct aattgtttgt     3360
gtatttaga ttccaaccta tggaactgat gaatgggagc agtggtggaa tgcctttaat     3420
gaggaaaacc tgttttgctc agaagaaatg ccatcagtg atgatgaggc tactgctgac    3480
tctcaacatt ctactcctcc aaaaagaag agaaaggtag aagaccccaa ggactttcct    3540
tcagaattgc taagtttttt gagtcatgct gtgtttagta atagaactct tgcttgcttt    3600
gctatttaca ccacaaagga aaaagctgca ctgctataca agaaaattat ggaaaaatat    3660
tctgtaacct ttataagtag gcataacagt tataatcata atactgtt ttttcttact      3720
ccacacaggc atagagtgtc tgctattaat aactatgctc aaaaattgtg taccttttagc   3780
tttttaattt gtaaagggt taataaggaa tatttgatgt atagtgcctt gactagagat     3840
cataatcagc cataccacat ttgtagaggt tttacttgct ttaaaaaacc tcccacacct    3900
ccccctgaac ctgaaacata aaatgaatgc aattgttgtt gttaacttgt ttattgcagc    3960
ttataatggt tacaaataaa gcaatagcat cacaaatttc acaaataaag catttttttc    4020
actgcattct agttgtggtt tgtccaaact catcaatgta tcttatcatg tctactagtg    4080
gccggcccgg gcgatcgctc gagatatcta ttaatagtaa tcaattacgg ggtcattagt    4140
```

```
tcatagccca tatatggagt tccgcgttac ataacttacg gtaaatggcc cgcctggctg   4200
accgcccaac gacccccgcc cattgacgtc aataatgacg tatgttccca tagtaacgcc   4260
aatagggact ttccattgac gtcaatgggt ggagtattta cggtaaactg cccacttggc   4320
agtacatcaa gtgtatcata tgccaagtac gccccctatt gacgtcaatg acggtaaatg   4380
gcccgcctgg cattatgccc agtacatgac cttatgggac tttcctactt ggcagtacat   4440
ctacgtatta gtcatcgcta ttaccatggt gatgcggttt tggcagtaca tcaatgggcg   4500
tggatagcgg tttgactcac ggggatttcc aagtctccac cccattgacg tcaatgggag   4560
tttgttttgg caccaaaatc aacgggactt tccaaaatgt cgtaacaact ccgccccatt   4620
gacgcaaatg ggcggtaggc gtgtacggtg gaggtctat ataagcagag ctcgtttagt    4680
gaaccgtcag atcgcctgga gacgccatcc acgctgtttt gacctccata agagacaccg   4740
ggaccgatcc agcctccgcg gccgggaacg gtgcattgga acgcggattc cccgtgccaa   4800
gagtgacgta agtaccgcct atagagtcta taggcccacc cccttggctt cttatgcatg   4860
ctatactgtt tttggcttgg ggtctataca ccccccgctt ctcatgttat aggtgatggt   4920
atagcttagc ctataggtgt gggttattga ccattattga ccactcccct attggtgacg   4980
atactttcca ttactaatcc ataacatggc tctttgccac aactctcttt attggctata   5040
tgccaataca ctgtccttca gagactgaca cggactctgt attttacag gatgggtct    5100
catttattat ttacaaattc acatatacaa caccaccgtc cccagtgccc gcagttttta   5160
ttaaacataa cgtgggatct ccacgcgaat ctcgggtacg tgttccggac atgggctctt   5220
ctccggtagc ggcggagctt ctacatccga gccctgctcc catgcctcca gcgactcatg   5280
gtcgctcggc agctccttgc tcctaacagt ggaggccaga cttaggcaca gcacgatgcc   5340
caccaccacc agtgtgccgc acaaggccgt ggcggtaggg tatgtgtctg aaaatgagct   5400
cggggagcgg gcttgcaccg ctgacgcatt tggaagactt aaggcagcgg cagaagaaga   5460
tgcaggcagc tgagttgttg tgttctgata agagtcagag gtaactcccg ttgcggtgct   5520
gttaacggtg gagggcagtg tagtctgagc agtactcgtt gctgccgcgc gcgccaccag   5580
acataatagc tgacagacta acagactgtt cctttccatg ggtcttttct gcagtcaccg   5640
tccttgacac gcgtctcggg aagcttgccg ccaccatgga catgagggtc cccgctcagc   5700
tcctggggct cctgctgctc tggctcccag gtgccaaatg tgaaattgtg ttgacgcagt   5760
ctccatcctc cctgtctgca tctgtaggag acagagtcac catcacttgc agtgccaggt   5820
caagtgtaag ttacatgcac tggttccagc agaaaccagg gaaagcccct aagctctgga   5880
tctataggac atccaacctg gcttctgggg tcccatctag attcagcggc agtggatctg   5940
ggacatctta ctgtctcacc atcaacagcc tgcagcctga agattttgca acttactatt   6000
gccagcaaag gagtagtttc ccactcacgt tcggcggagg gaccaagctg gagatcaaac   6060
gtgagtggat ccatctggga taagcatgct gttttctgtc tgtccctaac atgcctgtg    6120
attatgcgca acaacacac ccaagggcag aactttgtta cttaaacacc atcctgtttg    6180
cttctttcct caggaactgt ggctgcacca tctgtcttca tcttcccgcc atctgatgag   6240
cagttgaaat ctggaactgc ctctgttgtg tgcctgctga ataacttcta tcccagagag   6300
gccaaagtac agtggaaggt ggataacgcc ctccaatcgg gtaactccca ggagagtgtc   6360
acagagcagg acagcaagga cagcacctac agcctcagca gcaccctgac gctgagcaaa   6420
gcagactacg agaaacacaa agtctacgcc tgcgaagtca cccatcaggg cctgagctcg   6480
```

```
cccgtcacaa agagcttcaa caggggagag tgttagaggg agaagtgccc ccacctgctc      6540
ctcagttcca gcctgacccc ctcccatcct ttggcctctg acccttttc cacaggggac       6600 ctaccctat tgcggtcctc cagctcatct ttcacctcac cccctcctc ctccttggct        6660 ttaattatgc taatgttgga ggagaatgaa taaataaagt gaatctttgc acctgtggtg     6720
gatctaataa aagatattta ttttcattag atatgtgtgt tggttttttg tgtgcagtgc     6780
ctctatctgg aggccaggta gggctggcct tggggaggg ggaggccaga atgactccaa      6840
gagctacagg aaggcaggtc agagacccca ctggacaaac agtggctgga ctctgcacca    6900
taacacacaa tcaacagggg agtgagctgg aaatttgcta gcgaattcta ttaatagtaa    6960
tcaattacgg ggtcattagt tcatagccca tatatggagt tccgcgttac ataacttacg    7020
gtaaatggcc cgcctggctg accgcccaac gaccccgcc cattgacgtc aataatgacg     7080
tatgttccca tagtaacgcc aatagggact ttccattgac gtcaatgggt ggagtattta   7140
cggtaaactg cccacttggc agtacatcaa gtgtatcata tgccaagtac gccccctatt   7200
gacgtcaatg acggtaaatg gcccgcctgg cattatgccc agtacatgac cttatgggac   7260
tttcctactt ggcagtacat ctacgtatta gtcatcgcta ttaccatggt gatgcggttt   7320
tggcagtaca tcaatgggcg tggatagcgg tttgactcac ggggatttcc aagtctccac   7380
cccattgacg tcaatgggag tttgttttgg caccaaaatc aacgggactt tccaaaatgt   7440
cgtaacaact ccgccccatt gacgcaaatg ggcggtaggc gtgtacggtg ggaggtctat   7500
ataagcagag ctcgtttagt gaaccgtcag atcgcctgga gacgccatcc acgctgtttt   7560
gacctccata aagacaccg ggaccgatcc agcctccgcg gccgggaacg tgcattgga     7620 acgcggattc cccgtgccaa gagtgacgta agtaccgcct atagagtcta taggcccacc   7680
cccttggctt cttatgcatg ctatactgtt tttggcttgg ggtctataca ccccccgcttc  7740 ctcatgttat aggtgatggt atagcttagc ctataggtgt gggttattga ccattattga   7800
ccactcccct attggtgacg atactttcca ttactaatcc ataacatggc tctttgccac   7860
aactctcttt attggctata tgccaataca ctgtccttca gagactgaca cggactctgt   7920 attttacag gatggggtct catttattat ttacaaattc acatatacaa caccaccgtc    7980
cccagtgccc gcagttttta ttaaacataa cgtgggatct ccacgcgaat ctcgggtacg   8040
tgttccggac atgggctctt ctccggtagc ggcggagctt ctacatccga gccctgctcc   8100
catgcctcca gcgactcatg gtcgctcggc agctccttgc tcctaacagt ggaggccaga   8160
cttaggcaca gcacgatgcc caccaccacc agtgtgccgc acaaggccgt ggcggtaggg   8220
tatgtgtctg aaaatgagct cggggagcgg gcttgcaccg ctgacgcatt tggaagactt   8280
aaggcagcgg cagaagaaga tgcaggcagc tgagttgttg tgttctgata agagtcagag   8340
gtaactcccg ttgcggtgct gttaacggtg gagggcagtg tagtctgagc agtactcgtt   8400
gctgccgcgc gcgccaccag acataatagc tgacagacta acagactgtt cctttccatg   8460
ggtcttttct gcagtcaccg tccttgacac gcgtctcggg aagcttgccg ccaccatgga   8520
ctggacctgg aggatcctct tcttggtggc agcagcaaca ggtgcccact cccaggtgca   8580
gctggtgcaa tctgggtctg agcttaagaa gcctggggcc tcagtgaaga tctcctgcaa   8640
ggcttctgga tatactttca caactatgg aatgaactgg gtgcgacagg cccctggaca   8700
agggcttcag tggatgggat ggataaaac cgacagtgga gagtcaacat atgctgaaga   8760
gttcaaggga cggtttgtct tctccttgga cacctctgtc aacacggcat atctgcagat   8820
caccagcctc acggctgagg acactggcat gtatttctgt gtgagagtcg gctacgatgc   8880
```

```
tttggactac tggggccagg gaaccctggt caccgtctcg agcgcctcca ccaagggccc    8940
atcggtcttc cccctggcac cctcctccaa gagcacctct gggggcacag cggccctggg    9000
ctgcctggtc aaggactact tccccgaacc ggtgacggtg tcgtggaact caggcgccct    9060
gaccagcggc gtgcacacct tcccggctgt cctacagtcc tcaggactct actccctcag    9120
cagcgtggtg accgtgccct ccagcagctt gggcacccag acctacatct gcaacgtgaa    9180
tcacaagccc agcaacacca aggtggacaa gaaagttgag cccaaatctt gtgacaaaac    9240
tcacacatgc ccaccgtgcc cagcacctga actcctgggg ggaccgtcag tcttcctctt    9300
ccccccaaaa cccaaggaca cccctcatgat ctcccggacc cctgaggtca catgcgtggt    9360
ggtggacgtg agccacgaag accctgaggt caagttcaac tggtacgtgg acggcgtgga    9420
ggtgcataat gccaagacaa agccgcggga ggagcagtac aacagcacgt accgggtggt    9480
cagcgtcctc accgtcctgc accaggactg gctgaatggc aaggagtaca agtgcaaggt    9540
ctccaacaaa gccctcccag cccccatcga gaaaaccatc tccaaagcca agggcagcc    9600
ccgagaacca caggtgtaca ccctgccccc atcccgggag gagatgacca agaaccaggt    9660
cagcctgacc tgcctggtca aaggcttcta tcccagcgac atcgccgtgg agtgggagag    9720
caatgggcag ccggagaaca actacaagac cacgcctccc gtgctggact ccgacggctc    9780
cttcttcctc tacagcaagc tcaccgtgga caagagcagg tggcagcagg ggaacgtctt    9840
ctcatgctcc gtgatgcatg aggctctgca caaccactac acgcagaaga gcctctccct    9900
gtctccgggt aaatgagtgc gacggccggc aagccccgct ccccgggctc tcgcggtcgc    9960
acgaggatgc ttggcacgta cccccctgtac atacttcccg ggcgcccagc atggaaataa   10020
agcaccggat ctaataaaag atatttattt tcattagata tgtgtgttgg ttttttgtgt   10080
gcagtgcctc tatctggagg ccaggtaggg ctggccttgg ggaggggga ggccagaatg    10140
actccaagag ctacaggaag gcaggtcaga gaccccactg gacaaacagt ggctggactc   10200
tgcaccataa cacacaatca acagggagt gagctggaaa tttgctagcg aattaattc    10259
```

<210> SEQ ID NO 94
<211> LENGTH: 93
<212> TYPE: PRT
<213> ORGANISM: Mus musculus

<400> SEQUENCE: 94

Gln Ile Val Leu Thr Gln Ser Pro Ala Ile Met Ser Ala Ser Pro Gly
1               5                   10                  15

Glu Lys Val Thr Ile Thr Cys Ser Ala Arg Ser Ser Val Ser Tyr Met
                20                  25                  30

His Trp Gln Gln Lys Pro Gly Thr Ser Pro Lys Leu Trp Ile Tyr Arg
            35                  40                  45

Thr Ser Asn Leu Ala Ser Gly Val Pro Ala Arg Phe Ser Gly Ser Gly
        50                  55                  60

Ser Gly Thr Ser Tyr Cys Leu Thr Ile Ser Arg Met Glu Ala Glu Asp
65                  70                  75                  80

Ala Ala Thr Tyr Tyr Cys Gln Gln Arg Ser Ser Phe Pro
                85                  90

<210> SEQ ID NO 95
<211> LENGTH: 93
<212> TYPE: PRT
<213> ORGANISM: Mus musculus

<400> SEQUENCE: 95

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met
            20                  25                  30

His Tyr Gln Tyr Lys Pro Gly Thr Ser Ser Lys Leu Pro Ser Tyr Arg
        35                  40                  45

Thr Ser Asn Leu Ala Ser Gly Val Pro Ala Arg Phe Ser Gly Ser Gly
    50                  55                  60

Ser Gly Thr Ser Tyr Cys Ser Thr Ile Ser Arg Ser Glu Ala Glu Asp
65                  70                  75                  80

Ala Ala Thr Tyr Tyr Cys Gln Gln Arg Tyr His Phe Tyr
                85                  90

<210> SEQ ID NO 96
<211> LENGTH: 93
<212> TYPE: PRT
<213> ORGANISM: Mus musculus

<400> SEQUENCE: 96

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Gln Tyr Lys Pro Gly Ser Ser Pro Lys Leu Arg Ile Tyr Arg
        35                  40                  45

Asp Ser Asn Lys Ala Ser Gly Val Pro Ala Arg Phe Ser Gly Ser Gly
    50                  55                  60

Ser Gly Thr Ser Tyr Cys Ser Thr Ile Ser Arg Ser Glu Ala Glu Asp
65                  70                  75                  80

Ala Ala Thr Tyr Tyr Cys Gln Gln Arg Trp Ser Phe Asn
                85                  90

<210> SEQ ID NO 97
<211> LENGTH: 93
<212> TYPE: PRT
<213> ORGANISM: Mus musculus

<400> SEQUENCE: 97

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ile Tyr Met
            20                  25                  30

His Trp Gln Tyr Lys Pro Gly Thr Ser Pro Lys Leu Arg Ile Tyr Arg
        35                  40                  45

Asp Ser Asn Lys Ala Ser Gly Val Pro Ala Arg Phe Ser Gly Ser Gly
    50                  55                  60

Ser Gly Thr Ser Tyr Cys Ser Thr Ile Ser Arg Ser Glu Ala Glu Asp
65                  70                  75                  80

Ala Ala Thr Tyr Tyr Cys Gln His Arg Ser Ser Phe Tyr
                85                  90

<210> SEQ ID NO 98
<211> LENGTH: 93
<212> TYPE: PRT
<213> ORGANISM: Mus musculus

<400> SEQUENCE: 98

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met
            20                  25                  30

His Tyr Gln Tyr Lys Pro Gly Thr Arg Ser Lys Leu Pro Ile Tyr Arg
        35                  40                  45

Leu Ser Asn Leu Ala Ser Gly Val Pro Ala Arg Phe Ser Gly Ser Gly
        50                  55                  60

Ser Gly Thr Ser Tyr Cys Ser Thr Ile Ser Arg Ser Glu Ala Glu Asp
65                  70                  75                  80

Ala Ala Thr Tyr Tyr Cys Gln Gln Arg Trp Ser Phe Asn
                85                  90
```

<210> SEQ ID NO 99
<211> LENGTH: 93
<212> TYPE: PRT
<213> ORGANISM: Mus musculus
<220> FEATURE:
<221> NAME/KEY: misc_feature
<222> LOCATION: (34)..(34)
<223> OTHER INFORMATION: Xaa can be any naturally occurring amino acid

<400> SEQUENCE: 99

```
Gln Ile Val Leu Thr Gln Ser Pro Ala Ile Leu Ser Ala Ser Pro Gly
1               5                   10                  15

Glu Lys Val Thr Met Thr Cys Ser Ala Ser Ser Ser Val Ser Tyr Met
            20                  25                  30

His Xaa Gln Gln Lys Pro Gly Thr Ser Ser Lys Leu Trp Ile Tyr Arg
        35                  40                  45

Ser Ile Asn Lys Ala Ser Gly Val Pro Ala Arg Phe Ser Gly Ser Gly
        50                  55                  60

Ser Gly Thr Ser Tyr Cys Ser Thr Ile Ser Arg Ser Val Lys Glu Asp
65                  70                  75                  80

Ala Ala Thr Tyr Tyr Cys Gln Gln Arg Trp Ser Phe Ser
                85                  90
```

<210> SEQ ID NO 100
<211> LENGTH: 94
<212> TYPE: PRT
<213> ORGANISM: Mus musculus

<400> SEQUENCE: 100

```
Gln Ile Val Leu Thr Gln Ser Pro Ala Ile Met Ser Ala Ser Pro Gly
1               5                   10                  15

Glu Lys Val Thr Met Thr Cys Ser Ala Arg Ser Ser Val Val Ser Tyr
            20                  25                  30

Met Leu Tyr Gln Tyr Lys Pro Gly Thr Ser Ser Lys Leu Trp Ile Tyr
        35                  40                  45

Arg Ser Ser Asn Leu Ala Ser Gly Val Pro Ala Arg Phe Ser Gly Ser
        50                  55                  60

Gly Ser Gly Thr Ser Tyr Cys Ser Thr Ile Ser Arg Ser Glu Ala Glu
65                  70                  75                  80

Asp Ala Ala Thr Tyr Phe Cys Gln Gln Arg Tyr Pro Gln Tyr
                85                  90
```

<210> SEQ ID NO 101
<211> LENGTH: 93
<212> TYPE: PRT

<213> ORGANISM: Mus musculus

<400> SEQUENCE: 101

Gln Ile Leu Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Gln Tyr Lys Pro Gly Thr Ser Ser Lys Leu Pro Ile Tyr Arg
        35                  40                  45

Asp Ser Asn Leu Ala Ser Gly Val Phe Ala Arg Phe Ser Gly Ser Gly
    50                  55                  60

Ser Gly Thr Ser Tyr Cys Ser Thr Ile Ser Arg Ser Glu Ala Glu Asp
65                  70                  75                  80

Ala Ala Thr Tyr Tyr Cys Gln His Arg Ser Ser Phe Tyr
                85                  90

<210> SEQ ID NO 102
<211> LENGTH: 94
<212> TYPE: PRT
<213> ORGANISM: Mus musculus

<400> SEQUENCE: 102

Glu Ile Leu Leu Thr Gln Ser Pro Ala Ile Ile Ala Ala Ser Pro Gly
1               5                   10                  15

Glu Lys Val Thr Ile Thr Cys Ser Ala Ser Ser Val Ser Tyr Met
            20                  25                  30

Asn Trp Tyr Gln Gln Lys Pro Gly Ser Ser Pro Lys Ile Trp Ile Tyr
        35                  40                  45

Gly Ile Ser Asn Leu Ala Ser Gly Val Pro Ala Arg Phe Ser Gly Ser
    50                  55                  60

Gly Ser Gly Thr Ser Phe Ser Phe Thr Ile Asn Ser Met Glu Ala Glu
65                  70                  75                  80

Asp Val Ala Thr Tyr Tyr Cys Gln Gln Arg Ser Ser Tyr Pro
                85                  90

<210> SEQ ID NO 103
<211> LENGTH: 93
<212> TYPE: PRT
<213> ORGANISM: Mus musculus

<400> SEQUENCE: 103

Leu Thr Gln Ser Pro Ala Ile Met Ala Ala Ser Leu Gly Glu Lys Val
1               5                   10                  15

Thr Met Thr Cys Ser Ala Ser Ser Ser Val Ser Ser Ser Tyr Leu His
            20                  25                  30

Trp Tyr Gln Gln Lys Ser Gly Thr Ser Pro Lys Pro Trp Ile Tyr Gly
        35                  40                  45

Thr Ser Asn Leu Ala Ser Gly Val Pro Val Arg Phe Ser Gly Ser Gly
    50                  55                  60

Ser Gly Thr Ser Tyr Ser Leu Thr Ile Ser Ser Met Glu Ala Glu Asp
65                  70                  75                  80

Ala Ala Thr Tyr Tyr Cys Gln Gln Trp Ser Ser Tyr Pro
                85                  90

<210> SEQ ID NO 104
<211> LENGTH: 96
<212> TYPE: PRT
<213> ORGANISM: Mus musculus

```
<400> SEQUENCE: 104

Glu Asn Val Leu Thr Gln Ser Pro Ala Ile Met Ala Ala Ser Pro Gly
1               5                   10                  15

Glu Lys Val Thr Met Thr Cys Ser Ala Ser Ser Ser Val Ser Ser Ser
                20                  25                  30

Asn Leu His Trp Tyr Gln Gln Lys Ser Gly Thr Ser Thr Lys Phe Trp
            35                  40                  45

Ile Tyr Arg Thr Ser Asn Leu Ala Ser Glu Val Pro Ala Pro Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Trp Ser Gly Tyr Pro
                85                  90                  95

<210> SEQ ID NO 105
<211> LENGTH: 94
<212> TYPE: PRT
<213> ORGANISM: Mus musculus

<400> SEQUENCE: 105

Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Ser Val Ser Tyr Met
                20                  25                  30

His Trp Tyr Gln Gln Lys Ser Gly Thr Ser Pro Lys Pro Trp Ile Tyr
            35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu
                85                  90

<210> SEQ ID NO 106
<211> LENGTH: 96
<212> TYPE: PRT
<213> ORGANISM: Mus musculus

<400> SEQUENCE: 106

Glu Asn Val Leu Thr Gln Ser Pro Ala Ile Met Ala Ala Ser Leu Gly
1               5                   10                  15

Glu Lys Val Thr Met Thr Cys Ser Ala Ser Ser Ser Val Ser Ser Ser
                20                  25                  30

Tyr Leu His Trp Tyr Gln Gln Lys Ser Gly Thr Ser Pro Lys Leu Trp
            35                  40                  45

Ile Tyr Gly Thr Ser Asn Leu Ala Ser Gly Val Pro Ala Arg Phe Ser
    50                  55                  60

Gly Ser Gly Ala Gly Ile Ser Tyr Ser Leu Thr Ile Ser Ser Met Glu
65                  70                  75                  80

Ala Glu Asn Asp Ala Thr Tyr Tyr Cys Gln Gln Trp Ser Gly Tyr Pro
                85                  90                  95

<210> SEQ ID NO 107
<211> LENGTH: 96
<212> TYPE: PRT
<213> ORGANISM: Mus musculus
```

<400> SEQUENCE: 107

Glu Asn Val Leu Thr Gln Ser Pro Ala Ile Met Ala Ala Ser Leu Gly
1               5                   10                  15

Gln Lys Val Thr Met Thr Cys Ser Ala Ser Ser Val Ser Ser
            20                  25                  30          Ser

Tyr Leu His Trp Tyr Gln Gln Lys Ser Gly Ala Ser Pro Lys Pro Leu
            35                  40                  45

Ile His Arg Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Val Glu
65                  70                  75                  80

Ala Glu Asp Asp Ala Thr Tyr Tyr Cys Gln Gln Trp Ser Gly Tyr Pro
                85                  90                  95

<210> SEQ ID NO 108
<211> LENGTH: 94
<212> TYPE: PRT
<213> ORGANISM: Mus musculus

<400> SEQUENCE: 108

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
            20                  25                  30

Tyr Trp Tyr Gln Gln Lys Ser Asp Ala Ser Pro Lys Leu Trp Ile Tyr
            35                  40                  45

Tyr Thr Ser Asn Leu Ala Pro Gly Val Pro Ala Arg Phe Ser Gly Ser
        50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro
                85                  90

<210> SEQ ID NO 109
<211> LENGTH: 94
<212> TYPE: PRT
<213> ORGANISM: Mus musculus

<400> SEQUENCE: 109

Gly Ile Val Leu Thr Gln Ser Pro Thr Thr Met Thr Ala Phe Pro Gly
1               5                   10                  15

Glu Asn Val Thr Ile Thr Cys Ser Ala Ser Ser Ser Ile Asn Tyr Ile
            20                  25                  30

His Trp Tyr Gln Gln Lys Ser Gly Asn Thr Pro Lys Gln Lys Ile Tyr
            35                  40                  45

Lys Thr Ser Asp Leu Pro Ser Gly Val Pro Thr Leu Phe Ser Gly Ser
        50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Trp Ser Gly Tyr Pro
                85                  90

<210> SEQ ID NO 110
<211> LENGTH: 98
<212> TYPE: PRT
<213> ORGANISM: Mus musculus

<400> SEQUENCE: 110

-continued

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asp Ser Gly Glu Ser Thr Tyr Ala Glu Glu Phe
    50                  55                  60

Lys Gly Arg Phe Ala Phe Ser Leu Glu Thr Ser Ala Asn Thr Ala Tyr
65                  70                  75                  80

Leu Gln Ile Asn Asn Leu Asn Asn Glu Asp Thr Ala Thr Tyr Phe Cys
                85                  90                  95

Val Arg

<210> SEQ ID NO 111
<211> LENGTH: 98
<212> TYPE: PRT
<213> ORGANISM: Mus musculus

<400> SEQUENCE: 111

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg

<210> SEQ ID NO 112
<211> LENGTH: 98
<212> TYPE: PRT
<213> ORGANISM: Mus musculus

<400> SEQUENCE: 112

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg

<210> SEQ ID NO 113

```
<211> LENGTH: 96
<212> TYPE: PRT
<213> ORGANISM: Mus musculus

<400> SEQUENCE: 113

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

<210> SEQ ID NO 114
<211> LENGTH: 98
<212> TYPE: PRT
<213> ORGANISM: Mus musculus

<400> SEQUENCE: 114

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg

<210> SEQ ID NO 115
<211> LENGTH: 98
<212> TYPE: PRT
<213> ORGANISM: Mus musculus

<400> SEQUENCE: 115

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg
```

<210> SEQ ID NO 116
<211> LENGTH: 98
<212> TYPE: PRT
<213> ORGANISM: Mus musculus

<400> SEQUENCE: 116

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Gln Ala Pro Gly Lys Gly Leu Lys Trp Met
            35                  40                  45

Gly Trp Ile Asn Thr Glu Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg

<210> SEQ ID NO 117
<211> LENGTH: 98
<212> TYPE: PRT
<213> ORGANISM: Mus musculus

<400> SEQUENCE: 117

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Ala Met His Trp Val Lys Gln Ala Pro Gly Lys Gly Leu Lys Trp Met
            35                  40                  45

Gly Trp Lys Tyr Thr Asn Thr Gly Glu Pro Thr Tyr Gly Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg

<210> SEQ ID NO 118
<211> LENGTH: 93
<212> TYPE: PRT
<213> ORGANISM: Mus musculus

<400> SEQUENCE: 118

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
        50                  55                  60

Lys Gly Arg Phe Ala Phe Ser Leu Glu Thr Cys Ala Ser Thr Ala Tyr
65                  70                  75                  80

```
Leu Gln Ile Asn Asn Leu Lys Asn Gln Asp Thr Ala Thr
                85                  90

<210> SEQ ID NO 119
<211> LENGTH: 94
<212> TYPE: PRT
<213> ORGANISM: Mus musculus

<400> SEQUENCE: 119

Gln Leu Val Gln Ser Gly Pro Glu Leu Lys Lys Pro Gly Glu Thr Val
1               5                   10                  15

Lys Ile Ser Cys Lys Ala Ser Gly Tyr Thr Phe Thr Thr Ala Gly Met
            20                  25                  30

Gln Trp Val Gln Lys Met Pro Gly Lys Gly Leu Lys Trp Ile Gly Trp
        35                  40                  45

Ile Asn Thr His Ser Gly Val Pro Lys Tyr Ala Glu Asp Phe Lys Gly
    50                  55                  60

Arg Phe Ala Phe Ser Leu Glu Thr Ser Ala Ser Thr Ala Tyr Leu Gln
65                  70                  75                  80

Ile Asn Asn Leu Lys Asn Glu Asp Met Ala Thr Tyr Phe Cys
                85                  90

<210> SEQ ID NO 120
<211> LENGTH: 93
<212> TYPE: PRT
<213> ORGANISM: Mus musculus

<400> SEQUENCE: 120

Leu Val Gln Ser Gly Pro Glu Leu Lys Lys Pro Gly Glu Thr Val Arg
1               5                   10                  15

Ile Ser Cys Lys Ala Ser Gly Tyr Thr Phe Thr Thr Ala Gly Met Gln
            20                  25                  30

Trp Val Gln Lys Met Pro Gly Lys Gly Leu Lys Trp Ile Gly Trp Ile
        35                  40                  45

Asn Thr His Ser Gly Val Pro Lys Tyr Ala Glu Asp Phe Lys Gly Arg
    50                  55                  60

Phe Ala Phe Ser Leu Glu Thr Ser Ala Ser Thr Ala Tyr Leu Gln Ile
65                  70                  75                  80

Ser Asn Leu Lys Asn Glu Asp Thr Ala Thr Tyr Phe Cys
                85                  90

<210> SEQ ID NO 121
<211> LENGTH: 98
<212> TYPE: PRT
<213> ORGANISM: Mus musculus
<220> FEATURE:
<221> NAME/KEY: misc_feature
<222> LOCATION: (39)..(39)
<223> OTHER INFORMATION: Xaa can be any naturally occurring amino acid

<400> SEQUENCE: 121

Gln Val Gln Leu Gln Gln Ser Gly Pro Glu Leu Val Arg Pro Gly Thr
1               5                   10                  15

Ser Val Lys Ile Ser Cys Lys Ala Ser Gly Tyr Thr Phe Leu Thr Tyr
            20                  25                  30

Trp Met Asn Trp Val Lys Xaa Met Pro Gly Gln Gly Leu Glu Trp Ile
        35                  40                  45

Gly Gln Ile Phe Pro Ala Ser Gly Ser Thr Asn Tyr Asn Glu Met Phe
    50                  55                  60
```

```
Lys Gly Lys Ala Thr Leu Thr Val Asp Thr Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg

<210> SEQ ID NO 122
<211> LENGTH: 98
<212> TYPE: PRT
<213> ORGANISM: Mus musculus

<400> SEQUENCE: 122

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Ser Tyr
                20                  25                  30

Tyr Ile His Trp Val Lys Gln Arg Pro Gly Gln Gly Leu Glu Trp Ile
            35                  40                  45

Gly Tyr Ile Tyr Pro Arg Asp Gly Ser Thr Asn Tyr Asn Glu Lys Phe
    50                  55                  60

Lys Gly Lys Ala Thr Leu Thr Ala Asp Thr Ser Ser Thr Ala Tyr
 65                 70                  75                  80

Met Gln Leu Ser Ser Leu Thr Ser Glu Asp Ser Ala Val Tyr Phe Cys
                 85                  90                  95

Ala Arg

<210> SEQ ID NO 123
<211> LENGTH: 98
<212> TYPE: PRT
<213> ORGANISM: Mus musculus
<220> FEATURE:
<221> NAME/KEY: misc_feature
<222> LOCATION: (39)..(39)
<223> OTHER INFORMATION: Xaa can be any naturally occurring amino acid

<400> SEQUENCE: 123

Gln Val Gln Leu Gln Gln Ser Gly Pro Glu Leu Val Arg Pro Gly Thr
1               5                   10                  15

Ser Val Lys Ile Ser Cys Lys Ala Ser Gly Tyr Thr Phe Leu Thr Tyr
                20                  25                  30

Trp Met Asn Trp Val Lys Xaa Arg Pro Ala Gln Gly Leu Glu Trp Ile
            35                  40                  45

Gly Gln Ile Phe Pro Ala Ser Gly Ser Thr Asn Tyr Asn Glu Met Phe
    50                  55                  60

Lys Gly Lys Ala Thr Leu Thr Val Asp Thr Ser Ser Ser Thr Ala Tyr
 65                 70                  75                  80

Met Gln Leu Ser Ser Leu Thr Ser Glu Asp Ser Ala Val Tyr Phe Cys
                 85                  90                  95

Ala Arg

<210> SEQ ID NO 124
<211> LENGTH: 98
<212> TYPE: PRT
<213> ORGANISM: Mus musculus

<400> SEQUENCE: 124

Gln Val Gln Leu Gln Gln Ser Gly Pro Glu Leu Val Lys Pro Gly Ala
1               5                   10                  15
```

```
Ser Val Arg Ile Ser Cys Lys Ala Ser Gly Tyr Thr Phe Thr Ser Tyr
            20                  25                  30

Asn Ile His Trp Val Lys Gln Arg Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Lys Thr Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg

<210> SEQ ID NO 125
<211> LENGTH: 98
<212> TYPE: PRT
<213> ORGANISM: Mus musculus
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 125

Gln Val Gln Leu Gln Gln Ser Gly Pro Glu Leu Val Arg Pro Gly Thr
1               5                   10                  15

Ser Val Lys Ile Ser Cys Lys Ala Ser Gly Tyr Thr Phe Ile Thr Tyr
            20                  25                  30

Trp Met Asn Trp Val Lys Xaa Arg Pro Gly Gln Gly Xaa Glu Trp Ile
        35                  40                  45

Gly Gln Ile Phe Pro Ala Ser Gly Ser Thr Asn Tyr Asn Glu Met Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val His Phe Cys
                85                  90                  95

Ala Arg

<210> SEQ ID NO 126
<211> LENGTH: 98
<212> TYPE: PRT
<213> ORGANISM: Mus musculus

<400> SEQUENCE: 126

Gln Val Gln Leu Leu Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Lys Ile Leu Pro Gly Ser Gly Ser Thr Asn Tyr Asn Glu Lys Phe
    50                  55                  60

Lys Gly Lys Ala Lys Phe Thr Ala Asp Ile Ser Ser Asn Thr Ala Tyr
65                  70                  75                  80

Met Gln Leu Ser Ser Leu Thr Ser Glu Asp Ser Ala Val Tyr Tyr Cys
                85                  90                  95
```

Ala Arg

<210> SEQ ID NO 127
<211> LENGTH: 98
<212> TYPE: PRT
<213> ORGANISM: Mus musculus
<220> FEATURE:
<221> NAME/KEY: misc_feature
<222> LOCATION: (39)..(39)
<223> OTHER INFORMATION: Xaa can be any naturally occurring amino acid

<400> SEQUENCE: 127

Gln Val Gln Leu Gln Gln Ser Gly Pro Glu Leu Val Arg Pro Gly Thr
1               5                   10                  15

Ser Val Lys Ile Ser Cys Lys Ala Ser Gly Tyr Thr Phe Leu Thr Tyr
                20                  25                  30

Trp Met Asn Trp Val Lys Xaa Met Pro Gly Gln Gly Leu Glu Trp Ile
            35                  40                  45

Gly Ala Ile Phe Pro Ala Gly Gly Ser Thr Asn Tyr Asn Gln Met Phe
        50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg

<210> SEQ ID NO 128
<211> LENGTH: 98
<212> TYPE: PRT
<213> ORGANISM: Mus musculus

<400> SEQUENCE: 128

Gln Val Gln Leu Gln Gln Ser Gly Pro Glu Leu Val Arg Pro Gly Leu
1               5                   10                  15

Ser Val Lys Leu Ser Cys Lys Ala Ser Gly Tyr Ile Phe Ile Thr Tyr
                20                  25                  30

Trp Met Asn Trp Val Lys Gln Arg Pro Gly Gln Gly Leu Glu Trp Ile
            35                  40                  45

Gly Gln Ile Phe Pro Ala Ser Gly Ser Thr Asn Tyr Asn Glu Met Phe
        50                  55                  60

Glu Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg

<210> SEQ ID NO 129
<211> LENGTH: 105
<212> TYPE: PRT
<213> ORGANISM: Mus musculus

<400> SEQUENCE: 129

Gln Ile Val Leu Thr Gln Ser Pro Ala Ile Met Ser Ala Ser Pro Gly
1               5                   10                  15

Glu Lys Val Thr Ile Thr Cys Ser Ala Arg Ser Ser Val Ser Tyr Met
                20                  25                  30

Trp Phe Gln Gln Lys Pro Gly Thr Ser Pro Lys Leu Trp Ile Tyr Arg
            35                  40                  45

```
Thr Ser Asn Leu Ala Ser Gly Val Pro Ala Arg Phe Ser Gly Ser Gly
         50                  55                  60

Ser Gly Thr Ser Tyr Cys Leu Thr Ile Ser Arg Met Glu Ala Glu Asp
 65                  70                  75                  80

Ala Ala Thr Tyr Tyr Cys Gln Gln Arg Ser Ser Phe Pro Leu Thr Phe
                     85                  90                  95

Gly Ser Gly Thr Lys Leu Glu Ile Lys
            100                 105

<210> SEQ ID NO 130
<211> LENGTH: 107
<212> TYPE: PRT
<213> ORGANISM: Homo sapiens

<400> SEQUENCE: 130

Glu Ile Val Leu Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Tyr
                 20                  25                  30

Leu Asn Phe Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Gln Thr Asn Ser Ser Phe Pro Leu
                 85                  90                  95

Thr Phe Gly Ser Gly Thr Lys Leu Glu Ile Lys
            100                 105

<210> SEQ ID NO 131
<211> LENGTH: 107
<212> TYPE: PRT
<213> ORGANISM: Homo sapiens

<400> SEQUENCE: 131

Asp Ile Val Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Phe Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Ser Tyr Ser Thr Phe Pro Leu
                 85                  90                  95

Thr Phe Gly Ser Gly Thr Val Leu Glu Ile Lys
            100                 105

<210> SEQ ID NO 132
<211> LENGTH: 108
<212> TYPE: PRT
<213> ORGANISM: Homo sapiens

<400> SEQUENCE: 132
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Phe Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Trp Phe Pro Arg
                85                  90                  95

Leu Thr Phe Gln Ser Gly Thr Lys Leu Glu Ile Lys
            100                 105
```

<210> SEQ ID NO 133
<211> LENGTH: 107
<212> TYPE: PRT
<213> ORGANISM: Homo sapiens

<400> SEQUENCE: 133

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Phe Tyr Gln Gln Lys Pro Gly Gln Ala Pro Arg Leu Leu Ile
        35                  40                  45

Tyr Asp Ala Ser Asn Lys Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Ser Arg Lys Trp Phe Pro Leu
                85                  90                  95

Thr Phe Gly Ser Gly Thr Val Leu Glu Ile Lys
            100                 105
```

<210> SEQ ID NO 134
<211> LENGTH: 107
<212> TYPE: PRT
<213> ORGANISM: Homo sapiens

<400> SEQUENCE: 134

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Phe Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Trp Phe Pro Leu
                85                  90                  95

Thr Phe Gly Ser Gly Thr Val Leu Glu Ile Lys
            100                 105
```

```
<210> SEQ ID NO 135
<211> LENGTH: 107
<212> TYPE: PRT
<213> ORGANISM: Homo sapiens

<400> SEQUENCE: 135

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Phe Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Trp Phe Pro Leu
                85                  90                  95

Thr Phe Gly Ser Gly Thr Val Leu Glu Ile Lys
            100                 105

<210> SEQ ID NO 136
<211> LENGTH: 108
<212> TYPE: PRT
<213> ORGANISM: Homo sapiens

<400> SEQUENCE: 136

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Phe Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Trp Phe Pro Tyr
                85                  90                  95

Leu Thr Phe Gln Ser Gly Thr Val Leu Glu Ile Lys
            100                 105

<210> SEQ ID NO 137
<211> LENGTH: 107
<212> TYPE: PRT
<213> ORGANISM: Homo sapiens

<400> SEQUENCE: 137

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Phe Tyr Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
```

```
              65                  70                  75                  80
Glu Asp Phe Ala Val Tyr Tyr Cys Gln Gln Arg Asn Trp Phe Pro Leu
                85                  90                  95
Thr Phe Gly Ser Gly Thr Val Leu Glu Ile Lys
            100                 105
```

<210> SEQ ID NO 138
<211> LENGTH: 108
<212> TYPE: PRT
<213> ORGANISM: Homo sapiens

<400> SEQUENCE: 138

```
Glu Leu Val Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
                20                  25                  30
Leu Asn Phe Tyr Gln Gln Lys Pro Gly Lys Ala Pro Lys Leu Leu Ile
            35                  40                  45
Tyr Ala Ala Ser Asn Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Ser Tyr Ser Thr Phe Pro Phe
                85                  90                  95
Leu Thr Phe Gly Ser Gly Thr Val Leu Glu Ile Lys
            100                 105
```

<210> SEQ ID NO 139
<211> LENGTH: 107
<212> TYPE: PRT
<213> ORGANISM: Homo sapiens

<400> SEQUENCE: 139

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Gly Tyr
                20                  25                  30
Leu Ala Phe Tyr Gln Gln Lys Pro Gly Gln Ala Pro Arg Leu Leu Ile
            35                  40                  45
Tyr Asp Thr Phe Asn Arg Ala Thr Gly Ile Pro Ala Arg Phe Ser Gly
        50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Tyr Ser Trp Phe Pro Leu
                85                  90                  95
Thr Phe Gly Ser Gly Thr Val Leu Glu Ile Lys
            100                 105
```

<210> SEQ ID NO 140
<211> LENGTH: 107
<212> TYPE: PRT
<213> ORGANISM: Homo sapiens

<400> SEQUENCE: 140

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
                20                  25                  30
```

Leu Ala Phe Tyr Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Trp Phe Pro Leu
                85                  90                  95

Thr Phe Pro Ser Gly Thr Val Asp Glu Ile Lys
            100                 105

<210> SEQ ID NO 141
<211> LENGTH: 107
<212> TYPE: PRT
<213> ORGANISM: Homo sapiens

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Phe Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Thr Phe Pro Leu
                85                  90                  95

Thr Phe Gly Ser Gly Thr Val Leu Glu Ile Lys
            100                 105

<210> SEQ ID NO 142
<211> LENGTH: 108
<212> TYPE: PRT
<213> ORGANISM: Homo sapiens

<400> SEQUENCE: 142

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Phe Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Thr Phe Pro Arg
                85                  90                  95

Leu Thr Phe Gln Ser Gly Thr Val Leu Glu Ile Lys
            100                 105

<210> SEQ ID NO 143
<211> LENGTH: 109
<212> TYPE: PRT
<213> ORGANISM: Homo sapiens

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Phe Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Ser Pro Phe Pro Val
                85                  90                  95

Tyr Leu Thr Phe Gln Ser Gly Thr Lys Leu Glu Ile Lys
            100                 105

<210> SEQ ID NO 144
<211> LENGTH: 107
<212> TYPE: PRT
<213> ORGANISM: Homo sapiens

<400> SEQUENCE: 144

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Gly Tyr
            20                  25                  30

Leu Ala Phe Tyr Gln Gln Arg Pro Gly Gln Ala Pro Arg Leu Leu Val
        35                  40                  45

Tyr Asp Thr Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Asp Tyr Tyr Cys Gln Gln Arg Glu Trp Phe Pro Leu
                85                  90                  95

Thr Phe Gln Ser Gly Thr Val Leu Glu Ile Lys
            100                 105

<210> SEQ ID NO 145
<211> LENGTH: 117
<212> TYPE: PRT
<213> ORGANISM: Mus musculus

<400> SEQUENCE: 145

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asp Ser Gly Glu Ser Thr Tyr Ala Glu Glu Phe
50                  55                  60

Lys Gly Arg Phe Ala Phe Ser Leu Glu Thr Ser Ala Asn Thr Ala Tyr
65                  70                  75                  80

Leu Gln Ile Asn Asn Leu Asn Asn Glu Asp Thr Ala Thr Tyr Phe Cys
                85                  90                  95

Val Arg Val Gly Tyr Asp Ala Leu Asp Tyr Trp Gly Gln Gly Thr Ser
            100                 105                 110

Val Thr Val Ser Ser
        115

<210> SEQ ID NO 146
<211> LENGTH: 120
<212> TYPE: PRT
<213> ORGANISM: Homo sapiens

<400> SEQUENCE: 146

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Ser Phe Ser Ser His
            20                  25                  30

Ala Ile Asn Trp Val Arg Gln Ala Pro Gly Gln Gly Leu Gln Trp Met
        35                  40                  45

Gly Trp Ile Asn Thr Asn Thr Gly Ser Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Glu Ser His Ser Ser Ala Leu Asp Leu Asp Tyr Trp Gly Gln
            100                 105                 110

Gly Thr Leu Val Thr Val Ser Ser
        115                 120

<210> SEQ ID NO 147
<211> LENGTH: 126
<212> TYPE: PRT
<213> ORGANISM: Homo sapiens

<400> SEQUENCE: 147

Gln Val Gln Leu Val Gln Ser Gly Ser Glu Leu Lys Lys Pro Gly Ala
1               5                   10                  15

Ser Val Lys Ile Ser Cys Lys Ala Ser Gly Asn Thr Phe Ser Thr Tyr
            20                  25                  30

Ala Leu Asn Trp Met Arg Arg Ala Pro Gly Gln Gly Leu Lys Trp Met
        35                  40                  45

Gly Trp Ile Asn Leu Asn Thr Gly Asn Pro Thr Tyr Ala Gln Asp Phe
    50                  55                  60

Thr Gly Arg Phe Val Phe Ser Leu Asp Thr Ser Val Asn Thr Ala Phe
65                  70                  75                  80

Leu Gln Ile Ser Ser Leu Gln Ala Glu Asp Thr Ala Val Tyr Tyr Cys
                85                  90                  95

Ala Lys Pro Lys Arg Gly Thr Tyr Arg Arg Gly Tyr Tyr Tyr Tyr Pro
            100                 105                 110

Met Asp Val Trp Gly Gln Gly Thr Thr Val Thr Val Ser Ser
        115                 120                 125

<210> SEQ ID NO 148
<211> LENGTH: 125
<212> TYPE: PRT
<213> ORGANISM: Homo sapiens

<400> SEQUENCE: 148

Gln Val Gln Leu Val Gln Ser Gly Ala Glu Val Lys Lys Pro Gly Ala

```
                1               5                  10                  15
            Ser Val Lys Val Ser Cys Lys Ala Ser Gly Tyr Thr Phe Thr Ser Tyr
                            20                  25                  30

Asp Ile Asn Trp Val Arg Gln Ala Thr Gly Gln Gly Leu Glu Trp Met
                        35                  40                  45

Gly Trp Met Asn Pro Asn Ser Gly Asn Thr Gly Tyr Ala Gln Lys Phe
                    50                  55                  60

Gln Gly Arg Val Thr Met Thr Arg Asn Thr Ser Ile Ser Thr Ala Tyr
            65                  70                  75                  80

Met Glu Leu Ser Ser Leu Arg Ser Glu Asp Thr Ala Val Tyr Tyr Cys
                            85                  90                  95

Ala Arg Gly Gly Tyr Val Trp Gly Ser Tyr Arg Tyr Thr Ala Ala Phe
                        100                 105                 110

Asp Ile Trp Gly Gln Gly Thr Met Val Thr Val Ser Ser
                        115                 120                 125

<210> SEQ ID NO 149
<211> LENGTH: 123
<212> TYPE: PRT
<213> ORGANISM: Homo sapiens

<400> SEQUENCE: 149

Gln Val Gln Leu Val Gln Ser Gly Ala Glu Val Lys Lys Pro Gly Ala
            1               5                   10                  15

Ser Val Lys Val Ser Cys Glu Ala Ser Gly Val Thr Phe Thr Gly His
                            20                  25                  30

Tyr Met His Trp Val Arg Gln Ala Thr Gly Gln Gly Leu Glu Trp Met
                        35                  40                  45

Gly Trp Ile Asn Pro Asn Ser Gly Gly Thr Asn Tyr Ala Glu Lys Phe
                    50                  55                  60

Gln Gly Arg Val Thr Ile Thr Arg Asp Thr Ser Ile Asn Thr Ala Tyr
            65                  70                  75                  80

Met Glu Leu Ser Arg Leu Arg Ser Asp Asp Thr Ala Val Tyr Tyr Cys
                            85                  90                  95

Ala Arg Ala Ser Tyr Cys Gly Tyr Asp Cys Tyr Tyr Phe Phe Asp Tyr
                        100                 105                 110

Trp Gly Gln Gly Thr Leu Val Thr Val Ser Ser
                        115                 120

<210> SEQ ID NO 150
<211> LENGTH: 119
<212> TYPE: PRT
<213> ORGANISM: Homo sapiens

<400> SEQUENCE: 150

Gln Val Gln Leu Val Gln Ser Gly Ala Glu Val Lys Lys Pro Gly Ala
            1               5                   10                  15

Ser Val Lys Val Ser Cys Lys Ala Ser Gly Tyr Thr Phe Thr Ser Tyr
                            20                  25                  30

Ala Met His Trp Val Arg Gln Ala Pro Gly Gln Arg Leu Glu Trp Met
                        35                  40                  45

Gly Trp Ile Asn Ala Gly Asn Gly Asn Thr Lys Tyr Ser Gln Lys Phe
                    50                  55                  60

Gln Gly Arg Val Thr Ile Thr Arg Asp Thr Ser Ala Ser Thr Ala Tyr
            65                  70                  75                  80

Met Glu Leu Ser Ser Leu Arg Ser Glu Asp Thr Ala Val Tyr Tyr Cys
```

85                  90                  95

Ala Arg Gly Gly Tyr Tyr Gly Ser Gly Ser Asn Tyr Trp Gly Gln Gly
            100                 105                 110

Thr Leu Val Thr Val Ser Ser
        115

<210> SEQ ID NO 151
<211> LENGTH: 123
<212> TYPE: PRT
<213> ORGANISM: Homo sapiens

<400> SEQUENCE: 151

Gln Val Gln Leu Val Gln Ser Gly Pro Glu Leu Lys Lys Pro Gly Ala
1               5                   10                  15

Ser Val Lys Val Ser Cys Glu Ala Ser Gly Tyr Thr Phe Thr Gly His
            20                  25                  30

Tyr Met His Trp Val Arg Gln Ala Thr Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Ala Ser Tyr Cys Gly Tyr Asp Cys Tyr Tyr Phe Phe Asp Tyr
            100                 105                 110

Trp Gly Gln Gly Thr Leu Val Thr Val Ser Ser
        115                 120

<210> SEQ ID NO 152
<211> LENGTH: 122
<212> TYPE: PRT
<213> ORGANISM: Homo sapiens

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Lys Trp Glu Gln Pro Ile Asp Ala Pro Phe Asp Tyr Trp
            100                 105                 110

Gly Gln Gly Thr Leu Val Thr Val Ser Ser
        115                 120

<210> SEQ ID NO 153
<211> LENGTH: 123
<212> TYPE: PRT
<213> ORGANISM: Homo sapiens

<400> SEQUENCE: 153

Gln Val Gln Leu Val Gln Ser Gly Ala Glu Val Lys Pro Gly Ala
1               5                   10                  15

Ser Val Lys Val Ser Cys Glu Ala Ser Gly Tyr Thr Phe Thr Gly His
                20                  25                  30

Tyr Met His Trp Val Gly Gln Ala Thr Gly Gln Gly Leu Glu Trp Met
            35                  40                  45

Gly Trp Ile Asn Pro Asn Ser Gly Thr Asn Tyr Ala Gln Lys Phe
    50                  55                  60

Gln Gly Arg Val Thr Ile Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Ala Ser Tyr Cys Gly Tyr Asp Cys Tyr Tyr Phe Phe Asp Tyr
                100                 105                 110

Trp Gly Gln Gly Thr Leu Val Thr Val Ser Ser
            115                 120

<210> SEQ ID NO 154
<211> LENGTH: 126
<212> TYPE: PRT
<213> ORGANISM: Homo sapiens

<400> SEQUENCE: 154

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Tyr Tyr Asp Ser Asn Gly Tyr Tyr Ser Gly Tyr
                100                 105                 110

Phe Asp Tyr Trp Gly Gln Gly Thr Leu Val Thr Val Ser Ser
            115                 120                 125

<210> SEQ ID NO 155
<211> LENGTH: 121
<212> TYPE: PRT
<213> ORGANISM: Homo sapiens

<400> SEQUENCE: 155

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

```
Met Glu Leu Ser Ser Leu Arg Ser Glu Asp Thr Ala Val Tyr Tyr Cys
            85                  90                  95

Ala Arg Val Gln Trp Leu Gly Leu Thr Gly Pro Asn Asp Tyr Trp Gly
            100                 105                 110

Gln Gly Thr Leu Val Thr Val Ser Ser
            115                 120

<210> SEQ ID NO 156
<211> LENGTH: 98
<212> TYPE: PRT
<213> ORGANISM: Homo sapiens

<400> SEQUENCE: 156

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Gly Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65              70                  75                  80

Leu Gln Ile Cys Ser Leu Lys Ala Glu Asp Thr Ala Val Tyr Tyr Cys
            85                  90                  95

Ala Arg

<210> SEQ ID NO 157
<211> LENGTH: 125
<212> TYPE: PRT
<213> ORGANISM: Homo sapiens

<400> SEQUENCE: 157

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65              70                  75                  80

Met Glu Leu Ser Ser Leu Arg Ser Glu Asp Thr Ala Val Tyr Tyr Cys
            85                  90                  95

Ala Arg Asp Gly Ile Val Val Val Pro Ala Ala Ile Pro His Tyr Phe
            100                 105                 110

Asp Tyr Trp Gly Gln Gly Thr Leu Val Thr Val Ser Ser
            115                 120                 125

<210> SEQ ID NO 158
<211> LENGTH: 118
<212> TYPE: PRT
<213> ORGANISM: Homo sapiens

<400> SEQUENCE: 158

Gln Val Gln Leu Val Gln Ser Gly Ala Glu Val Lys Lys Pro Gly Ala
```

```
  1               5                  10                 15
Ser Val Lys Val Ser Cys Lys Ala Ser Gly Tyr Thr Phe Thr Ser Tyr
                 20                 25                 30

Asp Ile Asn Trp Val Arg Gln Ala Pro Gly Gln Gly Leu Glu Trp Met
         35                 40                 45

Gly Trp Met Asn Pro Asn Ser Gly Asn Thr Gly Tyr Ala Gln Lys Phe
     50                 55                 60

Gln Gly Arg Val Thr Met Thr Arg Asn Thr Ser Ile Ser Thr Ala Tyr
65              70                 75                 80

Met Glu Leu Ser Ser Leu Arg Ser Glu Asp Thr Ala Val Tyr Tyr Cys
                 85                 90                 95

Ala Arg Asn Asn Gly Ser Tyr Tyr Phe Asp Tyr Trp Gly Gln Gly Thr
                 100                105                110

Leu Val Thr Val Ser Ser
            115

<210> SEQ ID NO 159
<211> LENGTH: 98
<212> TYPE: PRT
<213> ORGANISM: Homo sapiens

<400> SEQUENCE: 159

Gln Val Gln Leu Val Gln Ser Gly Ser Glu Leu Lys Lys Pro Gly Ala
1                5                 10                 15

Ser Val Lys Val Ser Cys Lys Ala Ser Gly Tyr Thr Phe Thr Ser Tyr
                 20                 25                 30

Ala Met His Trp Val Arg Gln Ala Pro Gly Gln Gly Leu Glu Trp Met
         35                 40                 45

Gly Trp Ile Asn Thr Asn Thr Gly Asp Pro Thr Tyr Ala Gln Gly Phe
     50                 55                 60

Thr Gly Arg Phe Val Phe Ser Leu Asp Thr Ser Val Ser Thr Ala Tyr
65              70                 75                 80

Leu Gln Ile Ser Ser Leu Lys Ala Glu Asp Thr Ala Val Tyr Tyr Cys
                 85                 90                 95

Ala Arg

<210> SEQ ID NO 160
<211> LENGTH: 119
<212> TYPE: PRT
<213> ORGANISM: Homo sapiens
<220> FEATURE:
<221> NAME/KEY: misc_feature
<222> LOCATION: (108)..(108)
<223> OTHER INFORMATION: Xaa can be any naturally occurring amino acid

<400> SEQUENCE: 160

Gln Val Gln Leu Val His Ser Gly Ser Glu Phe Lys Lys Pro Gly Ala
1                5                 10                 15

Ser Val Lys Val Ser Cys Lys Ala Ser Gly Tyr Thr Phe Thr Ser Ser
                 20                 25                 30

Val Ile Asn Trp Val Arg Gln Ala Pro Gly Gln Gly Leu Glu Trp Met
         35                 40                 45

Gly Trp Ile Asn Thr Asn Thr Gly Asn Pro Thr Tyr Ala Gln Gly Phe
     50                 55                 60

Thr Gly Arg Phe Val Phe Ser Leu Asp Thr Ser Val Thr Thr Thr Tyr
65              70                 75                 80

Leu Gln Ile Asn Ser Leu Lys Ala Glu Asp Thr Ala Val Tyr Tyr Cys
```

```
                    85                  90                  95
Ala Arg Glu Leu Arg Asn Asp His Tyr Val Trp Xaa Asn Tyr Arg Pro
                100                 105                 110

Pro Leu Ser Tyr Trp Gly Gln
            115

<210> SEQ ID NO 161
<211> LENGTH: 106
<212> TYPE: PRT
<213> ORGANISM: Mus musculus
<220> FEATURE:
<221> NAME/KEY: misc_feature
<222> LOCATION: (94)..(94)
<223> OTHER INFORMATION: Xaa can be any naturally occurring amino acid

<400> SEQUENCE: 161

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Xaa Leu Thr
                85                  90                  95

Phe Gly Ala Gly Thr Lys Leu Glu Leu Lys
            100                 105

<210> SEQ ID NO 162
<211> LENGTH: 114
<212> TYPE: PRT
<213> ORGANISM: Homo sapiens
<220> FEATURE:
<221> NAME/KEY: misc_feature
<222> LOCATION: (31)..(32)
<223> OTHER INFORMATION: Xaa can be any naturally occurring amino acid

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Leu Val Xaa Xaa
                20                  25                  30

Ser Ile Ser Asn Tyr Leu Ala Trp Tyr Gln Gln Lys Pro Gly Lys Ala
            35                  40                  45

Pro Lys Leu Leu Ile Tyr Ala Ala Ser Ser Leu Glu Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Tyr
                85                  90                  95

Asn Ser Leu Pro Glu Glu Trp Thr Phe Gly Gln Gly Thr Lys Leu Glu
            100                 105                 110

Ile Lys

<210> SEQ ID NO 163
<211> LENGTH: 119
```

<212> TYPE: PRT
<213> ORGANISM: Mus musculus

<400> SEQUENCE: 163

Glu Val Gln Leu Gln Gln Ser Gly Ala Glu Leu Val Lys Pro Gly Ala
1               5                   10                  15

Ser Val Lys Leu Ser Cys Thr Ala Ser Gly Pro Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Asp Ala Asn Gly Asn Thr Lys Tyr Asp Pro Lys
    50                  55                  60

Phe Gln Gly Lys Ala Thr Ile Thr Ala Asp Thr Ser Ser Asn Thr Ala
65                  70                  75                  80

Tyr Leu Gln Leu Ser Ser Leu Thr Ser Glu Asp Thr Ala Val Tyr Tyr
                85                  90                  95

Cys Ala Arg Gly Gly Tyr Leu Arg Arg Asp Asp Tyr Trp Gly Gln Gly
            100                 105                 110

Thr Ser Val Thr Val Ser Ser
        115

<210> SEQ ID NO 164
<211> LENGTH: 128
<212> TYPE: PRT
<213> ORGANISM: Homo sapiens
<220> FEATURE:
<221> NAME/KEY: misc_feature
<222> LOCATION: (115)..(115)
<223> OTHER INFORMATION: Xaa can be any naturally occurring amino acid

<400> SEQUENCE: 164

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Trp Ile Asn Pro Tyr Gly Asn Gly Asp Thr Asn Tyr Ala Gln Lys
    50                  55                  60

Phe Gln Gly Arg Val Thr Ile Thr Ala Asp Thr Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Ala Pro Gly Tyr Gly Ser Gly Gly Cys Tyr Arg Gly
            100                 105                 110

Asp Tyr Xaa Phe Asp Trp Gly Gln Gly Thr Leu Val Thr Val Ser Ser
        115                 120                 125

<210> SEQ ID NO 165
<211> LENGTH: 5
<212> TYPE: PRT
<213> ORGANISM: Artificial sequence
<220> FEATURE:
<223> OTHER INFORMATION: synthetic peptide

<400> SEQUENCE: 165

Ser Asn Asp Thr Glu
1               5

```
<210> SEQ ID NO 166
<211> LENGTH: 11
<212> TYPE: PRT
<213> ORGANISM: Artificial sequence
<220> FEATURE:
<223> OTHER INFORMATION: Synthetic peptide

<400> SEQUENCE: 166

Asp Leu Tyr Val Ile Ser Asn Phe His Gly Thr
1               5                   10

<210> SEQ ID NO 167
<211> LENGTH: 5
<212> TYPE: PRT
<213> ORGANISM: Artificial sequence
<220> FEATURE:
<223> OTHER INFORMATION: synthetic peptide

<400> SEQUENCE: 167

Ser Asn Thr Lys Gly
1               5

<210> SEQ ID NO 168
<211> LENGTH: 7
<212> TYPE: PRT
<213> ORGANISM: Artificial sequence
<220> FEATURE:
<223> OTHER INFORMATION: synthetic peptide

<400> SEQUENCE: 168

Phe Tyr Asn Ala His Ser Arg
1               5

<210> SEQ ID NO 169
<211> LENGTH: 5
<212> TYPE: PRT
<213> ORGANISM: Artificial sequence
<220> FEATURE:
<223> OTHER INFORMATION: synthetic peptide

<400> SEQUENCE: 169

Met Leu Val Ile Phe
1               5

<210> SEQ ID NO 170
<211> LENGTH: 5
<212> TYPE: PRT
<213> ORGANISM: Artificial sequence
<220> FEATURE:
<223> OTHER INFORMATION: synthetic peptide

<400> SEQUENCE: 170

Gln Ser Gly Phe Leu
1               5

<210> SEQ ID NO 171
<211> LENGTH: 10
<212> TYPE: PRT
<213> ORGANISM: Artificial sequence
<220> FEATURE:
<223> OTHER INFORMATION: synthetic peptide

<400> SEQUENCE: 171

Asn Phe Gly Ser Arg Asp His Thr Tyr Val
1               5                   10

<210> SEQ ID NO 172
```

```
<211> LENGTH: 10
<212> TYPE: PRT
<213> ORGANISM: Artificial sequence
<220> FEATURE:
<223> OTHER INFORMATION: synthetic peptide

<400> SEQUENCE: 172

Asn Tyr Trp Thr Ser Arg Gln His Ala Asp
1               5                   10

<210> SEQ ID NO 173
<211> LENGTH: 12
<212> TYPE: PRT
<213> ORGANISM: Artificial sequence
<220> FEATURE:
<223> OTHER INFORMATION: synthetic peptide

<400> SEQUENCE: 173

Glu Asn Gly His Thr Ser Arg Ala Gln His Ala Asp
1               5                   10

<210> SEQ ID NO 174
<211> LENGTH: 11
<212> TYPE: PRT
<213> ORGANISM: Artificial sequence
<220> FEATURE:
<223> OTHER INFORMATION: synthetic peptide

<400> SEQUENCE: 174

Asp Tyr Thr Val Leu His Asn Ile Trp Pro Ser
1               5                   10

<210> SEQ ID NO 175
<211> LENGTH: 7
<212> TYPE: PRT
<213> ORGANISM: Artificial sequence
<220> FEATURE:
<223> OTHER INFORMATION: synthetic peptide

<400> SEQUENCE: 175

Pro Leu Tyr Arg Ile Trp Phe
1               5

<210> SEQ ID NO 176
<211> LENGTH: 5
<212> TYPE: PRT
<213> ORGANISM: Artificial sequence
<220> FEATURE:
<223> OTHER INFORMATION: synthetic peptide

<400> SEQUENCE: 176

Thr Ala Val Gly Ser
1               5

<210> SEQ ID NO 177
<211> LENGTH: 5
<212> TYPE: PRT
<213> ORGANISM: Artificial sequence
<220> FEATURE:
<223> OTHER INFORMATION: synthetic peptide

<400> SEQUENCE: 177

Met Ile Val Leu Thr
1               5

<210> SEQ ID NO 178
<211> LENGTH: 6
```

```
<212> TYPE: PRT
<213> ORGANISM: Artificial sequence
<220> FEATURE:
<223> OTHER INFORMATION: synthetic peptide

<400> SEQUENCE: 178

Arg Thr Lys His Gly Leu
1               5

<210> SEQ ID NO 179
<211> LENGTH: 9
<212> TYPE: PRT
<213> ORGANISM: Artificial sequence
<220> FEATURE:
<223> OTHER INFORMATION: synthetic peptide

<400> SEQUENCE: 179

Ile His Tyr Phe Thr Asn Cys Glu Asp
1               5

<210> SEQ ID NO 180
<211> LENGTH: 7
<212> TYPE: PRT
<213> ORGANISM: Artificial sequence
<220> FEATURE:
<223> OTHER INFORMATION: synthetic peptide

<400> SEQUENCE: 180

Tyr Ala Trp Gly Thr Leu Val
1               5

<210> SEQ ID NO 181
<211> LENGTH: 7
<212> TYPE: PRT
<213> ORGANISM: Artificial sequence
<220> FEATURE:
<223> OTHER INFORMATION: synthetic peptide

<400> SEQUENCE: 181

His Glu Asn Gln Ser Tyr Thr
1               5

<210> SEQ ID NO 182
<211> LENGTH: 6
<212> TYPE: PRT
<213> ORGANISM: Artificial sequence
<220> FEATURE:
<223> OTHER INFORMATION: synthetic peptide

<400> SEQUENCE: 182

Leu Ile Val Thr Ser Asn
1               5

<210> SEQ ID NO 183
<211> LENGTH: 5
<212> TYPE: PRT
<213> ORGANISM: Artificial sequence
<220> FEATURE:
<223> OTHER INFORMATION: synthetic peptide

<400> SEQUENCE: 183

Ile Leu Phe Met Val
1               5

<210> SEQ ID NO 184
<211> LENGTH: 5
<212> TYPE: PRT
```

```
<213> ORGANISM: Artificial sequence
<220> FEATURE:
<223> OTHER INFORMATION: synthetic peptide

<400> SEQUENCE: 184

Ala Leu Val Tyr Phe
1               5

<210> SEQ ID NO 185
<211> LENGTH: 6
<212> TYPE: PRT
<213> ORGANISM: Artificial sequence
<220> FEATURE:
<223> OTHER INFORMATION: synthetic peptide

<400> SEQUENCE: 185

Arg Lys Gly Ser His Asn
1               5

<210> SEQ ID NO 186
<211> LENGTH: 7
<212> TYPE: PRT
<213> ORGANISM: Artificial sequence
<220> FEATURE:
<223> OTHER INFORMATION: synthetic peptide

<400> SEQUENCE: 186

Tyr His Val Ile Ser Asp Gly
1               5

<210> SEQ ID NO 187
<211> LENGTH: 6
<212> TYPE: PRT
<213> ORGANISM: Artificial sequence
<220> FEATURE:
<223> OTHER INFORMATION: synthetic peptide

<400> SEQUENCE: 187

Tyr Trp Gly Ala Thr Leu
1               5

<210> SEQ ID NO 188
<211> LENGTH: 11
<212> TYPE: PRT
<213> ORGANISM: Artificial sequence
<220> FEATURE:
<223> OTHER INFORMATION: synthetic peptide

<400> SEQUENCE: 188

Arg Glu Trp Tyr Gly Gln Val Leu Asn Lys Ala
1               5                   10

<210> SEQ ID NO 189
<211> LENGTH: 5
<212> TYPE: PRT
<213> ORGANISM: Artificial sequence
<220> FEATURE:
<223> OTHER INFORMATION: synthetic peptide

<400> SEQUENCE: 189

Asp Leu Asn Ser Tyr
1               5

<210> SEQ ID NO 190
<211> LENGTH: 7
<212> TYPE: PRT
<213> ORGANISM: Artificial sequence
```

```
<220> FEATURE:
<223> OTHER INFORMATION: synthetic peptide

<400> SEQUENCE: 190

Ala Gly Tyr Ser Lys Thr Asn
1               5

<210> SEQ ID NO 191
<211> LENGTH: 6
<212> TYPE: PRT
<213> ORGANISM: Artificial sequence
<220> FEATURE:
<223> OTHER INFORMATION: synthetic peptide

<400> SEQUENCE: 191

Asn Ser Thr Lys Asp Gly
1               5

<210> SEQ ID NO 192
<211> LENGTH: 8
<212> TYPE: PRT
<213> ORGANISM: Artificial sequence
<220> FEATURE:
<223> OTHER INFORMATION: synthetic peptide

<400> SEQUENCE: 192

Tyr Arg Glu Asp Gly Val Ser Ala
1               5

<210> SEQ ID NO 193
<211> LENGTH: 9
<212> TYPE: PRT
<213> ORGANISM: Artificial sequence
<220> FEATURE:
<223> OTHER INFORMATION: synthetic peptide

<400> SEQUENCE: 193

Lys Asn Thr Ser Asp Arg Gly Phe Tyr
1               5
```